United States Patent
Pelcman et al.

(10) Patent No.: US 12,378,216 B2
(45) Date of Patent: Aug. 5, 2025

(54) HETEROARYL(HETEROCYCLYL)METHANOL COMPOUNDS USEFUL IN THE TREATMENT OF HYPERGLYCAEMIA

(71) Applicant: ATROGI AB, Stockholm (SE)

(72) Inventors: Benjamin Pelcman, Stockholm (SE); Tore Bengtsson, Vaxholm (SE)

(73) Assignee: ATROGI AB, Solna (SE)

( * ) Notice: Subject to any disclaimer, the term of this patent is extended or adjusted under 35 U.S.C. 154(b) by 845 days.

(21) Appl. No.: 17/439,638

(22) PCT Filed: Mar. 20, 2020

(86) PCT No.: PCT/GB2020/050760
§ 371 (c)(1),
(2) Date: Sep. 15, 2021

(87) PCT Pub. No.: WO2020/188299
PCT Pub. Date: Sep. 24, 2020

(65) Prior Publication Data
US 2022/0194920 A1 Jun. 23, 2022

(30) Foreign Application Priority Data
Mar. 20, 2019 (GB) .................... 1903832

(51) Int. Cl.
| | | |
|---|---|---|
| *C07D 401/06* | (2006.01) | |
| *A61K 31/44* | (2006.01) | |
| *A61K 31/4427* | (2006.01) | |
| *A61K 31/4439* | (2006.01) | |
| *A61K 31/444* | (2006.01) | |
| *A61K 45/06* | (2006.01) | |
| *A61P 3/10* | (2006.01) | |

(52) U.S. Cl.
CPC ............ *C07D 401/06* (2013.01); *A61K 31/44* (2013.01); *A61K 31/4427* (2013.01); *A61K 31/4439* (2013.01); *A61K 31/444* (2013.01); *A61K 45/06* (2013.01); *A61P 3/10* (2018.01)

(58) Field of Classification Search
CPC .. C07D 401/06; A61K 31/44; A61K 31/4427; A61K 31/4439; A61K 31/444; A61K 45/06; A61K 31/4545; A61K 31/55; A61P 3/10
See application file for complete search history.

(56) References Cited

U.S. PATENT DOCUMENTS

| | | | |
|---|---|---|---|
| 2,308,232 A | 1/1943 | Scheuing et al. | |
| 2,460,144 A | 1/1949 | Moore | |
| 3,056,836 A | 10/1962 | Hendrik | |
| 3,341,594 A | 9/1967 | Otto et al. | |
| 3,410,944 A | 11/1968 | Claassen et al. | |
| 3,801,631 A | 4/1974 | Comer et al. | |
| 3,910,934 A | 10/1975 | Sankey et al. | |
| 3,952,101 A | 4/1976 | Jen et al. | |
| 3,954,871 A | 5/1976 | Buu-Hoi et al. | |
| 3,985,887 A | 10/1976 | Kaiser et al. | |
| 4,024,156 A | 5/1977 | Bagli et al. | |
| 4,119,710 A | 10/1978 | Engelhardt et al. | |
| 4,223,137 A | 9/1980 | Yoshizaki et al. | |
| 4,244,967 A | 1/1981 | Engelhardt et al. | |
| 4,248,884 A | 2/1981 | Legrand et al. | |
| 4,743,604 A | 5/1988 | Alig et al. | |
| 4,814,350 A | 3/1989 | Goidl et al. | |
| 4,835,315 A | 5/1989 | Lafon | |
| 4,863,959 A | 9/1989 | Bentley et al. | |
| 4,927,836 A | 5/1990 | Holloway et al. | |
| 5,019,578 A | 5/1991 | Fisher et al. | |
| 5,061,727 A | 10/1991 | Bloom et al. | |
| 5,705,515 A | 1/1998 | Fisher et al. | |
| 6,346,532 B1 | 2/2002 | Maruyama et al. | |
| 6,403,612 B2 | 6/2002 | Nantermet et al. | |

(Continued)

FOREIGN PATENT DOCUMENTS

| | | |
|---|---|---|
| AT | 285583 B | 11/1970 |
| BE | 823841 A | 4/1975 |

(Continued)

OTHER PUBLICATIONS

Lüthy et al., Lead-oriented synthesis: Investigation of organolithium-mediated routes to 3-D scaffolds and 3-D shape analysis of a virtual lead-like library, Bioorganic & Medicinal Chemistry, 2015, 23(11): 2680-2694 (Year: 2015).*
Camille G. Wermuth, Molecular Variations Based on Isosteric Replacements, The Practice of Medicinal Chemistry, 1996, 203-237 (Year: 1996).*
CAS Registry No. 2136322-88-6 (Entered STN Oct. 26, 2017) (Year: 2017).*
Wu et al., Bidirectional Role of beta2-Adrenergic Receptor in Autoimmune Diseases. Front Pharmacol. Nov. 27, 2018;9:1313, 9 pages.
Yabe et al., Effects of DPP-4 inhibitor linagliptin and GLP-1 receptor agonist liraglutide on physiological response to hypoglycaemia in Japanese subjects with type 2 diabetes: A randomized, open-label, 2-arm parallel comparative, exploratory trial. Diabetes Obes Metab. Mar. 2017;19(3):442-447.

(Continued)

*Primary Examiner* — Alicia L Otton
*Assistant Examiner* — David M Shim
(74) *Attorney, Agent, or Firm* — McCarter & English, LLP; Michael J. DeGrazia

(57) ABSTRACT

There is herein provided a compound of formula I (I) or a pharmaceutically acceptable salt thereof, wherein the ring comprising $Q^1$ to $Q^5$, $R^1$, m, $X^1$ and ring A have meanings as provided in the description.

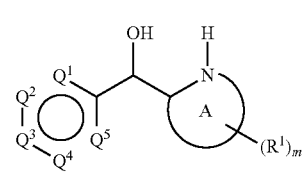

7 Claims, No Drawings

(56) References Cited

U.S. PATENT DOCUMENTS

| | | |
|---|---|---|
| 7,795,310 B2 | 9/2010 | Lee et al. |
| 9,657,348 B2 | 5/2017 | Bengtsson |
| 9,784,726 B2 | 10/2017 | Bengtsson |
| 9,891,212 B2 | 2/2018 | Bengtsson |
| 10,288,602 B2 | 5/2019 | Bengtsson |
| 11,357,757 B2 | 6/2022 | Pelcman et al. |
| 2001/0044454 A1 | 11/2001 | Nantermet et al. |
| 2003/0018061 A1 | 1/2003 | Ogawa et al. |
| 2004/0105819 A1 | 6/2004 | Hale et al. |
| 2004/0266867 A1 | 12/2004 | Cheng et al. |
| 2005/0250944 A1 | 11/2005 | Chen |
| 2006/0069161 A1 | 3/2006 | Lee et al. |
| 2006/0223886 A1 | 10/2006 | Dargazanli et al. |
| 2008/0306160 A1 | 12/2008 | Kobayashi et al. |
| 2009/0181976 A1 | 7/2009 | Buschmann et al. |
| 2009/0275616 A1 | 11/2009 | Stevens et al. |
| 2010/0022658 A1 | 1/2010 | Epstein et al. |
| 2010/0022659 A1 | 1/2010 | Meyerson et al. |
| 2010/0093807 A1 | 4/2010 | Stevens et al. |
| 2010/0173928 A1 | 7/2010 | Sabatini et al. |
| 2011/0306552 A1 | 12/2011 | Rao et al. |
| 2012/0053180 A1 | 3/2012 | Kang et al. |
| 2013/0331433 A1 | 12/2013 | Thibonnier |
| 2017/0153225 A1 | 6/2017 | Bengtsson |
| 2019/0119196 A1 | 4/2019 | Pelcman et al. |
| 2019/0314301 A1 | 10/2019 | Pelcman et al. |
| 2020/0268687 A1 | 8/2020 | Pelcman et al. |
| 2020/0268688 A1 | 8/2020 | Pelcman et al. |
| 2020/0277259 A1 | 9/2020 | Pelcman et al. |
| 2020/0315993 A1 | 10/2020 | Pelcman et al. |
| 2021/0030731 A1 | 2/2021 | Pelcman et al. |
| 2021/0338603 A1 | 11/2021 | Pelcman et al. |
| 2022/0133703 A1 | 5/2022 | Pelcman et al. |
| 2022/0152004 A1 | 5/2022 | Pelcman et al. |
| 2023/0364035 A1 | 11/2023 | Pelcman et al. |
| 2023/0365572 A1 | 11/2023 | Mutule et al. |
| 2024/0010620 A1 | 1/2024 | Mutule et al. |
| 2024/0390298 A1 | 11/2024 | Bengtsson et al. |
| 2024/0391871 A1 | 11/2024 | Bengtsson et al. |
| 2024/0398770 A1 | 12/2024 | Pelcman et al. |

FOREIGN PATENT DOCUMENTS

| | | | |
|---|---|---|---|
| CA | 1179677 A | 12/1984 | |
| CN | 1984895 A | 6/2007 | |
| CN | 103565784 A | 2/2014 | |
| CN | 105078946 A | 11/2015 | |
| CN | 106083837 A | 11/2016 | |
| DE | 638650 C | 11/1936 | |
| DE | 45721 A | 11/1966 | |
| DE | 2015573 A1 | 10/1970 | |
| DE | 2128258 A1 | 12/1971 | |
| DE | 2157040 A1 | 5/1973 | |
| DE | 2212600 A1 | 9/1973 | |
| DE | 2259282 A1 | 6/1974 | |
| DE | 2300614 A1 | 7/1974 | |
| DE | 2413102 A1 | 10/1975 | |
| DE | 2548053 A1 | 5/1976 | |
| DE | 2700193 A1 | 7/1977 | |
| DE | 2819458 A1 | 11/1978 | |
| DE | 4209989 A1 | 10/1992 | |
| EP | 0023385 A1 | 2/1981 | |
| EP | 0043807 A2 | 1/1982 | |
| EP | 0050370 A1 | 4/1982 | |
| EP | 0071399 A2 | 2/1983 | |
| EP | 0128120 A2 | 12/1984 | |
| EP | 0195396 A1 | 9/1986 | |
| EP | 0224001 A1 | 6/1987 | |
| EP | 0272976 A2 | 6/1988 | |
| EP | 0290122 A1 | 11/1988 | |
| EP | 0303546 A2 | 2/1989 | |
| EP | 0357956 A2 | 3/1990 | |
| EP | 0436435 A1 | 7/1991 | |
| EP | 0543662 A2 | 5/1993 | |
| EP | 0611003 A1 | 8/1994 | |
| EP | 0659737 A2 | 6/1995 | |
| EP | 0937458 A2 | 8/1999 | |
| EP | 1095932 A1 | 5/2001 | |
| EP | 1277736 A1 | 1/2003 | |
| EP | 1829534 A1 | 9/2007 | |
| EP | 2426202 A1 | 3/2012 | |
| FR | 1324914 A | 4/1963 | |
| FR | 2424278 A1 | 11/1979 | |
| FR | 2647310 A1 | 11/1990 | |
| GB | 1142508 A | 2/1969 | |
| GB | 1199630 A | 7/1970 | |
| GB | 1517934 A | 7/1978 | |
| GB | 2054581 A | 2/1981 | |
| GB | 2133986 A | 8/1984 | |
| GB | 2151612 A | 7/1985 | |
| JP | 49-94640 A | 9/1974 | |
| JP | 50-100065 A | 8/1975 | |
| JP | 51-122073 A | 10/1976 | |
| JP | 52-105138 A | 9/1977 | |
| JP | 54-1693 A | 1/1979 | |
| JP | 55-38375 A | 3/1980 | |
| JP | 55-45688 A | 3/1980 | |
| JP | S56-55369 A | 5/1981 | |
| JP | S56055355 A | 5/1981 | |
| JP | 57-169450 A | 10/1982 | |
| JP | 61-251621 A | 11/1986 | |
| JP | 64-42468 A | 2/1989 | |
| JP | H08-239349 A | 9/1996 | |
| JP | 2005-097149 A | 4/2005 | |
| JP | 2007-217368 A | 8/2007 | |
| JP | 2008-505176 A | 2/2008 | |
| JP | 2008-505956 A | 2/2008 | |
| JP | 2009-502733 A | 1/2009 | |
| JP | 2009-510067 A | 3/2009 | |
| JP | 2010-530402 A | 9/2010 | |
| JP | 2013-522302 A | 6/2013 | |
| JP | 2017-510560 A | 4/2017 | |
| JP | 7046842 B2 | 4/2022 | |
| NL | 7804582 A | 11/1978 | |
| RU | 2095344 C1 | 11/1997 | |
| WO | WO-1991/09596 A1 | 7/1991 | |
| WO | WO-1993/15041 A1 | 8/1993 | |
| WO | WO-1996/04234 A1 | 2/1996 | |
| WO | WO-1997/25311 A1 | 7/1997 | |
| WO | WO-1998/22480 A1 | 5/1998 | |
| WO | WO-1998/32753 A1 | 7/1998 | |
| WO | WO-1999/20607 A1 | 4/1999 | |
| WO | WO-1999/35279 A1 | 7/1999 | |
| WO | WO-1999/43326 A1 | 9/1999 | |
| WO | WO 99/65308 * | 12/1999 | ............ A01N 43/36 |
| WO | WO-1999/65308 A1 | 12/1999 | |
| WO | WO-1999/65311 A1 | 12/1999 | |
| WO | WO-1999/65877 A1 | 12/1999 | |
| WO | WO-2000/075114 A1 | 12/2000 | |
| WO | WO-2001/74782 A1 | 10/2001 | |
| WO | WO-2002/032897 A1 | 4/2002 | |
| WO | WO-2003/032969 A2 | 4/2003 | |
| WO | 2003/59911 A2 | 7/2003 | |
| WO | WO-2003/101958 A2 | 12/2003 | |
| WO | WO-2004/004451 A1 | 1/2004 | |
| WO | WO 2004/022566 A1 * | 3/2004 | ........... C07D 495/04 |
| WO | 2004/41795 A1 | 5/2004 | |
| WO | WO 2004/041795 * | 5/2004 | ........... C07D 277/64 |
| WO | WO-2004/071388 A2 | 8/2004 | |
| WO | 2004/085414 A1 | 10/2004 | |
| WO | WO-2004/110375 A2 | 12/2004 | |
| WO | WO-2005/013666 A2 | 2/2005 | |
| WO | WO-2005/025570 A1 | 3/2005 | |
| WO | WO-2005/037781 A2 | 4/2005 | |
| WO | WO-2005/075458 A1 | 8/2005 | |
| WO | 2005/111002 A2 | 11/2005 | |
| WO | WO-2005/102350 A1 | 11/2005 | |
| WO | WO-2005/108381 A1 | 11/2005 | |
| WO | WO-2005/110990 A1 | 11/2005 | |
| WO | WO-2005/114195 A1 | 12/2005 | |
| WO | 2006/005551 A1 | 1/2006 | |
| WO | WO-2006/04803 A1 | 1/2006 | |
| WO | WO-2006/027579 A2 | 3/2006 | |
| WO | 2006/108424 A2 | 10/2006 | |

(56) References Cited

FOREIGN PATENT DOCUMENTS

| | | | |
|---|---|---|---|
| WO | WO-2006/122788 A1 | 11/2006 | |
| WO | WO-2007/011065 A2 | 1/2007 | |
| WO | WO-2007/026630 A1 | 3/2007 | |
| WO | 2007/102001 A1 | 9/2007 | |
| WO | WO-2007/102011 A1 | 9/2007 | |
| WO | WO-2007/109882 A1 | 10/2007 | |
| WO | WO-2008/011453 A2 | 1/2008 | |
| WO | WO-2008/022038 A1 | 2/2008 | |
| WO | WO-2008/071948 A2 | 6/2008 | |
| WO | 2009/010660 A2 | 1/2009 | |
| WO | 2009/123870 A1 | 10/2009 | |
| WO | WO-2009/124166 A1 | 10/2009 | |
| WO | WO-2009/124167 A1 | 10/2009 | |
| WO | WO-2009/156413 A1 | 12/2009 | |
| WO | WO-2010/16939 A1 | 2/2010 | |
| WO | 2011/025774 A1 | 3/2011 | |
| WO | WO-2011/025960 A1 | 3/2011 | |
| WO | WO-2011/037815 A1 | 3/2011 | |
| WO | WO-2011/112867 A1 | 9/2011 | |
| WO | WO-2012/064269 A1 | 5/2012 | |
| WO | WO-2014/108449 A1 | 7/2014 | |
| WO | 2014/150639 A1 | 9/2014 | |
| WO | 2015/050798 A1 | 4/2015 | |
| WO | 2015/129926 A1 | 9/2015 | |
| WO | WO-2017/153737 A1 | 9/2017 | |
| WO | WO-2018/011588 A1 | 1/2018 | |
| WO | 2019/053427 A1 | 3/2019 | |
| WO | WO-2019/053425 A1 | 3/2019 | |
| WO | 2020/198466 A1 | 10/2020 | |
| WO | 2021/003161 A1 | 1/2021 | |
| ZA | 8703195 | 10/1987 | |

OTHER PUBLICATIONS

Zammit et al., Hypoglycemia in type 2 diabetes: pathophysiology, frequency, and effects of different treatment modalities. Diabetes Care. Dec. 2005;28(12):2948-61.

Ashmore et al., Effects of Dichloroisoproterenol on Blood Sugar and Plasma Free Fatty Acids. Proceedings of the Society for Experimental Biology and Medicine. 1962;109:291-294.

Chait et al., Diabetes and atherosclerosis: is there a role for hyperglycemia? J Lipid Res. Apr. 2009;50 Suppl(Suppl): S335-9.

Lands, The Effect on Blood Pressure and Toxicity of 1-{3-Fluorophenyl)-2-Aminoethanol and Related Compounds. Journal of Pharmacology and Experimental Therapeutics. Dec. 1, 1952;106(4):440-443.

CAS RN 2155248-91-0. Chemcats entry date: Jan. 15, 2019. 1 page.
CAS RN 2274711-69-0. Chemcats entry date: Jan. 15, 2019. 1 page.
CAS RN 2278127-42-5. Chemcats entry date: Jan. 15, 2019. 1 page.
CAS RN 2287791-82-4. Chemcats entry date: Jan. 15, 2019. 1 page.
CAS RN 2289315-62-2. Chemcats entry date: Jan. 15, 2019. 1 page.

U.S. Appl. No. 16/082,750, filed Sep. 6, 2018, 2019-0119196, Published.
U.S. Appl. No. 16/317,009, filed Jan. 10, 2019, 2019-0314301, Abandoned.
U.S. Appl. No. 16/908,312, filed Jun. 22, 2020, 2020-0315993, Abandoned.
U.S. Appl. No. 17/320,774, filed May 14, 2021, 2021-0338603, Published.
U.S. Appl. No. 16/646,050, filed Mar. 10, 2020, 2020-02777259, Published.
U.S. Appl. No. 16/646,497, filed Mar. 11, 2020, 2020-0268688, Published.
U.S. Appl. No. 16/646,492, filed Mar. 11, 2020, 2020-0268687, Published.
U.S. Appl. No. 16/645,286, filed Mar. 6, 2020, U.S. Pat. No. 11,357,757, Issued.
U.S. Appl. No. 17/575,175, filed Jan. 13, 2022, 2022-0133703, Published.
U.S. Appl. No. 17/439,668, filed Sep. 15, 2021, 2022-0150004, Published.
U.S. Appl. No. 14/759,572, filed Jul. 7, 2015, U.S. Pat. No. 9,784,726, Issued.
U.S. Appl. No. 15/727,851, filed Oct. 9, 2017, U.S. Pat. No. 10,288,602, Issued.
U.S. Appl. No. 14/759,747, filed Apr. 8, 2015, U.S. Pat. No. 9,657,348, Issued.
U.S. Appl. No. 15/104,830, filed Jun. 15, 2016, U.S. Pat. No. 9,891,212, Issued.
U.S. Appl. No. 15/324,580, filed Jan. 6, 2017, 2017-0153225, Abandoned.
U.S. Appl. No. 16/646,050, filed Mar. 10, 2020, 2020-0277259, Published.
U.S. Appl. No. 16/645,286, filed Mar. 6, 2020, 2021-0030731, Published.
U.S. Appl. No. 17/439,668, filed Sep. 15, 2021, Pending.

Ookawa et al., Asymmetric Synthesis of Optically Active threo- and erythro-Pyrrolidinylbenzyl Alcohol by the Highly Stereospecific Arylation of (S)-Proline and the Subsequent Highly Diastereoselective Reduction of the alpha-Amino Ketone. J Chem Soc Perkin Trans 1. 1987;1465-1471.

U.S. Appl. No. 17/320,774, filed May 14, 2021, 2021-0338603, Abandoned.
U.S. Appl. No. 16/646,050, filed Mar. 10, 2020, U.S. Pat. No. 11,427,539, Issued.
U.S. Appl. No. 16/646,497, filed Mar. 11, 2020, U.S. Pat. No. 11,648,216, Issued.
U.S. Appl. No. 18/133,060, filed Apr. 11, 2023, 2023-0364035, Published.
U.S. Appl. No. 16/646,492, filed Mar. 11, 2020, U.S. Pat. No. 11,793,774, Issued.
U.S. Appl. No. 18/027,888, filed Mar. 22, 2023, 2024-0010620, Published.
U.S. Appl. No. 18/027,890, filed Mar. 22, 2023, 2023-0365572, Published.

Ahren et al., Adrenergic innervation of pancreatic islets and modulation of insulin secretion by the sympatho-adrenal system. Cell Tissue Res. 1981;216(1):15-30.

Alessi et al., Characterization of a 3-phosphoinositide-dependent protein kinase which phosphorylates and activates protein kinase Balpha. Curr Biol. Apr. 1, 1997;7(4):261-9.

Allen et al., Studies on the inhibition of glucose metabolism in isolated fat cells by beta-adrenergic blocking agents. Biochem Pharmacol. Jun. 1969;18(6):1347-54.

Arch et al., Prospects for beta3-adrenoceptor agonists in the treatment of obesity and diabetes. International Journal of Obesity. 1996;20:191-199.

Baker et al., Chronic treatment with the beta(2)-adrenoceptor agonist prodrug BRL-47672 impairs rat skeletal muscle function by inducing a comprehensive shift to a faster muscle phenotype. J Pharmacol Exp Ther. Oct. 2006;319(1):439-46.

Barnes et al., Activation of GLUT1 by metabolic and osmotic stress: potential involvement of AMP-activated protein kinase (AMPK). J Cell Sci. Jun. 1, 2002;115(Pt 11):2433-42.

Baur et al., The identification of indacaterol as an ultralong-acting inhaled beta2-adrenoceptor agonist. J Med Chem. May 13, 2010;53(9):3675-84.

Beak et al., alpha.-Lithioamine synthetic equivalents: syntheses of diastereoisomers from the Boc-piperidines. J Org Chem. Apr. 1, 1990;55(9):2578-2580.

Bentzinger et al., Skeletal muscle-specific ablation of raptor, but not of rictor, causes metabolic changes and results in muscle dystrophy. Cell Metab. Nov. 2008;8(5):411-24.

Bercher et al., Wirkung fluorierter Phenylathanolamine auf eine durch Katecholamine induzierte Hyperglykämie bei Ratten [The effect of fluoridated phenylethanolamines on hyperglycemia induced by catecholamines in the rat]. Acta Biol Med Ger. 1975;34(4):667-74.

Besev et al., Diastereocontrol by a hydroxyl auxiliary in the synthesis of pyrrolidines via radical cyclization. Org Lett. Sep. 5, 2002;4(18):3023-5.

Biel et al., Bronchodilators, N-substituted derivatives of 1-(3',4'-Dihydroxyphenyl)-2-aminoethanol (Arterenol). J Am Chem Soc. Jun. 1954;76:3149-53.

(56) References Cited

OTHER PUBLICATIONS

Brittain et al., Sympathomimetic bronchodilator drugs. Pharmacol Ther B. 1976;2(3):423-462.

Brown et al., A mammalian protein targeted by G1-arresting rapamycin-receptor complex. Nature. Jun. 30, 1994;369(6483):756-8.

Bryant et al., Regulated transport of the glucose transporter GLUT4. Nat Rev Mol Cell Biol. Apr. 2002;(4):267-77.

Cannon et al., Brown adipose tissue: function and physiological significance. Physiol Rev. Jan. 2004;84(1):277-359.

Carayannopoulos et al., GLUT8 is a glucose transporter responsible for insulin-stimulated glucose uptake in the blastocyst. Proc Natl Acad Sci U S A. Jun. 20, 2000;97(13):7313-8.

Castle et al., Attenuation of insulin resistance by chronic beta2-adrenergic agonist treatment possible muscle specific contributions. Life Sci. Jun. 22, 2001;69(5):599-611.

Chandler et al., Expression and localization of GLUT1 and GLUT12 in prostate carcinoma. Cancer. Apr. 15, 2003;97(8):2035-42.

Chariot et al., Effects of CRL 40827 and salbutamol on exocrine pancreatic secretion in rats. Eur J. Pharmacol. Jan. 27, 1988;146(1):17-25.

Chen et al., Syntheses of 2,5- and 2,6-difluoronorepinephrine, 2,5-difluoroepinephrine, and 2,6-difluorophenylephrine: effect of disubstitution with fluorine on adrenergic activity. J Med Chem. Nov. 26, 1993;36(24):3947-55.

Chernogubova et al., Alpha1- and beta1-adrenoceptor signaling fully compensates for beta3-adrenoceptor deficiency in brown adipocyte norepinephrine-stimulated glucose uptake. Endocrinology. May 2005;146(5):2271-84.

Chernogubova et al., Norepinephrine increases glucose transport in brown adipocytes via beta3-adrenoceptors through a cAMP, PKA, and PI3-kinase-dependent pathway stimulating conventional and novel PKCs. Endocrinology. Jan. 2004;145(1):269-80.

Cioc et al., One-Pot Synthesis of N-Substituted beta-Amino Alcohols from Aldehydes and Isocyanides. Chemistry. 2015;21(21):7808-7813. Including supporting information.

Conde et al., beta-Adrenoceptor blocking activity of halogenated thienylethanolamine derivatives. J Med Chem. Jul. 1977;20(7):970-4.

Cooperberg et al., Terbutaline and the prevention of nocturnal hypoglycemia in type 1 diabetes. Diabetes Care. Dec. 2008;31(12):2271-2.

Copp et al., TORC-specific phosphorylation of mammalian target of rapamycin (mTOR): phospho-Ser2481 is a marker for intact mTOR signaling complex 2. Cancer Res. Mar. 1, 2009;69(5):1821-7.

Cypress et al., Activation of Human Brown Adipose Tissue by a beta3-Adrenergic Receptor Agonist. Cell Metab. Jan. 2015. 21(1):33-38.

Dallner et al., Beta3-adrenergic receptors stimulate glucose uptake in brown adipocytes by two mechanisms independently of glucose transporter 4 translocation. Endocrinology. Dec. 2006;147(12):5730-9.

De Souza et al., Beta 3-adrenoceptor agonists as anti-diabetic and anti-obesity drugs in humans. Curr Pharm Des. Sep. 2001;7(14):1433-49.

Defronzo et al., Synergistic Interaction between Exercise and Insulin on Peripheral Glucose Uptake. J Clin Invest. Dec. 1981;68:1468-74.

Dehvari et al., beta(2)-Adrenoceptors increase translocation of GLUT4 via GPCR kinase sites in the receptor C-terminal tail. Br J Pharmacol. Mar. 2012;165(5):1442-56.

Drake et al., Trafficking of G protein-coupled receptors. Circ Res. Sep. 15, 2006;99(6):570-82.

Edmondson et al., Discovery of Vibegron: A Potent and Selective β3 Adrenergic Receptor Agonist for the Treatment of Overactive Bladder. J Med Chem. Jan. 28, 2016;59(2):609-23.

Elayan et al., Chronic beta2 adrenergic agonist, but not exercise, improves glucose handling in older type 2 diabetic mice. Cell Mol Neurobiol. Jul. 2012;32(5):871-7.

Engelhardt, Structure activity relationship in a series of new aminohalogen substituted phenyl-aminoethanols. Arzneimittelforschung. May 1972;22(5):869-76.

Evans et al., beta2-Adrenoceptor-mediated regulation of glucose uptake in skeletal muscle—ligand-directed signalling or a reflection of system complexity? Naunyn Schmiedebergs Arch Pharmacol. Sep. 2013;386(9):757-60.

Evron et al., GRK2: multiple roles beyond G protein-coupled receptor desensitization. Trends Pharmacol Sci. Mar. 2012;33(3):154-64.

Exton, Mechanisms of hormonal regulation of hepatic glucose metabolism. Diabetes Metab Rev. Jan. 1987;3(1):163-83.

Feldman et al., Active-Site Inhibitors of mTOR Target Rapamycin-Resistant Outputs of mTORC1 and mTORC2. PLoS Biol. Feb. 10, 2009;7(2):e38. 13 pages.

Fisher et al., BMS-187257, a Potent, Selective, and Novel Heterocyclic beta3 Adrenergic Receptor Agonist. Bioorganic & Medicinal Chemistry Letters. 1996;6(19):2253-8.

Garcia-Martinez et al., Ku-0063794 is a specific inhibitor of the mammalian target of rapamycin (mTOR). Biochem J. Jun. 12, 2009;421(1):29-42.

Gaster et al., GLUT4 is reduced in slow muscle fibers of type 2 diabetic patients: is insulin resistance in type 2 diabetes a slow, type 1 fiber disease? Diabetes. Jun. 2001;50(6):1324-9.

Gavai et al., BMS-196085: a potent and selective full agonist of the human beta(3) adrenergic receptor. Bioorg Med Chem Lett. Dec. 3, 2001;11(23):3041-4.

Gawlik et al., Targeted disruption of Slc2a8 (GLUT8) reduces motility and mitochondrial potential of spermatozoa. Mol Membr Biol. Apr. 2008;25(3):224-35.

Gilman, G proteins: transducers of receptor-generated signals. Annu Rev Biochem. 1987;56:615-49.

Green et al., Use of Akt inhibitor and a drug-resistant mutant validates a critical role for protein kinase B/Akt in the insulin-dependent regulation of glucose and system A amino acid uptake. J Biol Chem. Oct. 10, 2008;283(41):27653-67.

Greife et al., Effects of the phenethanolamine clenbuterol on protein and lipid metabolism in growing rats. J Anim Physiol a Anim Nutr. 1989;61:19-27.

Gusovsky, Measurement of second messengers in signal transduction: cAMP and inositol phosphates. Curr Protoc Neurosci. May 2001;Chapter 7:Unit7.12.

Harrison et al., Activation of cell surface glucose transporters measured by photoaffinity labeling of insulin-sensitive 3T3-L1 adipocytes. J Biol Chem. Feb. 25, 1992;267(6):3783-8.

Harrison et al., Suppressed intrinsic catalytic activity of GLUT1 glucose transporters in insulin-sensitive 3T3-L1 adipocytes. Proc Natl Acad Sci U S A. Sep. 1, 1991;88(17):7839-43.

Hawkins et al., Signalling through Class I PI3Ks in mammalian cells. Biochem Soc Trans. Nov. 2006;34(Pt 5):647-62.

Hebert et al., Direct evidence for ATP modulation of sugar transport in human erythrocyte ghosts. J Biol Chem. Aug. 5, 1986;261(22):10093-9.

Hresko et al., mTOR.RICTOR is the Ser473 kinase for Akt/protein kinase B in 3T3-L1 adipocytes. J Biol Chem. Dec. 9, 2005;280(49):40406-16.

Huang et al., The GLUT4 glucose transporter. Cell Metab. Apr. 2007;5(4):237-52.

Huang, An in vitro assay for the kinase activity of mTOR complex 2. Methods Mol Biol. 2012;821:75-86.

Hutchinson et al., Agonist effects of zinterol at the mouse and human beta(3)-adrenoceptor. Naunyn Schmiedebergs Arch Pharmacol. May 2006;373(2):158-68.

Hutchinson et al., alpha1A-adrenoceptors activate glucose uptake in L6 muscle cells through a phospholipase C-, phosphatidylinositol-3 kinase-, and atypical protein kinase C-dependent pathway. Endocrinology. Feb. 2005;146(2):901-12.

Hutchinson et al., AMP-activated protein kinase activation by adrenoceptors in L6 skeletal muscle cells: mediation by alpha1-adrenoceptors causing glucose uptake. Diabetes. Mar. 2006;55(3):682-90.

(56) References Cited

OTHER PUBLICATIONS

Inokuma et al., Uncoupling protein 1 is necessary for norepinephrine-induced glucose utilization in brown adipose tissue. Diabetes. May 2005;54(5):1385-91.
Jones et al., G protein-coupled receptor kinases 2 and 5 are differentially expressed in rat skeletal muscle and remain unchanged following beta2-agonist administration. Exp Physiol. Mar. 2003;88(2):277-84.
Jozwiak et al., Comparative molecular field analysis of the binding of the stereoisomers of fenoterol and fenoterol derivatives to the beta2 adrenergic receptor. J Med Chem. Jun. 2007;50(12):2903-15.
Kaiser et al., Adrenergic agents. 1. Synthesis and potential beta-adrenergic agonist activity of some catecholamine analogs bearing a substituted amino functionality in the meta position. J Med Chem. Jan. 1974;17(1):49-57.
Kleiman et al., Developmentally spliced PKCbetaII provides a possible link between mTORC2 and Akt kinase to regulate 3T3-L1 adipocyte insulin-stimulated glucose transport. Biochem Biophys Res Commun. Oct. 23, 2009;388(3):554-9.
Koshy et al., Quantitative Measurement of GLUT4 Translocation to the Plasma Membrane by Flow Cytometry. Jove, J Vis Exp. www.jove.com. 3 pages, (2010).
Kovala et al., Protein kinase A regulation of cAMP phosphodiesterase expression in rat skeletal myoblasts. J Biol Chem. Mar. 25, 1994;269(12):8680-5.
Kumar et al., Fat cell-specific ablation of rictor in mice impairs insulin-regulated fat cell and whole-body glucose and lipid metabolism. Diabetes. Jun. 2010;59(6):1397-406.
Lacey et al., Selective stimulation of glucagon secretion by beta 2-adrenoceptors in isolated islets of Langerhans of the rat. Br J Pharmacol. Jul. 1991;103(3):1824-8.
Lamming et al., A Central role for mTOR in lipid homeostasis. Cell Metab. Oct. 1, 2013;18(4):465-9.
Laplante et al., mTOR signaling in growth control and disease. Cell. Apr. 13, 2012;149(2):274-93.
Largis et al., Antidiabetic and antiobesity effects of a highly selective β3-adrenoceptor agonist (CL 316,243). Drug Development Research. Jun. 1994;32(2):69-76.
Lawrence et al., GLUT4 facilitates insulin stimulation and cAMP-mediated inhibition of glucose transport. Proc Natl Acad Sci U S A. Apr. 15, 1992;89(8):3493-7.
Lidell et al., Evidence for two types of brown adipose tissue in humans. Nat Med. May 2013;19(5):631-4.
Liggett et al., Characterization of beta-adrenergic receptors of human skeletal muscle obtained by needle biopsy. Am J Physiol. 1988;254:E795-8.
Liu et al., Biphasic effects of the beta-adrenoceptor agonist, BRL 37344, on glucose utilization in rat isolated skeletal muscle. Br J Pharmacol. Mar. 1996;117(6):1355-61.
Liu et al., Chronic norepinephrine infusion stimulates glucose uptake in white and brown adipose tissues. Am J Physiol. 1994;266:914-20.
Lu et al., Syntheses of (R)- and (S)-2- and 6-fluoronorepinephrine and (R)- and (S)-2- and 6-fluoroepinephrine: effect of stereochemistry on fluorine-induced adrenergic selectivities. J Med Chem. Apr. 20, 2000;43(8):1611-9.
Luthy et al., Lead-oriented synthesis: Investigation of organolithium-mediated routes to 3-D scaffolds and 3-D shape analysis of a virtual lead-like library. Bioorg Med Chem. Jun. 1, 2015;23(11):2680-94.
Macaulay et al., Isoproterenol inhibits cyclic AMP-mediated but not insulin-mediated translocation of the GLUT4 glucose transporter isoform. Mol Cell Biochem. Dec. 7, 1994;141(1):27-33.
Macheda et al., Molecular and cellular regulation of glucose transporter (GLUT) proteins in cancer. J Cell Physiol. Mar. 2005;202(3):654-62.
Marette et al., Stimulation of glucose transport by insulin and norepinephrine in isolated rat brown adipocytes. Am J Physiol. Oct. 1989;257(4 Pt 1):C714-21.
Mathvink et al., Discovery of a potent, orally bioavailable beta(3) adrenergic receptor agonist, (R)-N-[4-[2-[[2-hydroxy-2-(3-pyridinyl)ethyl]amino]ethyl]phenyl]-4-[4-[4-(trifluoromethyl)phenyl]thiazol-2-yl]benzenesulfonamide. J Med Chem. Oct. 19, 2000;43(21):3832-6.
Mathvink et al., Potent, selective 3-pyridylethanolamine beta3 adrenergic receptor agonists possessing a thiazole benzenesulfonamide pharmacophore. Bioorg Med Chem Lett. Sep. 4, 2000;10(17):1971-3.
McCarty et al., Central Stimulants. a, a-Disubstituted 2-Piperidinemethanols and 1,1-Disubstituted Heptahydrooxazolo [3,4-a]pyridines. J Am Chem Soc. 1957;79:472-480.
Mills et al., Beta-blockers and glucose control. Drug Intell Clin Pharm. Apr. 1985;19(4):246-51.
Murata et al., Indinavir inhibits the glucose transporter isoform Glut4 at physiologic concentrations. AIDS. Apr. 12, 2002;16(6):859-63.
Nave et al., Mammalian target of rapamycin is a direct target for protein kinase B: identification of a convergence point for opposing effects of insulin and amino-acid deficiency on protein translation. Biochem J. Dec. 1, 1999;344 Pt 2:427-31.
Nedergaard et al., New powers of brown fat: fighting the metabolic syndrome. Cell Metab. Mar. 2, 2011;13(3):238-40.
Nedergaard et al., PPARgamma in the control of brown adipocyte differentiation. Biochim Biophys Acta. May 30, 2005;1740(2):293-304.
Nedergaard et al., Three years with adult human brown adipose tissue. Ann N.Y. Acad Sci. 2011;1212:E20-E36.
Nedergaard et al., Unexpected evidence for active brown adipose tissue in adult humans. Am J Physiol Endocrinol Metab. 2007;293:E444-E452.
Neve et al., Turnover of beta 1- and beta 2-adrenergic receptors after down-regulation or irreversible blockade. Mol Pharmacol. Aug. 1986;30(2):104-11.
Nevzorova et al., Characterization of the beta-adrenoceptor subtype involved in mediation of glucose transport in L6 cells. Br J Pharmacol. Sep. 2002;137(1):9-18.
Nevzorova et al., Multiple signalling pathways involved in beta2-adrenoceptor-mediated glucose uptake in rat skeletal muscle cells. Br J Pharmacol. Feb. 2006;147(4):446-54.
Ngala et al., beta2-adrenoceptor agonists can both stimulate and inhibit glucose uptake in mouse soleus muscle through ligand-directed signalling. Naunyn Schmiedebergs Arch Pharmacol. Sep. 2013;386(9):761-73.
Ngala et al., Beta2-adrenoceptors and non-beta-adrenoceptors mediate effects of BRL37344 and clenbuterol on glucose uptake in soleus muscle: studies using knockout mice. Br J Pharmacol. Dec. 2009;158(7):1676-82.
Ngala et al., Metabolic responses to BRL37344 and clenbuterol in soleus muscle and C2C12 cells via different atypical pharmacologies and beta2-adrenoceptor mechanisms. Br J Pharmacol. Oct. 2008;155(3):395-406.
Ning et al., A new, one-step synthesis of 1-heteroaryl-2-alkylaminoethanols. Tetrahedron Letters. 2010;51:843-845.
Nobles et al., Distinct phosphorylation sites on the beta(2)-adrenergic receptor establish a barcode that encodes differential functions of beta-arrestin. Sci Signal. Aug. 9, 2011;4(185):ra51.
Nugent et al., Potentiation of glucose uptake in 3T3-L1 adipocytes by PPAR gamma agonists is maintained in cells expressing a PPAR gamma dominant-negative mutant: evidence for selectivity in the downstream responses to PPAR gamma activation. Mol Endocrinol. Oct. 2001;15(10):1729-38.
Palmada et al., SGK1 kinase upregulates GLUT1 activity and plasma membrane expression. Diabetes. Feb. 2006;55(2):421-7.
Pan et al., Effects of clenbuterol on insulin resistance in conscious obese Zucker rats. Am J Physiol Endocrinol Metab. Apr. 2001;280(4):E554-61.
Parmee et al., Discovery of L-755,507: a subnanomolar human beta 3 adrenergic receptor agonist. Bioorg Med Chem Lett. May 5, 1998;8(9):1107-12.
Phung et al., Pathological angiogenesis is induced by sustained Akt signaling and inhibited by rapamycin. Cancer Cell. Aug. 2006;10(2):159-70.
Plazinska et al., Molecular interactions between fenoterol stereoisomers and derivatives and the beta2-adrenergic receptor binding site

(56) References Cited

OTHER PUBLICATIONS studied by docking and molecular dynamics simulations. J Mol Model. Nov. 2013;19(11):4919-30.
Ploug et al., Kinetics of glucose transport in rat muscle: effects of insulin and contractions. Am J Physiol. 1987;253:12-20.
Polak et al., Adipose-specific knockout of raptor results in lean mice with enhanced mitochondrial respiration. Cell Metab. Nov. 2008;8(5):399-410.
PubChem CID: CID=4225365, 2-(Cyclohexylmethylamino)-1-phenylethanol, 2-[(cyclohexylmethyl)amino]-1-phenylethanol; 2-(cyclohexylmethylamino)-1-phen HMS1755E04, 1 page, Dec. 1, 2018.
PubChem CID: CID=83307546, SCHEMBL19329935; AKOS023017379. 4-[2-(Cyclohexylmethylamino)-1-hydroxyethyl]phenol. Dec. 12, 2001.
Pubchem, Compound CID: 60051619, SCHEMBL19329904, 1 page, Aug. 20, 2012.
Pubchem, Compound CID: 89173082, SCHEMBL13799302, 1 page, Feb. 13, 2015.
Rao et al., Synthesis, antimicrobial and molecular docking studies of enantiomerically pure N-alkylated beta-amino alcohols from phenylpropanolamines. Bioorg Med Chem Lett. Jul. 2014;24(14):3057-63.
Reinicke et al., Cellular distribution of Glut-1 and Glut-5 in benign and malignant human prostate tissue. J Cell Biochem. Feb. 2012;113(2):553-62.
Rodnick et al., Interaction of insulin and exercise on glucose transport in muscle. Diabetes Care. Nov. 1992;15(11):1679-89.
Rovira et al., mTOR Inhibition: Reduced Insulin Secretion and Sensitivity in a Rat Model of Metabolic Syndrome. Transplant Direct. Jan. 22, 2016;2(2):e65, 9 pages.
Rowland et al., Mapping insulin/GLUT4 circuitry. Traffic. Jun. 2011;12(6):672-81.
Rydzewski, Real World Drug Discovery, a Chemist's Guide to Biotech and Pharmaceutical Research. Elsevier, Amsterdam. pp. 42-43, (2008).
Salvador et al., Inhibition by butoxamine, propranolol and MJ1999 of the glycogenolytic action of the catecholamines in the rat. Biochem Pharmacol. Oct. 1967;16(10):2037-41.
Sanner, Stereoselective condensations of a'-lithio pyrrolidine amidines. Tetrahedron Letters. 1989;30(15):1909-1912.
Santulli et al., Pinpointing beta adrenergic receptor in ageing pathophysiology: victim or executioner? Evidence from crime scenes. Immun Ageing. Mar. 15, 2013;10(1):10.
Sarabia et al., Glucose uptake in human and animal muscle cells in culture. Biochem Cell Biol. Feb. 1990;68(2):536-42.
Sarbassov et al., Prolonged rapamycin treatment inhibits mTORC2 assembly and Akt/PKB. Mol Cell. Apr. 21, 2006;22(2):159-68.
Sarbassov et al., Rictor, a novel binding partner of mTOR, defines a rapamycin-insensitive and raptor-independent pathway that regulates the cytoskeleton. Curr Biol. Jul. 27, 2004;14(14):1296-302.
Satoh, Glycemic effects of solanine in rats. Jpn J Pharmacol. Dec. 1967;17(4):652-8.
Sekulic et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.
Sennitt et al., The contribution of classical (beta1/2-) and atypical beta-adrenoceptors to the stimulation of human white adipocyte lipolysis and right atrial appendage contraction by novel beta3-adrenoceptor agonists of differing selectivities. J Pharmacol Exp Ther. Jun. 1998;285(3):1084-95.
Shah et al., The role of glucose transporters in brain disease: diabetes and Alzheimer's Disease. Int J Mol Sci. Oct. 3, 2012;13(10):12629-55.
Shan et al., Effects of GLUT4 expression on insulin resistance in patients with advanced liver cirrhosis. J Zhejiang Univ Sci B. Aug. 2011;12(8):677-82.

Shenoy et al., G-Protein Coupled Receptor—A Potential New Drug Target to Combat Diabetic Syndrome: An Overview. IJPSR. 2011;2(10):2490-2500.
Shibata et al., Cold exposure reverses inhibitory effects of fasting on peripheral glucose uptake in rats. Am J Physiol. Jul. 1989;257(1 Pt 2):R96-101.
Shimizu et al., Activation of brown adipose tissue thermogenesis in recovery from anesthetic hypothermia in rats. Am J Physiol. Aug. 1991;261(2 Pt 2):R301-4.
Simpson et al., The facilitative glucose transporter GLUT3: 20 years of distinction. Am J Physiol Endocrinol Metab. 2008;295:E242-E253.
Sobel et al., Abolition of crypticity of Arthrobacter pyridinolis toward glucose and alpha-glucosides by tricarboxylic acid cycle intermediates. J Bacteriol. Oct. 1973;116(1):271-8.
Spiller et al., A descriptive study of adverse events from clenbuterol misuse and abuse for weight loss and bodybuilding. Subst Abus. 2013;34(3):306-12.
Sprenger et al., Biophysical techniques for detection of cAMP and cGMP in living cells. Int J Mol Sci. Apr. 12, 2013;14(4):8025-46.
Stanford et al., Brown adipose tissue regulates glucose homeostasis and insulin sensitivity. J Clin Invest. Jan. 2013;123(1):215-23.
Star et al., Glucocorticoid-associated maternal hyperglycemia: a randomized trial of insulin prophylaxis. J Matern Fetal Med. Sep.-Oct. 2000;9(5):273-7.
Taha et al., The insulin-dependent biosynthesis of GLUT1 and GLUT3 glucose transporters in L6 muscle cells is mediated by distinct pathways. Roles of p21ras and pp70 S6 kinase. J Biol Chem. Oct. 20, 1995;270(42):24678-81.
Tanis et al., Solvent and in situ catalyst preparation impacts upon Noyori reductions of aryl-chloromethyl ketones: application to syntheses of chiral 2-amino-1-aryl-ethanols. Tetrahedron: Asymmetry. Aug. 28, 2006;17(14):2154-82.
Tanis et al., The design and development of 2-aryl-2-hydroxy ethylamine substituted 1H, 7H-pyrido[1,2,3-de]quinoxaline-6-carboxamides as inhibitors of human cytomegalovirus polymerase. Bioorg Med Chem Lett. Mar. 15, 2010;20(6):1994-2000.
Taverna et al., Reversible association of cytochalasin B with the human erythrocyte membrane. Inhibition of glucose transport and the stoichiometry of cytochalasin binding. Biochim Biophys Acta. Oct. 11, 1973;323(2):207-19.
Thong et al., Turning signals on and off: GLUT4 traffic in the insulin-signaling highway. Physiology (Bethesda). Aug. 2005;20:271-84.
Torgan et al., Exercise training and clenbuterol reduce insulin resistance of obese Zucker rats. Am J Physiol. Mar. 1993;264(3 Pt 1):E373-9.
Tritos et al., Clinical review 97: Syndromes of severe insulin resistance. J Clin Endocrinol Metab. Sep. 1998;83(9):3025-30.
Unger, Die Wirkung von butedrin auf den Blutzucker. The Effect of Butedrine on Blood Sugar. Zschr Inn Med. Jour Inn Med. Apr. 8, 1961;16(17):742-745.
Vardanega-Peicher et al., Time sequence of changes in the responsiveness of glycogen breakdown to adrenergic agonists in perfused liver of rats with insulin-induced hypoglycemia. Braz J Med Biol Res. Jul. 2000;33(7):805-13.
Violin et al., G-protein-coupled receptor kinase specificity for beta-arrestin recruitment to the beta2-adrenergic receptor revealed by fluorescence resonance energy transfer. J Biol Chem. Jul. 21, 2006;281(29):20577-88.
Watson-Wright et al., The Muscle Slice—A New Preparation for the Characterization of beta-Adrenergic Binding in Fast- and Slow-twitch Skeletal Muscle. Muscle & Nerve. 1986;9:416-22.
Woo et al., Stereochemistry of an agonist determines coupling preference of beta2-adrenoceptor to different G proteins in cardiomyocytes. Mol Pharmacol. Jan. 2009;75(1):158-65.
Yamamoto et al., Beta(2)-Adrenergic activation increases glycogen synthesis in L6 skeletal muscle cells through a signalling pathway independent of cyclic AMP. Diabetologia. Jan. 2007;50(1):158-67.
Ye et al., Dual catalysis for enantioselective convergent synthesis of enantiopure vicinal amino alcohols. Nat Commun. Jan. 29, 2018;9(1):410, 9 pages.

(56) References Cited

OTHER PUBLICATIONS

Ye et al., One-Pot Cascade Hydration-Asymmetric Transfer Hydrogenation as a Practical Strategy to Construct Chiral beta-Adrenergic Receptor Blockers. ChemCatChem. Jun. 15, 2015;7(12):1801-1805.
Zeng et al., Rapamycin derivatives reduce mTORC2 signaling and inhibit AKT activation in AML. Blood. Apr. 15, 2007;109(8):3509-12.
Zhu et al., Discovery of benzamides as potent human β3 adrenergic receptor agonists. Bioorg Med Chem Lett. Jan. 1, 2016;26(1):55-9.
Ziegler et al., Endogenous epinephrine protects against obesity induced insulin resistance. Auton Neurosci. Jul. 5, 2011;162(1-2):32-4.
Ziegler et al., Epinephrine and the metabolic syndrome. Curr Hypertens Rep. Feb. 2012;14(1):1-7.
Zierath, In vitro studies of human skeletal muscle: hormonal and metabolic regulation of glucose transport. Acta Physiol Scand Suppl. 1995;626:1-96.
Zinzalla et al., Activation of mTORC2 by association with the ribosome. Cell. Mar. 4, 2011;144(5):757-68.
International Search Report and Written Opinion for Applicaton No. PCT/GB2020/050760, dated Jun. 18, 2020, 11 pages.
Agac et al., The beta2-adrenergic receptor controls inflammation by driving rapid IL-10 secretion. Brain Behav Immun. Nov. 2018;74:176-185.
Angiolillo et al., Insulin therapy is associated with platelet dysfunction in patients with type 2 diabetes mellitus on dual oral antiplatelet treatment. J Am Coll Cardiol. Jul. 18, 2006;48(2):298-304.
Aumatell et al., Enantiomeric Differentiation of a wide range of Pharmacologically Active Substances by Capillary Electrophoresis using modified β-cyclodextrins . J. Chrom. A. 1994;686:293-307.
Barrow et al., Discovery and initial structure-activity relationships of trisubstituted ureas as thrombin receptor (PAR-1) antagonists. Bioorg Med Chem Lett. Oct. 22, 2001;11(20):2691-6.
Bartus et al., Beta2-Adrenoceptor agonists as novel, safe and potentially effective therapies for Amyotrophic lateral sclerosis (ALS). Neurobiol Dis. Jan. 2016;85:11-24.
Blondin et al., Human Brown Adipocyte Thermogenesis Is Driven by beta2-AR Stimulation. Cell Metab. Aug. 4, 2020;32(2):287-300.
CAS Registry Nos. 78 pages, Feb. 21, 2024.
CAS RN 1867401-63-5. STN entry date: Feb. 16, 2016. 1 page.
CAS RN 1867631-29-5. STN entry date: Feb. 16, 2016. 1 page.
CAS RN 1867726-81-5. STN entry date: Feb. 16, 2016. 1 page.
CAS RN 1868482-79-4. STN entry date: Feb. 17, 2016. 1 page.
CAS RN 750523-33-2. STN entry date: Sep. 24, 2004. 1 page.
Chemical Abstracts Accession No. 1965:410031; & CAS Registry Nos. 2745-38-2 & 2828-13-9 (Novitskii, K. et al., "Furan series. XXXVII. Reaction of 2-vinylfuran oxide with ammonia and amines", Zhurnal Organicheskoi Khimi, 1965, vol. 1, No. 3, pp. 541-545; English Abstract), two pages.
Chemical Abstracts Accession No. 1988:130714; & CAS Registry Nos. 113371-97-4 & 113371-98-5 (Mavrova, a. et al., "NMR spectra, relative configuration, preferred conformation and physiological action of 1-(2-thienyl)-2-(alkylamino)-substituted 1-alkanols", Farmatsiya, 1986, vol. 36, No. 5, pp. 1-5; English Abstract), two pages.
Chemical Abstracts Accession No. 1989:231498; & CAS Registry No. 120750-16-5 (Machon, Z. et al., "Synthesis of 4-acetyl-3-methylisothiazole derivatives", Acta Poloniae Pharmaceutica, 1988, vol. 45, No. 1, pp. 18-25; English Abstract), two pages.
Chemical Abstracts Accession No. 1993:118906; & CAS Registry No. 145908-65-2 (Dryuk, V. G. et al., "Synthesis and pesticidal activity of 2-methyl-5-oxiranylpyridine derivatives", Fiziologicheski Aktivnye Veshchestva, 1991, vol. 23, pp. 53-58; English Abstract), one page.
Chung et al., Enantioselective nitrile anion cyclization to substituted pyrrolidines. A highly efficient synthesis of (3S,4R)-N-tert-butyl-4-arylpyrrolidine-3-carboxylic acid. J Org Chem. Apr. 29, 2005;70(9):3592-601.
Cleveland et al., The beta2-Adrenergic Receptor Agonist Formoterol Decreases Fibrotic and Mitochondrial Fusion/Fission Proteins in a Mouse Model of Diabetic Nephropathy. The FASEB Journal. Apr. 2019. 33(S1):2 pages.
Damas et al., Changes in blood glucose and plasma insulin levels induced by bradykinin in anaesthetized rats. Br J Pharmacol. Nov. 2001;134(6):1312-8.
De Amici et al., Chemoenzymatic Synthesis of Chiral Isoxazole Derivatives. J. Org. Chem. 1989;54(11):2646-50.
Ehlers, For the synthesis of fluorinated aryl ethanolamines. Journal for Practical Chemistry. 1973;315(6):1169-1174.
Ferre et al., Hypoglycemic effects of a beta-agonist, Ro 16-8714, in streptozotocin-diabetic rats: decreased hepatic glucose production and increased glucose utilization in oxidative muscles. Metabolism. Feb. 1992;41(2):180-3.
Grailer et al., Induction of M2 regulatory macrophages through the beta2-adrenergic receptor with protection during endotoxemia and acute lung injury. J Innate Immun. 2014;6(5):607-18.
Heugebaert et al., Synthesis of 1-substituted epibatidine analogues and their in vitro and in vivo evaluation as alpha4beta2 nicotinic acetylcholine receptor ligands. RSC Adv. 2014;4:2226-2234.
Hishida et al., "Wearing-off" and beta2-adrenoceptor agonist in Parkinson's disease. The Lancet. Apr. 4, 1992;339:870.
Isler et al., Anti-diabetic activity of Ro 16-8714, a beta-adrenergic agonist, in obese hyperglycaemic (ob/ob) mice and streptozotocin-diabetic rats. Diabetologia. 1984;27)291A, Abtract 242.
Jesinkey et al., Formoterol Restores Mitochondrial and Renal Function after Ischemia-Reperfusion Injury. J Am Soc Nephrol. Jun. 2014;25(6):1157-1162.
Jiang et a., Randomized, double-blind, and placebo-controlled trial of clenbuterol in denervated muscle atrophy. ISRN Pharm. 2011;2011:981254, 7 pages.
Johnson, Molecular mechanisms of beta(2)-adrenergic receptor function, response, and regulation. J Allergy Clin Immunol. Jan. 2006;117(1):18-24.
Kalinovich et al., Treatment with a beta-2-adrenoceptor agonist stimulates glucose uptake in skeletal muscle and improves glucose homeostasis, insulin resistance and hepatic steatosis in mice with diet-induced obesity. Diabetologia. Aug. 2020;63(8):1603-1615.
Kitambi et al., Vulnerability of glioblastoma cells to catastrophic vacuolization and death induced by a small molecule. Cell. Apr. 10, 2014;157(2):313-328.
Le Provost et al., Beta2-adrenoceptor activation modulates skin wound healing processes to reduce scarring. J Invest Dermatol. Jan. 2015;135(1):279-88.
Liu et al., (R)-Salbutamol Improves Imiquimod-Induced Psoriasis-Like Skin Dermatitis by Regulating the Th17/Tregs Balance and Glycerophospholipid Metabolism. Cells. Feb. 24, 2020;9(2):511, 17 pages.
Merlin et al., ould burning fat start with a brite spark? Pharmacological and nutritional ways to promote thermogenesis. Mol Nutr Food Res. Jan. 2016;60(1):18-42.
Mittal et al., Beta2-Adrenoreceptor is a regulator of the a-synuclein gene driving risk of Parkinson's disease. Science. Sep. 1, 2017;357(6354):891-898.
O'Neill et al., Pharmacological targeting of beta2-adrenoceptors is neuroprotective in the LPS inflammatory rat model of Parkinson's disease. Br J Pharmacol. Jan. 2020;177(2):282-297.
Sato et al., Improving type 2 diabetes through a distinct adrenergic signaling pathway involving mTORC2 that mediates glucose uptake in skeletal muscle. Diabetes. Dec. 2014;63(12):4115-29.
Segel et al., Hypoglycemia-associated autonomic failure in advanced type 2 diabetes. Diabetes. Mar. 2002;51(3):724-33.
STN RN 1179721-98-2, Benzenemethanol, alpha-[[(1-ethylpropyl)amino]methyl]-2,6-difluoro. 17 pages, Sep. 3, 2009.
STN RN 1821736-59-7, Benzenemethanol, alpha-[[(1,1-dimethylethyl)amino]methyl]-3,5-difluoro-. 1 page, Dec. 3, 2015.
STN RN 1848912-35-5, Benzenemethanol, 4-fluoro-alpha-[[(2-methylcyclobutyl)amino]methyl]. 1 page, Jan. 19, 2016.
STN RN 1867194-32-8, Benzenemethanol, alpha-[(cyclobutylamino)amino)methyl]-4-fluoro -. 1 page, Feb. 15, 2016.
Stn Rn 1867289-32-4, Benzenemethanol, alpha-[(cyclopentylamino)methyl]-4-fluoro-. 1 page, Feb. 16, 2016.

(56) References Cited

OTHER PUBLICATIONS

STN RN 1867403-78-8, Benzenemethanol, 4-fluoro-alpha-[[(3-methylcyclobutyl)amino]methyl]-. 1 page, Feb. 16, 2016.
STN RN 51336-98-2, alpha-[(Butylamino)methyl]-2,4-difluorobenzenemethanol. 1 page, Nov. 16, 1984.
STN RN 51336-99-3, Benzenemethanol, alpha-[(butylamino0methyl]-2,4-difluoro-hydrochloride. 1 page, Nov. 16, 1984.
STN RN 51337-00-9, alpha-[(Butylamino)methyl]-3,4-difluorobenzenemethanol. 1 page, Nov. 16, 1984.
STN RN 51384-23-7, Benzenemethanol, alpha-[(butylamino)methyl]-3,4-difluoro-, hydrochloride. 1 page, Nov. 16, 1984.
STN RN 803634-00-6, 4-Pyridinemethanol, alpha-[(butylamino)methyl]—1 page, Dec. 27, 2004.
Uc et al., Albuterol improves response to levodopa and increases skeletal muscle mass in patients with fluctuating Parkinson disease. Clin Neuropharmacol. Jul.-Aug. 2003;26(4):207-12.
Baltzly et al., N-sec- and N-t-alkyl derivatives of methoxamine and related compounds. J Med Chem. Jul. 1968;11(4):833-44.
Bercher et al., Pharmakologische Eigenschaften fluorierter Phenylathanolamine [Pharmacologic properties of fluorinated phenylethanolamine]. Acta Biol Med Ger. 1974;33(3):335-41.
Chiarino et al., New Isoxazole Derivatives with a Potent and Selective beta2-Adrenergic Activity. II Farmaco. 1985;41:440-453.
Friz, Derivati All'Azoto Aminico Dell'1-(4'Piridil)-2-Aminoetanolo. II Farmaco. 1963;18:972-980.
Grandi et al., Synthesis and pharmacological investigation of New Arylethanolamines as Beta3-Adrenoceptor Ligands. Pharm Pharmacol Commun. 1999;5:561-564.
STN RN 1868397-08-3, Benzenemethanol, 4-fluoro-alpha-[[(1-methylbutyl)amino]methyl], 1 page, Feb. 17, 2016.
STN RN 582-40-1, Benzenemethanol, alpha-[[(1,1-dimethylethyl)amino]methyl]-3-fluoro-hydrobromide. 1 page, Nov. 16, 1984.
STN RN 920800-46-0, Benzenemethanol, alpha-[[(1,1-dimethylethyl)amino]methyl]-3-fluoro-(alphaR). 1 page, Feb. 13, 2007.

Tsuiki et al., Effect of the beta-adrenoceptor agonist flerobuterol on serotonin synthesis in the rat brain. Biochem Pharmacol. Mar. 15, 2000;59(6):673-9.
Banfi et al., The Passerini Reaction. Organic reactions. John Wiley & Sons, Inc., Larry E. Overman (Ed.). vol. 65, pp. 1-59, 135-140. (2005).
Bhatt et al., Fatty liver disease in diabetes mellitus. Hepatobiliary Surg Nutr. Apr. 2015;4(2):101-8.
CAS Registry No. 1468968-76-4, Supplementary Disclosure, Accession No. 0295179790, 1 page, May 19, 2022.
CAS Registry No. 1468968-76-4, Supplementary Disclosure, Accession No. 1151383925, 1 page, May 19, 2022.
Jen et al., Adrenergic agents. 7.1 Synthesis and beta-adrenergic agonist activity of several 2-pyridylethanolamines. J Med Chem. Oct. 1977;20(10):1258-62.
Kato et al., Liver steatosis is associated with insulin resistance in skeletal muscle rather than in the liver in Japanese patients with non-alcoholic fatty liver disease. J Diabetes Investig. Mar. 2015;6(2):158-63.
Lingvay et al., Effect of insulin versus triple oral therapy on the progression of hepatic steatosis in type 2 diabetes. J Investig Med. Oct. 2012;60(7):1059-63.
STN Registry No. 1190390-92-1, 1 page, Oct. 2009.
STN Registry No. 1190611-04-1, Butanoic acid, 4-[[4-[[[(2S,5R)-5-[(R)-hydroxy-3-pyridinylmethyl]-2-pyrrolidinyl]methyl[phenyl]amino]-4-oxo. 1 page, Oct. 29, 2009.
STN Registry No. 1190614-75-5, 1 page, Oct. 29, 2009.
STN Registry No. 1644-44-6, Benzenemethanol, alpha-[[(1,1-dimethylethyl)amino]methyl]--3,4-difluoro. 1 page, Nov. 16, 1984.
STN RN 1910411-77-6, Cyclohexanecarboxylic acid, 4[[(2-hydroxy-2-phenylethyl)emino)methyl]. 3 pages, May 15, 2016.
STN RN 1942796-48-6, Benzenemethanol, 3,4-difluoro-.alpha.[[[(4-hydroxycyclohexy)methyl]amino]methyl]. 3 pages, Jun. 30, 2016.
STN RN 2060295-49-8, 4-Pyridinemethanol, .alpha.-[[[(4-propylcyclohexyl)methyl]amino]methyl]. 3 pages, Jan. 27, 2017.

* cited by examiner

HETEROARYL(HETEROCYCLYL)METHANOL COMPOUNDS USEFUL IN THE TREATMENT OF HYPERGLYCAEMIA

CROSS-REFERENCE TO RELATED APPLICATIONS

This application is a U.S. national stage filing, under 35 U.S.C. § 371 (c), of International Application No. PCT/GB2020/050760, filed on Mar. 20, 2020, which claims priority to United Kingdom Patent Application No. 1903832.2, filed on Mar. 20, 2019.

FIELD OF THE INVENTION

The present invention relates to novel compounds and compositions, and their use in the treatment of hyperglycaemia and disorders characterised by hyperglycaemia, such as type 2 diabetes. In particular, the invention relates to novel compounds, compositions and methods for the treatment of conditions such as type 2 diabetes through activation of the $\beta_2$-adrenergic receptor. Importantly, such compounds are thought to have a beneficial side-effect profile as they do not exert their effect through significant cAMP release.

BACKGROUND OF THE INVENTION

The listing or discussion of an apparently prior-published document in this specification should not necessarily be taken as an acknowledgement that the document is part of the state of the art or is common general knowledge.

Hyperglycaemia, or high blood sugar, is a condition in which an excessive amount of glucose circulates in the blood plasma. If not treated, hyperglycaemia can be a serious problem, potentially developing into life-threatening conditions such as ketoacidosis. For example, chronic hyperglycemia may cause injury to the heart, and is strongly associated with heart attacks and death in subjects with no coronary heart disease or history of heart failure. There are various causes of hyperglycaemia, including diabetes and severe insulin resistance.

Severe insulin resistance (SIR) is a condition wherein the patent experiences very low levels of (or, in extreme cases, no significant) response to insulin. There are several syndromes characterized by SIR, including Rabson-Mendenhall syndrome, Donohue's syndrome (leprechaunism), Type A and Type B syndromes of insulin resistance, the HAIR-AN (hyperandrogenism, insulin resistance, and acanthosis nigricans) syndrome, pseudoacromegaly, and lipodystrophy. The majority of these conditions have genetic causes, such as mutations in the insulin receptor gene. The prevalence for Donohue's syndrome, Rabson-Mendenhall syndrome and Type A syndrome of insulin resistance, has been reported to vary from about 50 in total reported cases to a prevalence of 1 in 100,000 people. However, since some diseases are severe and extremely rare, it is likely that many patients do not get diagnosed before they die, particularly in less developed areas of the world. Thus, the exact number of patients with these syndromes is difficult to assess.

The current standard for hyperglycaemia treatment in patients having SIR is a controlled diet, supplemented with drugs affecting insulin receptor sensitivity, such as metformin, or insulin supplement. However, particularly for disorders caused by mutations in the insulin receptor gene, this treatment is not sufficiently effective and ultimately proves unsuccessful.

Diabetes comprises two distinct diseases, type 1 (or insulin-dependent diabetes) and type 2 (insulin-independent diabetes), both of which involve the malfunction of glucose homeostasis. Type 2 diabetes affects more than 400 million people in the world and the number is rising rapidly. Complications of type 2 diabetes include severe cardiovascular problems, kidney failure, peripheral neuropathy, blindness and, in the later stages of the disease, even loss of limbs and, ultimately, death. Type 2 diabetes is characterized by insulin resistance in skeletal muscle and adipose tissue, and there is presently no definitive cure. Most treatments used today are focused on remedying dysfunctional insulin signalling or inhibiting glucose output from the liver but many of those treatments have several drawbacks and side effects. There is thus a great interest in identifying novel insulin-independent ways to treat type 2 diabetes.

In particular, it is known that in type 2 diabetes the insulin-signalling pathway is blunted in peripheral tissues, such as adipose tissue and skeletal muscle. Methods for treating type 2 diabetes typically include lifestyle changes, as well as insulin injections or oral medications to regulate glucose homeostasis. People with type 2 diabetes in the later stages of the disease develop 'beta-cell failure' i.e. the inability of the pancreas to release insulin in response to high blood glucose levels. Such patients often require insulin injections in combination with oral medications to manage their diabetes. Further, most common drugs have side effects including downregulation or desensitization of the insulin pathway and/or the promotion of lipid incorporation in adipose tissue, liver and skeletal muscle. There is thus a great interest in identifying novel ways to treat metabolic diseases including type 2 diabetes that do not include these side effects.

Following a meal, increased blood glucose levels stimulate insulin release from the pancreas. Insulin mediates normalization of the blood glucose levels. Important effects of insulin on glucose metabolism include facilitation of glucose uptake into skeletal muscle and adipocytes, and an increase of glycogen storage in the liver. Skeletal muscle and adipocytes are responsible for insulin-mediated glucose uptake and utilization in the fed state, making them very important sites for glucose metabolism.

The signalling pathway downstream from the insulin receptor has been difficult to understand in detail. In brief, control of glucose uptake by insulin involves activation of the insulin receptor (IR), the insulin receptor substrate (IRS), the phosphoinositide 3-kinase (PI3K) and thus stimulation of phosphatidylinositol (3,4,5)-triphosphate (PIP3), the mammalian target of rapamycin (also called the mechanistic target of rapamycin, mTOR), Akt/PKB (Akt) and TBC1D4 (AS160), leading to translocation of the glucose transporter 4 (GLUT4) to the plasma membrane. Akt activation is considered necessary for GLUT4 translocation.

It should be noted that skeletal muscles constitute a major part of the body weight of mammals and have a vital role in the regulation of systemic glucose metabolism, being responsible for up to 85% of whole-body glucose disposal. Glucose uptake in skeletal muscles is regulated by several intra- and extracellular signals. Insulin is the most well studied mediator but others also exist. For example, AMP activated kinase (AMPK) functions as an energy sensor in the cell, which can increase glucose uptake and fatty acid oxidation. Due to the great influence skeletal muscles have on glucose homeostasis it is plausible that additional mechanisms exist. In the light of the increased prevalence of type 2 diabetes, it is of great interest to find and characterize novel insulin-independent mechanisms to increase glucose uptake in muscle cells.

Blood glucose levels may be regulated by both insulin and catecholamines, but they are released in the body in response to different stimuli. Whereas insulin is released in response to the rise in blood sugar levels (e.g. after a meal), epinephrine and norepinephrine are released in response to various internal and external stimuli, such as exercise, emotions and stress, and also for maintaining tissue homeostasis. Insulin is an anabolic hormone that stimulates many processes involved in growth including glucose uptake, glycogen and triglyceride formation, whereas catecholamines are mainly catabolic.

Although insulin and catecholamines normally have opposing effects, it has been shown that they have similar actions on glucose uptake in skeletal muscle (Nevzorova et al., *Br. J. Pharmacol*, 137, 9, (2002)). In particular, it has been reported that catecholamines stimulate glucose uptake via adrenergic receptors (Nevzorova et al., *Br. J. Pharmacol*, 147, 446, (2006); Hutchinson, Bengtsson *Endocrinology* 146, 901, (2005)) to supply muscle cells with an energy-rich substrate. Thus it is likely that in mammals, including humans, the adrenergic and the insulin systems can work independently to regulate the energy needs of skeletal muscle in different situations. Since insulin also stimulates many anabolic processes, including some that promote undesired effects such as stimulation of lipid incorporation into tissues, leading to e.g. obesity, it would be beneficial to be able to stimulate glucose uptake by other means; for example, by stimulation of the adrenergic receptors (ARs).

All ARs are G protein-coupled receptors (GPCRs) located in the cell membrane and characterized by an extracellular N-terminus, followed by seven transmembrane α-helices (TM-1 to TM-7) connected by three intracellular (IL-1 to IL-3) and three extracellular loops (EL-1 to EL-3), and finally an intracellular C-terminus. There are three different classes of ARs, with distinct expression patterns and pharmacological profiles: $\alpha_1$-, $\alpha_2$- and β-ARs. The $\alpha_1$-ARs comprise the $\alpha_{1A}$, $\alpha_{1B}$ and $\alpha_{1D}$ subtypes while $\alpha_2$-ARs are divided into $\alpha_{2A}$, $\alpha_{2B}$ and $\alpha_{2C}$. The β-ARs are also divided into the subtypes $\beta_1$, $\beta_2$, and $\beta_3$, of which $\beta_2$-AR is the major isoform in skeletal muscle cells. ARs are G protein coupled receptors (GPCRs) that signal through classical secondary messengers such as cyclic adenosine monophosphate (cAMP) and phospholipase C (PLC).

Many effects occurring downstream of ARs in skeletal muscles have been attributed to classical secondary messenger signalling, such as increase in cAMP levels, PLC activity and calcium levels. Stimulation involving the classical secondary messengers has many effects in different tissues. For example, it increases heart rate, blood flow, airflow in lungs and release of glucose from the liver, which all can be detrimental or be considered unwanted side effects if stimulation of ARs should be considered as a type 2 diabetes treatment. Adverse effects of classical AR agonists are, for example, tachycardia, palpitation, tremor, sweats, agitation and increased glucose levels in the blood (glucose output from the liver). It would thus be beneficial to be able to activate ARs without activating these classical secondary messengers, such as cAMP, to increase glucose uptake in peripheral tissues without stimulating the unwanted side effects.

Glucose uptake is mainly stimulated via facilitative glucose transporters (GLUT) that mediate glucose uptake into most cells. GLUTs are transporter proteins that mediate transport of glucose and/or fructose over the plasma membrane down the concentration gradient. There are fourteen known members of the GLUT family, named GLUT1-14, divided into three classes (Class I, Class II and Class III) dependent on their substrate specificity and tissue expression. GLUT1 and GLUT4 are the most intensively studied isoforms and, together with GLUT2 and GLUT3, belong to Class I which mainly transports glucose (in contrast to Class II that also transports fructose). GLUT1 is ubiquitously expressed and is responsible for basal glucose transport. GLUT4 is only expressed in peripheral tissues such as skeletal muscle, cardiac muscle and adipose tissues. GLUT4 has also been reported to be expressed in, for example, the brain, kidney, and liver. GLUT4 is the major isoform involved in insulin stimulated glucose uptake. The mechanism whereby insulin signalling increases glucose uptake is mainly via GLUT4 translocation from intracellular storage to the plasma membrane. It is known that GLUT4 translocation is induced by stimulation of the $\beta_2$-adrenergic receptor.

Thus, a possible treatment of a condition involving dysregulation of glucose homeostasis or glucose uptake in a mammal, such as type 2 diabetes, would involve the activation of the $\beta_2$-adrenergic receptor leading to GLUT4 translocation to the plasma membrane and promotion of glucose uptake into skeletal muscle leading to normalization of whole body glucose homeostasis. In addition, it would be advantageous if the treatment does not involve signalling through cAMP, as this would lead to a favourable side-effect profile.

WO 99/65308 describes various 5,5-dimethylpyrrolidines as components of compositions for use in non-therapeutic methods for deterring vermin.

DESCRIPTION OF THE INVENTION

We have now surprisingly found that certain heteroaryl (heterocyclyl)methanols acting as agonists at the $\beta_2$-adrenergic receptor increase glucose uptake in skeletal muscle.

In addition, we have found that this effect is not mediated through significant cAMP release, such that many of the commonly described side effects seen with traditional $\beta_2$-adrenergic agonists (e.g. tachycardia, palpitation, tremor, sweats, agitation, and the like) can be reduced.

The use of such compounds in medicine provides a means for the treatment of conditions characterized by high blood sugar levels (i.e. hyperglycaemia), such as type 2 diabetes.

Compounds of the Invention

In a first aspect of the invention, there is provided a compound of formula I

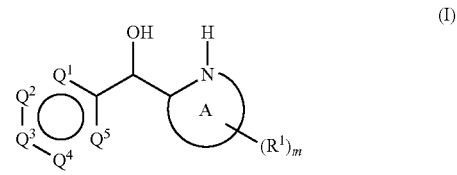

(I)

or a pharmaceutically acceptable salt thereof, wherein:
ring A represents a 4- to 8-membered heterocycloalkyl;
each $R^1$ independently represents $C_{1-6}$ alkyl optionally substituted by one or more halo;
any two $R^1$ groups when attached to the same carbon may form together a 3- to 6-membered ring, which is optionally substituted by one or more groups independently selected from halo and $C_{1-6}$ alkyl optionally substituted by one more halo;

m represents 0 to 13, as appropriate;

the ring comprising $Q^1$ to $Q^5$ represents a 5- or 6-membered heteroaryl optionally substituted with one or more $X^1$;

each $X^1$ independently represents, as appropriate, halo, $R^a$, —CN, —N$_3$, —N(R$^b$)R$^c$, —NO$_2$, —ONO$_2$, —OR$^d$, —S(O)$_p$R$^e$ or —S(O)$_q$N(R$^f$)R$^g$;

$R^a$ represents $C_{1-6}$ alkyl optionally substituted by one or more groups independently selected from $G^1$;

each $R^b$, $R^c$, $R^d$, $R^e$, $R^f$ and $R^g$ independently represents H or $C_{1-6}$ alkyl optionally substituted by one or more groups independently selected from $G^2$;

or alternatively any of $R^b$ and $R^c$ and/or $R^f$ and $R^g$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl optionally substituted by one or more halo, and =O;

$G^1$ and $G^2$ represents halo, —CN, —N(R$^{a1}$)R$^{b1}$, —OR$^{c1}$, —S(O)$_p$R$^{d1}$, —S(O)$_q$N(R$^{e1}$)R$^{f1}$ or =O;

each $R^{a1}$, $R^{b1}$, $R^{c1}$, $R^{d1}$, $R^{e1}$ and $R^{f1}$ independently represents H or $C_{1-6}$ alkyl optionally substituted by one or more halo;

or alternatively any of $R^{a1}$ and $R^{b1}$ and/or $R^{e1}$ and $R^{f1}$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl optionally substituted by one or more halo, and =O;

each p independently represents 0, 1 or 2; and each q independently represents 1 or 2, which compounds (including pharmaceutically acceptable salts) may be referred to herein as "compounds of the invention".

For the avoidance of doubt, the skilled person will understand that references herein to compounds of particular aspects of the invention (such as the first aspect of the invention, e.g. compounds of formula I) will include references to all embodiments and particular features thereof, which embodiments and particular features may be taken in combination to form further embodiments.

Unless indicated otherwise, all technical and scientific terms used herein have the same meaning as commonly understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, edisylate, ethanesulphonate, propanesulphonate, hydroxy-ethane-sulphonate, 1- or 2-naphthalene-sulphonate or 1,5-naphthalene-disulphonate salts) or sulphate, pyrosulphate, bisulphate, sulphite, bisulphite, phosphate, monohydrogen-phosphate, dihydrogenphosphate, metaphosphate, pyrophosphate or nitrate salts, and the like.

Particular acid addition salts that may be mentioned include acetate, bisulphate, fumarate, hydrobromide, hydrochloride, maleate and sulphate salts.

More particular acid addition salts that may be mentioned include bisulphate, hydrochloride and maleate salts.

For the avoidance of doubt, the skilled person will understand that acid addition salts may include diacid salts (e.g. dihydrochloride salts).

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the first aspect of the invention may exist as solids, and thus the scope of the invention includes all amorphous, crystalline and part crystalline forms thereof, and may also exist as oils. Where compounds of the first aspect of the invention exist in crystalline and part crystalline forms, such forms may include solvates, which are included in the scope of the invention. Compounds of the first aspect of the invention may also exist in solution.

Compounds of the first aspect of the invention may contain double bonds and may thus exist as E (entgegen) and Z (zusammen) geometric isomers about each individual double bond. All such isomers and mixtures thereof are included within the scope of the invention.

Compounds of the first aspect of the invention may also exhibit tautomerism. All tautomeric forms and mixtures thereof are included within the scope of the invention. For example, a compound of the first aspect of the invention may be one wherein $Q^1$, $Q^2$ and $Q^5$ represent C—H, $Q^4$ represents N and $Q^3$ represents C—OH (i.e. C substituted with $X^1$ wherein $X^1$ represents OH). In such instances the skilled person will understand that such a compound may exist in the 2-hydroxypyridine form (compound A) or in the 2-pyridone form (compound B), as depicted below.

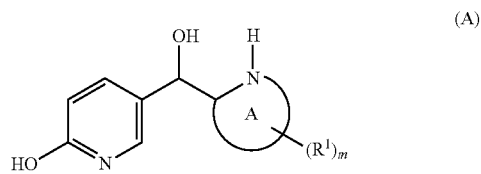

(A)

(B)

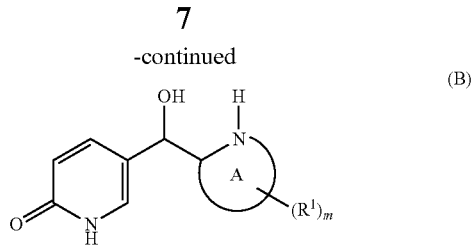

Compounds of the first aspect of the invention may also contain more than one asymmetric carbon atoms and may therefore exhibit optical and/or diastereoisomerism. Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired optical isomers may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution); for example, with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

As used herein, references to halo and/or halogen groups will each independently refer to fluoro, chloro, bromo and iodo (for example, fluoro (F) and chloro (Cl), such as F).

Unless otherwise specified, $C_{1-z}$ alkyl groups (where z is the upper limit of the range) defined herein may be straight-chain or, when there is a sufficient number (i.e. a minimum of three) of carbon atoms, be branched-chain, and/or cyclic (so forming a $C_{3-z}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. When there is a sufficient number of carbon atoms, such groups may also be multicyclic (e.g. bicyclic or tricyclic) or spirocyclic. Such alkyl groups may also be saturated or, when there is a sufficient number (i.e. a minimum of two) of carbon atoms, be unsaturated (forming, for example, a $C_{2-z}$ alkenyl or a $C_{2-z}$ alkynyl group). Particular alkyl groups that may be mentioned include saturated alkyl groups.

As described herein, the ring comprising $Q^1$ to $Q^5$ (which may be referred to as ring Q) represents a 5- or 6-membered heteroaryl optionally substituted with one or more X.

As such, the skilled person will understand that representing $Q^1$ to $Q^5$ the ring will comprise, in addition to carbon atoms, one or more heteroatom, so as to form suitable heteroaryl groups as known to those skilled in the art. Moreover, the skilled person will understand that where the ring containing $Q^1$ to $Q^5$ is 5-membered, one of $Q^1$ to $Q^5$ (e.g. $Q^5$) will represent a direct bond (i.e. that group will not be present).

For the avoidance of doubt, the depiction of the ring containing the $Q^1$ to $Q^5$ groups with a circle therein (for example, as in formula I) will be understood to indicate that the ring is aromatic.

Various heteroaryl groups will be well-known to those skilled in the art, such as pyridinyl, pyridonyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl and the like. The oxides of heteroaryl/heteroaromatic groups are also embraced within the scope of the invention (e.g. the N-oxide).

In particular, the term heteroaryl (or heteroaromatic) includes references to 5-membered or 6-membered heteroaromatic groups containing at least one N atom and optionally one additional heteroatoms selected (e.g. from oxygen, nitrogen and/or sulfur). Particular heteroaryl groups that may be mentioned include those comprising, in the heteroaryl ring, at least one N atom (e.g. one N atom).

Particular heteroaryl groups (e.g. representing ring Q) that may be mentioned include thiazolyl (e.g. thiazol-4-yl and thiazol-5-yl, also thiazol-2-yl), pyrazinyl, pyridazinyl (e.g. pyridazin-3-yl or pyridazin-4-yl, pyrimidinyl (e.g. pyrimidin-4-yl or pyrimidin-5-yl) and pyridonyl (e.g. pyridon-4-yl or pyridon-5-yl). For the avoidance of doubt, the skilled person will understand that pyridonyl groups may exist as the aromatic tautomers thereof, i.e. as hydroxy pyridinyl groups.

In particular, heteroaryl groups (e.g. representing ring Q) that may be mentioned include pyridin-3-yl.

As will be understood by those skilled in the art, substituents on heteroaryl groups (e.g. groups representing $X^1$) may, as appropriate, be located on any atom in the ring system, including a heteroatom (i.e. a N atom). In such circumstances, the skilled person will understand that reference to the substituent being present "as appropriate" will indicate that certain substituents may only be present in positions wherein the presence of such a substituent is chemically allowable, as understood by those skilled in the art.

For example, where $X^1$ is present on a N atom (in which case, it may be referred to as $X^{1a}$), particular $X^1$ groups that may be mentioned include $R^a$. Similarly, where $X^1$ is present on a C atom (in which case, it may be referred to as $X^{1b}$), each $X^1$ may independently represent halo, $R^a$, —CN, —N$_3$, —N(R$^b$)R$^c$, —NO$_2$, —ONO$_2$, —OR$^d$, —S(O)$_p$R$^e$ or —S(O)$_q$ N(R$^f$)R$^g$.

For the avoidance of doubt, the skilled person will understand that the identities of $Q^1$ to $Q^5$ will be selected such that the resulting heteroaryl is a suitable heteroaryl as known to those skilled in the art. For example, in certain instances, where the Q containing ring is a 5-membered ring, one of $Q^1$ to $Q^5$ will represent a direct bond.

Similarly, the skilled person will understand that in 5-membered heteroaryl rings there can only be one O or S, but up to four N atoms (with up to four heteroatoms in total), which may be present as N or NX$^{1a}$ (particularly, with up to one being present as NX$^{1a}$ and the remainder being present as N), as appropriate. Similarly, in a 6-membered heteroaryl ring there will be no O or S present in the ring but up to four (e.g. one or two) N atoms, which will be present as N.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulphur (in particular, oxygen, nitrogen and sulphur).

For the avoidance of doubt, references to polycyclic (e.g. bicyclic or tricyclic) groups (e.g. when employed in the context of cycloalkyl groups) will refer to ring systems wherein at least two scissions would be required to convert such rings into a straight chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, and may also refer to groups in which two non-adjacent atoms are linked by an alkylene group, which later groups may be referred to as bridged.

For the avoidance of doubt, ring A, as described in compounds of formula I, contains an essential nitrogen atom and an essential carbon atom, as represented in the 2-position of ring A (i.e. in the position alpha to both the essential nitrogen atom of the A ring and the carbon bearing the essential —OH group).

For the avoidance of doubt, ring A may be substituted by a number of $R^1$ groups, as defined herein, which number is defined by m, as defined herein. The skilled person will understand that the (maximum) number and position of such substituents will be dictated by the nature of the heterocyclic ring, such as by the size of the ring and the number and type of heteroatoms comprised therein. Thus, where m is defined as 0 to 9, it will be understood that the value 9 represents a theoretical maximum when considering the heterocyclic rings that may be present as ring A, and that for certain heterocyclic groups representing ring A the actual maximum value for m may be lower, as will be readily determined by the skilled person. Moreover, the skilled person will understand that such substituents may be present on suitable moieties comprised within ring A, such as C (carbon) moieties and secondary N (nitrogen) moieties.

In particular, ring A as defined herein may comprise one or two heteroatoms (including the essential NH moiety), which may be selected (in addition to the essential NH moiety) from O, S and N (e.g. O and N, such as N). For example, in addition to the essential NH moiety, ring A as defined herein may comprise up to one additional heteroatom, which may be selected from O, S and N (e.g. O and N, such as N). Thus, for the avoidance of doubt, in particular embodiments ring A will be understood to contain one heteroatom which is the essential N atom.

In particular, ring A as defined herein may be 4- to 7-membered. For example, ring A as defined herein may be 4- to 7-membered comprising one or two (or one, two or three) heteroatoms (i.e. a 4-membered ring may comprise up to one heteroatom, a 5- or 6-membered ring may comprise up to 1 or 2 heteroatoms and a 7-membered ring may comprise 1 or 2, or 1, 2 or 3 heteroatoms), which may be selected from O, S and N (e.g. O and N, such as N).

More particularly, ring A as defined herein may be 5- or 6-membered. For example, ring A as defined herein may be 5- or 6-membered comprising one or two heteroatoms (i.e. up to one additional heteroatom, such as when ring A comprises one heteroatom), which may be selected from O, S and N (e.g. O and N, particularly N).

Alternatively, ring A as defined herein may be 4-membered. For example, ring A as defined herein may be a 4-membered comprising one heteroatom which is the essential N atom.

More particularly, ring A as defined herein may be a 7-membered. For example, ring A as defined herein may be a 7-membered comprising one or two heteroatoms (i.e. up to one additional heteroatom, such as when ring A comprises one heteroatom), which may be selected from O, S and N (e.g. O and N, particularly N).

Particular heterocycloalkyl groups that may be mentioned (e.g. in relation to ring A as defined for compounds of formula I, including all embodiments thereof) include azetidinyl (e.g. azetidine-2-yl, wherein position 1 is the N atom), pyrrolidinyl (e.g. pyrrolidine-2yl), piperidinyl (e.g. piperidin-2-yl) and azepanyl (e.g. azepan-2-yl).

More particular heterocycloalkyl groups that may be mentioned include pyrrolidinyl (e.g. pyrrolidine-2-yl) and piperidinyl (e.g. piperidin-2-yl).

More particular heterocyloalkyl groups that may be mentioned included azetidinyl (e.g. azetidine-2-yl) and azepanyl (e.g. azepan-2-yl).

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more $X^1$ groups are present, those $X^1$ groups may be the same or different. Similarly, where two or more $X^1$ groups are present and each represent halo, the halo groups in question may be the same or different. Likewise, when more than one $R^a$ is present and each independently represents $C_{1-6}$ alkyl substituted by one or more $G^1$ group, the identities of each $G^1$ group are in no way interdependent.

The skilled person will appreciate that compounds of the invention that are the subject of this invention include those that are stable. That is, compounds of the invention include those that are sufficiently robust to survive isolation, e.g. from a reaction mixture.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

In a particular embodiment of the first aspect of the invention, the compound of formula I is not a compound selected from the list consisting of:

(1) (R*)—((S*)-5,5-dimethylpyrrolidin-2-yl)(pyridin-4-yl)methanol
(2) (R*)—((R*)-5,5-dimethylpyrrolidin-2-yl)(pyridin-4-yl)methanol
(3) (5-cyclopropylpyrrolidin-2-yl)(pyrimidin-5-yl)methanol
(4) (5-cyclopropylpyrrolidin-2-yl)(pyrazin-2-yl)methanol The skilled person will understand that chiral centres denoted with an * indicates that the stereochemistry is relative.

In a more particular embodiment of the first aspect of the invention, the compound of formula I is not a compound selected from the list consisting of:

(1) 5,5-dimethylpyrrolidin-2-yl)(pyridin-4-yl)methanol
(2) 5,5-dimethylpyrrolidin-2-yl)(pyridin-4-yl)methanol
(3) (5-cyclopropylpyrrolidin-2-yl)(pyrimidin-5-yl)methanol
(4) (5-cyclopropylpyrrolidin-2-yl)(pyrazin-2-yl)methanol In certain embodiments of the first aspect of the invention, there is provided a compound of formula IA (i.e. the compound of formula I may be a compound of formula IA)

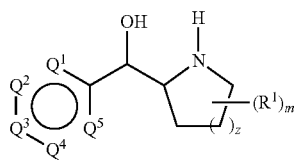

(IA)

or a pharmaceutically acceptable salt thereof, wherein:
R¹ and Q¹ to Q⁵ (i.e. ring Q) are as defined herein; and
z represents 1 to 2; and wherein
when z represents 1 then m represents 0 to 7, or when z represents 2 then m represents 0 to 9.

Further, in certain embodiments of the first aspect of the invention, there is provided a compound of formula IX (i.e. the compound of formula I may be a compound of formula IX)

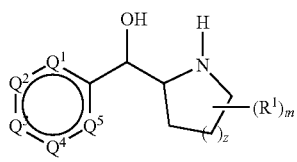

(IX)

or a pharmaceutically acceptable salt thereof, wherein:
R¹ and Q¹ to Q⁵ (i.e. ring Q) are as defined herein; and
z represents 0; and wherein
when z represents 0 then m represents 0 to 5.

Further, in certain embodiments of the first aspect of the invention, there is provided a compound of formula IY (i.e. the compound of formula I may be a compound of formula IY)

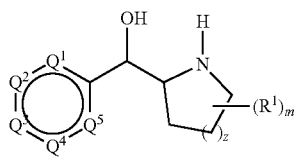

(IY)

or a pharmaceutically acceptable salt thereof, wherein:
R¹ and Q¹ to Q⁵ (i.e. ring Q) are as defined herein; and
z represents 3; and wherein
when z represents 3 then m represents 0 to 11.

For the avoidance of doubt, the skilled person will understand that:
when z represents 0 (i.e. the ring containing the essential nitrogen atom is an azetidine ring), then m may be 0, 1, 2, 3, 4 or 5 (e.g. 0 or 1), such as 1, 2, 3, 4 or 5 (i.e. 1 to 5);
when z represents 1 (i.e the ring containing the essential nitrogen atom is a pyrrolidine ring), then m may be 0, 1, 2, 3, 4, 5, 6 or 7 (e.g. 0 or 1), such as 1, 2, 3, 4, 5, 6 or 7 (i.e. 1 to 7);
when z represents 2 (i.e the ring containing the essential nitrogen atom is a piperidine ring), then m may be 0, 1, 2, 3, 4, 5, 6, 7, 8 or 9 (e.g. 0 or 1), such as 1, 2, 3, 4, 5, 6, 7, 8 or 9 (i.e. 1 to 9); and
when z represents 3 (i.e. the ring containing the essential nitrogen atom is an azepane ring), then m may be 0, 1, 2, 3, 4, 5, 6, 7, 8, 9, 10 or 11 (e.g. 0 or 1), such as 1, 2, 3, 4, 5, 6, 7, 8, 9, 10 or 11 (i.e. 1 to 11).

In certain embodiments, z represents 0.
In certain embodiments, z represents 1.
In certain embodiments, z represents 2.
In certain embodiments, z represents 3.
In certain embodiments, z represents 1 or 2.
In further embodiments, z represents 0 or 3.
In certain embodiments, each $R^1$ represents $C_{1-3}$ alkyl (e.g. methyl, ethyl or n-propyl, such as methyl or n-propyl) optionally substituted by one or more halo.
In certain embodiments: each $R^1$ represents $C_{1-3}$ alkyl (e.g. methyl, ethyl or n-propyl, such as methyl or n-propyl) optionally substituted by one or more halo; and/or m represents 1 or 2.
In certain embodiments: each $R^1$ represents $C_{1-3}$ alkyl (e.g. methyl or n-propyl) optionally substituted by one or more halo; and/or m represents 1.
In particular embodiments, each $R^1$ represents $C_{1-3}$ alkyl (e.g. methyl or n-propyl), m represents 1 and the $R^1$ group is:
where z represents 0, in the 4-position;
where z represents 1, in the 5-position;
where z represents 2, in the 6-position; or
where z represents 3, in the 7-position,
in each case assuming the bond to be essential C—OH group is in the 2-position.
In particular embodiments, each $R^1$ represents $C_{1-3}$ alkyl (e.g. methyl), m represents 2 and both $R^1$ groups are:
where z represents 0, in the 4-position;
where z represents 1, in the 5-position;
where z represents 2, in the 6-position; or
where z represents 3, in the 7-position,
in each case assuming the bond to be essential C—OH group is in the 2-position.
In more particular embodiments, each $R^1$ represents $C_{1-3}$ alkyl (e.g. $C_1$ alkyl, i.e. methyl), and/or m represents 2, and/or both $R^1$ groups are in position-2 (i.e. both $R^1$ groups are one same carbon in ring A). In particular embodiments, each $X^1$ independently represents, as appropriate, halo, $R^a$, —CN, or —$OR^d$.
In more particular embodiments, each $X^1$ independently represents, as appropriate, halo, $C_{1-3}$ alkyl optionally substituted by one or more fluoro, —CN, or —$OR^d$ (e.g. wherein $R^d$ represents H).
In yet more particular embodiments, each $X^1$ independently represents, as appropriate, F, Cl, $C_1$ alkyl (e.g. methyl) optionally substituted by one or more fluoro (e.g. $CF_3$), —CN, or —OH.
In yet more particular embodiments, each $X^1$ independently represents, as appropriate, F or —OH (e.g. F).
In certain embodiments, there are provided compounds of the invention wherein:
any one of $Q^1$ to $Q^5$ represents, as appropriate, O, S, N or $NX^{1a}$, and up to three (e.g. up to one) more of $Q^1$ to $Q^5$ may represent N,
wherein the remainder of $Q^1$ to $Q^5$ each represent $CX^{1b}$, or alternatively $Q^5$ may represent a direct bond;
each $X^{1a}$, where present, independently represents H or $R^a$;
each $X^{1b}$ independently represents H, halo, $R^a$, —CN, —$N_3$, —$N(R^b)R^c$, —$NO_2$, —$ONO_2$, —$OR^d$, —$S(O)_pR^e$ or —$S(O)_qN(R^f)R^g$.
Particular $X^{1b}$ groups that may be mentioned include H and particular $X^1$ groups as described herein.
In more particular such embodiments, wherein the ring comprising $Q^1$ to $Q^5$ represents a 6-membered heteroaryl:

any one to four (e.g. one or two, particularly one) of $Q^1$ to $Q^5$ represents N,
and the remainder of $Q^1$ to $Q^5$ represent $CX^{1b}$.
Thus, in particular embodiments:
any one to four (e.g. one or two, such as one) of $Q^1$ to $Q^5$ represents N,
and the remainder of $Q^1$ to $Q^5$ each represent $CX^1b$ (e.g. wherein at least one $X^{1b}$ represents other than H).

Particular heteroaryl groups that may be mentioned are those comprising at least one N atom. More particular heteroaryl groups that may be mentioned are those wherein one of $Q^1$ to $Q^5$ represents N (e.g. $Q^2$ or $Q^4$ represents N) and the remainder of $Q^1$ to $Q^5$ represents $CX^{1b}$.

In particular embodiments, each $X^{1a}$, were present, represents H.

In certain embodiments, there is provided a compound of the invention wherein each $X^{1b}$ independently represents H, halo, OH, —$NH_2$, CN, or $CF_3$.

In particular embodiments, each $X^{1b}$ independently represents H, OH or halo (e.g. Cl or F, such as F), particularly H or F.

In more particular embodiments, there is at least one $X^{1b}$ independently represents OH or F (e.g. F) and the remaining $X^{1b}$ groups represent H.

In more particular embodiments, there is at least one $X^{1b}$ that represents Cl or F, in particular F, and the remaining $X^{1b}$ groups each represent H.

In more particular embodiments, one $X^{1b}$ represents F and the remaining $X^{1b}$ groups represent H.

For the avoidance of doubt, the skilled person will understand that groups representing $Q^1$ to $Q^5$ may be depicted in relation to compounds of formula I without departing from the teaching of the invention.

In more particular embodiments, there is provided a compound of formula IB

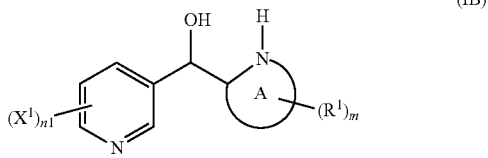

(IB)

or a pharmaceutically acceptable salt thereof, wherein:
ring A, $R^1$, $X^1$ and m are as defined herein; and
n1 represents 0 to 4.

In particular embodiments, n1 represents 0 or 1 (e.g. 1).

Thus, in more particular embodiments, the compound of formula I is a compound of formula IB.

The skilled person will understand that particular Q groups (and the positions and number thereof, such as may correspond to $Q^1$ to $Q^5$ groups in compounds of formula I, provided that at least one of the $Q^1$ to $Q^5$ represent N) that may be mentioned include those present in the examples provided herein.

In a more particular embodiments, there is provided a compound of formula IC

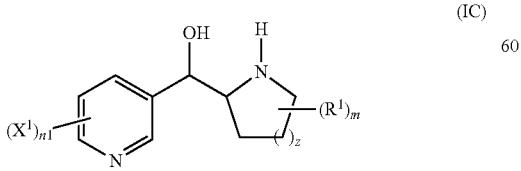

(IC)

or a pharmaceutically acceptable salt thereof, wherein:
$R^1$, $X^1$, m, n1 and z are as defined herein.

In more particular embodiments, there is provided a compound of formula ID

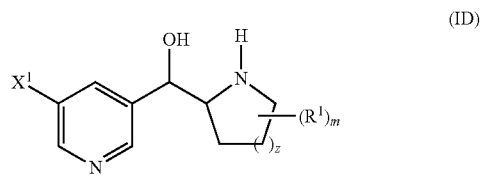

(ID)

or a pharmaceutically acceptable salt thereof, wherein:
$R^1$, $X^1$, m and z are as defined herein.

In a particular embodiment, for compounds of formula I to ID, $X^1$ represents halo, $R^a$, —CN, —$N_3$, —$N(R^b)R^c$, —$NO_2$, —$ONO_2$, —$OR^d$, —$S(O)_pR^e$ or —$S(O)_qN(R^f)R^g$.

In a more particular embodiment, for compounds of formula I to ID, $X^1$ represents OH, Cl and F.

In a more particular embodiment, for compounds of formula I to ID, $X^1$ represents F.

In certain embodiments, m represents 1 or 2.

In certain embodiments, each $R^1$ group independently represents $C_{1-3}$ alkyl (e.g. methyl, ethyl, n-propyl, such as methyl or n-propyl) optionally substituted by one or more halo.

In a further embodiment, when m represents 1, $R^1$ represents $C_1$ alkyl (e.g. methyl) optionally substituted by one or more halo.

In a particular embodiment, when m represents 1, $R^1$ represents $C_3$ alkyl (e.g. n-propyl) optionally substituted by one or more halo.

In a further embodiment, when m represents 2 and each $R^1$ represents $C_{1-3}$ alkyl (e.g. methyl, ethyl, n-propyl, such as methyl or n-propyl) optionally substituted by one or more halo, wherein each $R^1$ group is situated on the same carbon atom.

In a further embodiment, when m represents 2, each $R^1$ represents $C_1$ alkyl (e.g. methyl) optionally substituted by one or more halo, wherein each $R^1$ group is situated on the same carbon atom.

In a further embodiment, when m represents 2, each $R^1$ represents $C_3$ alkyl (e.g. n-propyl) optionally substituted by one or more halo, wherein each $R^1$ group is situated on the same carbon atom.

In certain embodiments, when m represents 1 or 2 (such as in the embodiments referred to herein above), each $R^1$ group is:
where z represents 0, in the 4-position;
where z represents 1, in the 5-position;
where z represents 2, in the 6-position, or
where z represents 3, in the 7-position,
assuming the bond to be essential C—OH group is in the 2-position.

For the avoidance of doubt, in particular embodiments the fragment forming ring A may be represented as follows:

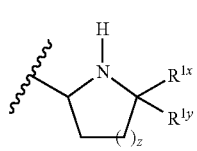

wherein:

z is as defined herein; and either
one of $R^{1x}$ and $R^{1y}$ represents an $R^1$ group (e.g. n-propyl) and the other represents H, or both of $R^{1x}$ and $R^{1y}$ represent an $R^1$ group (e.g. methyl).

In further embodiments the fragment forming ring A may be represented as follows:

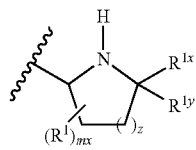

wherein:
z is as defined herein; either
one of $R^{1x}$ and $R^{1y}$ represents an $R^1$ group (e.g. n-propyl) and the other represents H, or both of $R^{1x}$ and $R^{1y}$ represent an $R^1$ group (e.g. methyl);
$R^1$ is as defined herein; and
where $R^{1x}$ and $R^{1y}$ represents an $R^1$ group and the other represents H, then mx represents m as defined herein but wherein the upper limit of mx is one less than the upper limit of m, and
where both of $R^{1x}$ and $R^{1y}$ represent an $R^1$ group, then mx represents m as defined herein but wherein the upper limit of mx is two less than the upper limit of m.

Particular compounds of the first aspect of the invention that may be mentioned include the compounds of the examples provided herein, and pharmaceutically acceptable salts thereof. For the avoidance of doubt, compounds of the examples that are salts may also be provided as the non-salt form or in the form of any (other) pharmaceutically acceptable salt thereof.

For example, compounds of formula I that may be mentioned include:
(1) (R)-(5-Fluoropyridin-3-yl)((2R,6S)-6-propylpiperidin-2-yl)methanol (e.g. (R)-(5-Fluoropyridin-3-yl)((2R,6S)-6-propylpiperidin-2-yl)methanol dihydrochloride);
(2) (S)-(5-Fluoropyridin-3-yl)((2R,6S)-6-propylpiperidin-2-yl)methanol;
(3) (R)-(5-Fluoropyridin-3-yl)((2R,5R)-5-propylpyrrolidin-2-yl)methanol (e.g. (R)-(5-Fluoropyridin-3-yl)((2R,5R)-5-propylpyrrolidin-2-yl)methanol maleate);
(4) (S)-(5-Fluoropyridin-3-yl)((2R,5R)-5-propylpyrrolidin-2-yl)methanol (e.g. (S)-(5-Fluoropyridin-3-yl)((2R,5R)-5-propylpyrrolidin-2-yl)methanol maleate);
(5) (R)-((R)-5,5-Dimethylpyrrolidin-2-yl)(5-fluoropyridin-3-yl)methanol;
(6) (S)-((R)-5,5-Dimethylpyrrolidin-2-yl)(5-fluoropyridin-3-yl)methanol;
(7) (5-((R)-((R)-5,5-dimethylpyrrolidin-2-yl)(hydroxy)methyl)pyridin-3-ol; and
(8) 5-((S)-((R)-5,5-dimethylpyrrolidin-2-yl)(hydroxy)methyl)pyridin-3-ol,
and pharmaceutically acceptable salts thereof.

Further compounds of formula I that may be mentioned include:
(9) (R)-((R)-4,4-Dimethylazetidin-2-yl)(5-fluoropyridin-3-yl)methanol (e.g. (R)-((R)-4,4-Dimethylazetidin-2-yl)(5-fluoropyridin-3-yl)methanol dihydrochloride);
(10) (R)-((S)-4,4-Dimethylazetidin-2-yl)(5-fluoropyridine-3-yl)methanol (e.g. (R)-((S)-4,4-Dimethylazetidin-2-yl)(5-fluoropyridine-3-yl)methanol dihydrochloride);
(11) (S)-((S)-4,4-Dimethylazetidin-2-yl)(5-fluoropyridine-3-yl)methanol ((S)-((S)-4,4-Dimethylazetidin-2-yl)(5-fluoropyridine-3-yl)methanol dihydrochloride);
(12) (S)-((R)-4,4-Dimethylazetidin-2-yl)(5-fluoropyridin-3-yl)methanol (e.g. (S)-((R)-4,4-Dimethylazetidin-2-yl)(5-fluoropyridin-3-yl)methanol dihydrochloride);
(13) (R)-(5-Fluoropyridin-3-yl)((2R,7R)-7-propylazepan-2-yl)methanol;
(14) (S)-(5-Fluoropyridin-3-yl)((2R,7R)-7-propylazepan-2-yl)methanol;
(15) (R)-(5-Fluoropyridin-3-yl)(S,7S)-7-propylazepan-2-yl)methanol (e.g. (R)-(5-Fluoropyridin-3-yl)(S,7S)-7-propylazepan-2-yl)methanol dihydrochloride); and
(16) (S)-(5-Fluoropyridin-3-yl)(S,7S)-7-propylazepan-2-yl)methanol,
and pharmaceutically acceptable salts thereof.

In particular, compounds of formula I that may be mentioned include:
(a) (R)-(5-Fluoropyridin-3-yl)((2R,5R)-5-propylpyrrolidin-2-yl)methanol maleate (e.g. (R)-(5-Fluoropyridin-3-yl)((2R,5R)-5-propylpyrrolidin-2-yl)methanol maleate); and/or
(b) (R)-((R)-5,5-Dimethylpyrrolidin-2-yl)(5-fluoropyridin-3-yl)methanol,
and pharmaceutically acceptable salts thereof.

As described herein, compounds of the first aspect of the invention may also contain one or more asymmetric carbon atoms and may therefore exhibit optical and/or diastereoisomerism. Moreover, it has been found that certain such optical and/or diastereoisomers may show increased utility in the treatment of hyperglycaemia or disorders characterized by hyperglycaemia (such as type 2 diabetes), as described herein.

In a certain embodiments of the first aspect of the invention, the right-hand side of the compound may be depicted as follows

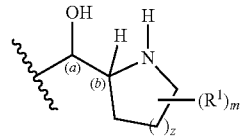

wherein the carbon substituted with the essential —OH group (denoted with (a)) is chiral and may be in either the (R) or (S) configuration, and the carbon beta to the hydroxy group and adjoined to ring A (denoted with (b)) is chiral and may be in either the (R) or (S) configuration.

In a particular embodiment, wherein z represents 0 (in which case, the skilled person will understand that ring A is azetidin-2-yl), carbon (a) is in the (R) configuration.

In a particular embodiment, wherein z represents 0, carbon (a) is in the (R) configuration and carbon (b) is in the (R) configuration.

In a particular embodiment, wherein z represents 1 (in which case, the skilled person will understand that ring A is pyrrolidin-2-yl), carbon (a) is in the (R) configuration.

In a particular embodiment, wherein z represents 1, carbon (a) is in the (R) configuration and carbon (b) is in the (R) configuration.

In a further embodiment, wherein z represents 2 (in which case ring A is piperidin-2-yl), carbon (a) is in the (S) configuration.

In a more particular embodiment, wherein z represents 2, and carbon (a) is in the (S) configuration and carbon (b) is in the (R) configuration.

In a particular embodiment, wherein z represents 3 (in which case, the skilled person will understand that ring A is azepan-2-yl), carbon (a) is in the (S) configuration.

In a particular embodiment, wherein z represents 1, compounds of formula IA may be depicted as $IA^1$ and $IA^2$

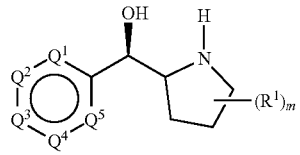
(IA$^1$)

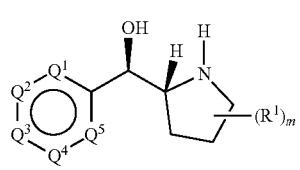
(IA$^2$)

In a particular embodiment, wherein z represents 2, compounds of formula IA may be depicted as $IA^3$ and $IA^4$

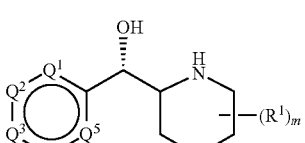
(IA$^3$)

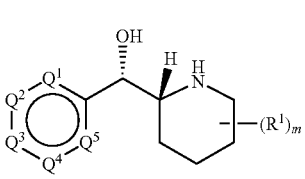
(IA$^4$)

In a particular embodiment, wherein z represents 0, compounds of formula IX may be depicted as $IX^1$ and $IX^2$

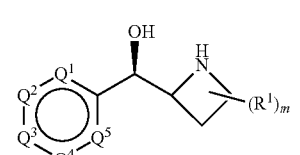
(IX$^1$)

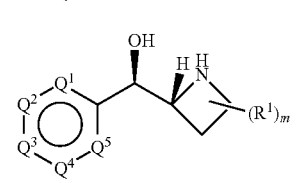
(IX$^2$)

In a particular embodiment, wherein z represents 3, compounds of formula IY may be depicted as $IY^3$ and $IY^4$

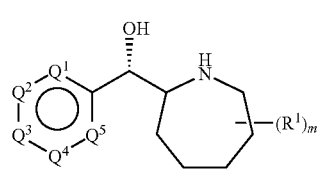
(IY$^3$)

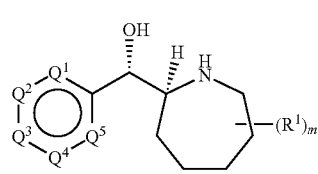
(IY$^4$)

In a particular embodiment, wherein z represents 1, compounds of formula IC may be depicted as $IC^1$ and $IC^2$

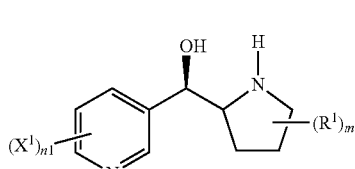
(IC$^1$)

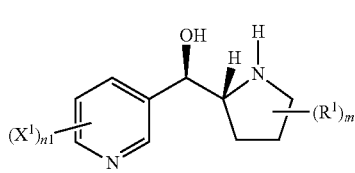
(IC$^2$)

In a particular embodiment, wherein z represents 2, compounds of formula IC may be depicted as $IC^3$ and $IC^4$

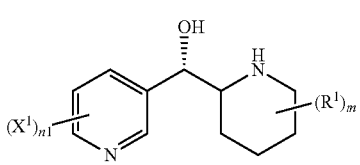
(IC$^3$)

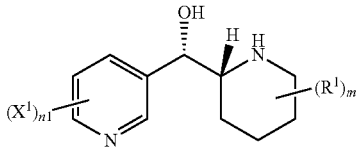
(IC$^4$)

In a particular embodiment, wherein z represents 0, compounds of formula IC may be depicted as $IC^5$ and $IC^6$

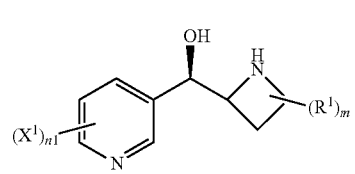
(IC$^5$)

-continued (IC⁶)

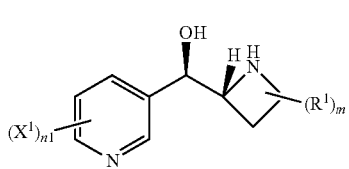

In a particular embodiment, wherein z represents 3, compounds of formula IC may be depicted as IC⁷ and IC⁸

(IC⁷)

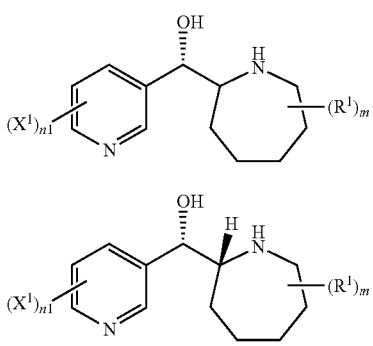

(IC⁸)

In a particular embodiment, wherein z represents 1, compounds of formula ID may be depicted as ID¹ and ID²

(ID¹)

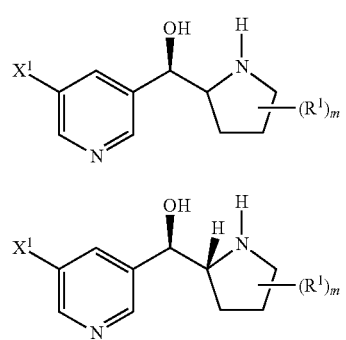

(ID²)

In a particular embodiment, wherein z represents 2, compounds of formula ID may be depicted as ID³ and ID⁴

(ID³)

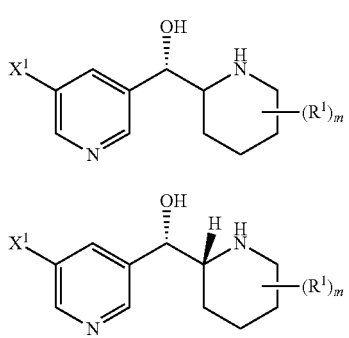

(ID⁴)

In a particular embodiment, wherein z represents 0, compounds of formula ID may be depicted as ID⁵ and ID⁶

(ID⁵)

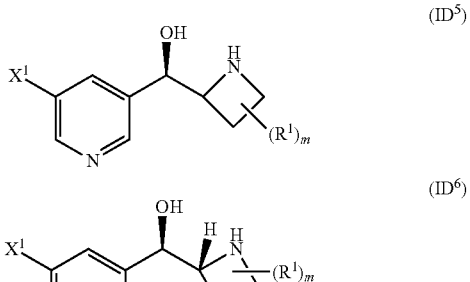

(ID⁶)

In a particular embodiment, wherein z represents 3, compounds of formula ID may be depicted as ID⁷ and ID⁸

(ID⁷)

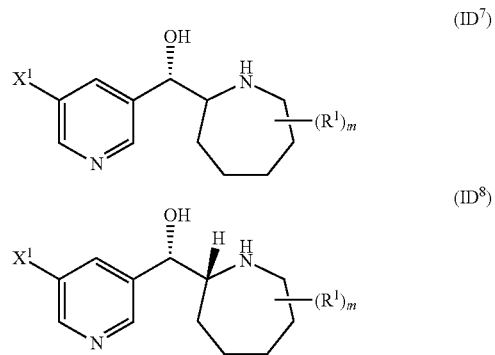

(ID⁸)

For the avoidance of doubt, compounds depicted herein as having a certain stereochemistry may also be depicted with the relevant stereochemistry labelled. For example, compounds of formula ID⁴ may be depicted as:

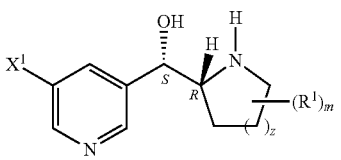

The skilled person will understand that where compounds of the invention are referred to as having specific stereochemistry, that compound is provided in the substantial absence of other stereoisomers.

As used herein, references to the substantial absence of other stereoisomer will refer to the desired stereoisomers (e.g. in the case of compounds of formula IA, when the carbon (a) is in the (R) configuration) being present at a purity of at least 80% (e.g. at least 90%, such as at least 95%) relative to the opposite stereoisomer (e.g. in the case of compounds of formula I, when the carbon (b) is in the (S) configuration). Alternatively, in such instances, compounds may be indicated to be present in the substantial absence of the compound in the other configurations (i.e. for example, the (S) configuration), which may indicate that the compound in the relevant configuration is present in an enantiomeric excess (e.e.) or diastereomeric excess (d.e.) of at least 90% (such as at least 95%, at least 98% or, particularly, at least 99%, for example at least 99.9%).

For the avoidance of doubt, compounds referred to as having a specific stereochemistry at a defined position (e.g. in the case of compounds of formula I, the carbon (a) in the (R) or (S) configuration) may also have stereochemistry at one or more other positions, and so may exist as mixtures of enantiomers or diastereoisomers in relation to the stereochemistry at those positions.

The skilled person will understand that compounds of the invention are agonists of the $\beta_2$-adrenergic receptor. In particular embodiments, such compounds may be identified using techniques known to those skilled in the art, such as the assay described in Biological example 1 herein below, wherein an agonist may be identified as a compound showing activity of more than 25% (e.g. more than 50%, particularly more than 75%) of that of isoproterenol in the same assay.

The skilled person will also understand that compounds of the invention may act without (or with only a minimal effect in) inducing cAMP production. In particular embodiments, such compounds may be identified using techniques known to those skilled in the art, such as the assay described in Biological example 2 herein below, wherein a compound acting without (or with only a minimal effect in) inducing cAMP production may be identified as a compound showing activity of less than 75% (e.g. less than 50%, particularly less than 25%) of that of isoproterenol in the same assay.

Medical Uses

As indicated herein, the compounds of the invention, and therefore compositions and kits comprising the same, are useful as pharmaceuticals.

Thus, according to a second aspect of the invention there is provided a compound of the first aspect of the invention, as hereinbefore defined (i.e. a compound as defined in the first aspect of the invention, including all embodiments and particular features thereof), for use as a pharmaceutical (or for use in medicine).

For the avoidance of doubt, references to compounds as defined in the first aspect of the invention will include references to compounds of formula I (including all embodiments thereof) and pharmaceutically acceptable salts thereof.

As indicated herein, the compounds of the invention may be of particular use in treating hyperglycaemia or a disorder characterized by hyperglycaemia.

Thus, in a third aspect of the invention, there is provided a compound of the first aspect of the invention, as hereinbefore defined, for use in the treatment of hyperglycaemia or a disorder characterized by hyperglycaemia.

In an alternative third aspect of the invention, there is provided the use of a compound of formula I, or a pharmaceutically acceptable salt thereof, in the manufacture of a medicament for use in the treatment of hyperglycaemia or a disorder characterized by hyperglycaemia.

In a further alternative third aspect of the invention, there is provided a method of treating hyperglycaemia or a disorder characterized by hyperglycaemia comprising administering to a patient in need thereof a therapeutically effective amount of a compound of formula I, or a pharmaceutically acceptable salt thereof.

For the avoidance of doubt, the term "hyperglycaemia" as used herein will be understood by those skilled in the art to refer to a condition wherein an excessive amount of glucose circulates in blood plasma of the subject experiencing the same. In particular, it may refer to a subject (e.g a human subject) having blood glucose levels higher than about 10.0 mmol/L (such as higher than about 11.1 mmol/L, e.g. higher than about 15 mmol/L), although it may also refer to a subject (e.g a human subject) having blood glucose levels higher than about 7 mmol/L for an extended period of time (e.g. for greater than 24 hours, such as for greater than 48 hours).

The skilled person will understand that references to the treatment of a particular condition (or, similarly, to treating that condition) take their normal meanings in the field of medicine. In particular, the terms may refer to achieving a reduction in the severity of one or more clinical symptom associated with the condition. For example, in the case of type 2 diabetes, the term may refer to achieving a reduction of blood glucose levels. In particular embodiments, in the case of treating hyperglycaemia or conditions characterised by hyperglycaemia, the term may refer to achieving a reduction of blood glucose levels (for example, to or below about 10.0 mmol/mL (e.g. to levels in the range of from about 4.0 mmol/L to about 10.0 mmol/L), such as to or below about 7.5 mmol/mL (e.g. to levels in the range of from about 4.0 mmol/L to about 7.5 mmol/L) or to or below about 6 mmol/mL (e.g. to levels in the range of from about 4.0 mmol/L to about 6.0 mmol/L)).

As used herein, references to patients will refer to a living subject being treated, including mammalian (e.g. human) patients. Thus, in particular embodiments of the first aspect of the invention, the treatment is in a mammal (e.g. a human).

As used herein, the term therapeutically effective amount will refer to an amount of a compound that confers a therapeutic effect on the treated patient. The effect may be objective (i.e. measurable by some test or marker) or subjective (i.e. the subject gives an indication of and/or feels an effect).

Although compounds of the first aspect of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the first aspect of the invention are included within the scope of the invention.

For the avoidance of doubt, the compounds of the first aspect of the invention are useful because they possess pharmacological activity, and/or are metabolised in the body following oral or parenteral administration to form compounds that possess pharmacological activity. In particular, as described herein, compounds of the first aspect of the invention are useful in the treatment of hyperglycaemia or disorders characterized by hyperglycaemia (such as type 2 diabetes), which terms will be readily understood by one of skill in the art (as described herein).

In a particular embodiment, the treatment is of a disorder (which may also be referred to as a condition or disease) characterised by hyperglycaemia.

In particular embodiments, compounds of the invention (i.e. compounds of formula I, including all embodiments thereof) are for use in the treatment of type 2 diabetes (or useful in the manufacture of a medicament for such treatment, or useful in a method for such treatment, as described herein).

In particular embodiments of the first aspect of the invention, the disorder is type 2 diabetes, such as type 2 diabetes of a sub-type selected from the list consisting of maturity-onset diabetes in the young (MODY), ketosis-prone diabetes in adults, latent autoimmune diabetes of adults (LADA), and gestational diabetes.

In further particular embodiments, the treatment of type 2 diabetes is in a non-obese patient.

For the avoidance of doubt, the skilled person will understand that patients with a Body Mass Index (BMI) of greater than 30 are considered to be obese.

In particular embodiments, the treatment may be of hyperglycaemia in a patient who is at risk of developing type 2 diabetes, which condition may be defined as pre-diabetes. Thus, compounds of the invention may be useful in the prevention of type 2 diabetes (e.g. in a patient having pre-diabetes).

As used herein, the term prevention (and, similarly, preventing) includes references to the prophylaxis of the disease or disorder (and vice-versa). As such, references to prevention may also be references to prophylaxis, and vice versa. In particular, the term may refer to achieving a reduction in the likelihood of the patient (or healthy subject) developing the condition (for example, at least a 10% reduction, such as at least a 20%, 30% or 40% reduction, e.g. at least a 50% reduction).

In more particular embodiments, the type 2 diabetes is characterised by the patient displaying severe insulin resistance (SIR).

In further embodiments, the treatment may be of hyperglycaemia in a patient having type 1 diabetes. Thus, compounds of the invention may be useful in the treatment of hyperglycaemia in type 1 diabetes.

The skilled person will understand that compounds of the invention may be useful in treating hyperglycaemia in patients having impaired insulin production, such as in patients having cystic fibrosis. Thus, in further embodiments, the disorder characterized by hyperglycaemia is cystic fibrosis-related diabetes.

In particular embodiments that may be mentioned, the disorder characterised by hyperglycaemia is (or is characterized by) severe insulin resistance (SIR), which may be understood by those in the art to refer to disorders wherein typically the subject has normal, or in some cases increased, insulin production but significantly reduced insulin sensitivity. In particular instances, such patients may be non-obese (e.g. being of a healthy weight). Thus, in particular embodiments, such treatments are performed in patients who are not defined as being obese (e.g. in patients who are defined as being of a healthy weight).

For example, SIR may be identified in a patient based in said patient having fasting insulin >150 pmol/L and/or a peak insulin on glucose tolerance testing of >1,500 pmol/L, particularly in individuals with a BMI<30 kg/m$^2$ (which patient may otherwise have normal glucose tolerance).

More particularly, SIR may be characterised by the patient having no significant response to the presence of insulin, which may result from a defect (e.g. a genetic defect) in the function of the insulin receptor.

Particular disorders that may be characterised by SIR include: Rabson-Mendenhall syndrome, Donohue's syndrome (leprechaunism), Type A and Type B syndromes of insulin resistance, the HAIR-AN (hyperandrogenism, insulin resistance, and acanthosis nigricans) syndromes, pseudoacromegaly, and lipodystrophy.

More particular disorders that may be characterised by SIR include Donohue's syndrome and Type A syndrome of insulin resistance and, yet more particularly, Rabson-Mendenhall syndrome.

The skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of type 2 diabetes, such as treatment with one or more other therapeutic agent that is useful in the treatment of type 2 diabetes as known to those skilled in the art, such as therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that:
  (i) are capable of reducing blood sugar levels; and/or
  (ii) are insulin sensitizers; and/or
  (iii) enhance insulin release,
all of which are described herein below.

In alternative embodiments, compounds of the first aspect of the invention (i.e. compounds of the invention) may be useful in the treatment of a non-alcoholic fatty liver disease (NAFLD).

Non-alcoholic fatty liver disease (NAFLD) is defined by excessive fat accumulation in the form of triglycerides (steatosis) in the liver (designated as an accumulation of greater than 5% of hepatocytes histologically). It is the most common liver disorder in developed countries (for example, affecting around 30% of US adults) and most patients are asymptomatic. If left untreated, the condition may progressively worsen and may ultimately lead to cirrhosis of the liver. NAFLD is particularly prevalent in obese patients, with around 80% thought to have the disease.

A sub-group of NAFLD patients (for example, between 2 and 5% of US adults) exhibit liver cell injury and inflammation in addition to excessive fat accumulation. This condition, designated as non-alcoholic steatohepatitis (NASH), is virtually indistinguishable histologically from alcoholic steatohepatitis. While the simple steatosis seen in NAFLD does not directly correlate with increased short-term morbidity or mortality, progression of this condition to NASH dramatically increases the risks of cirrhosis, liver failure and hepatocellular carcinoma. Indeed, NASH is now considered to be one of the main causes of cirrhosis (including cryptogenic cirrhosis) in the developed world.

The exact cause of NASH has yet to be elucidated, and it is almost certainly not the same in every patient. It is most closely related to insulin resistance, obesity, and the metabolic syndrome (which includes diseases related to diabetes mellitus type 2, insulin resistance, central (truncal) obesity, hyperlipidaemia, low high-density lipoprotein (HDL) cholesterol, hypertriglyceridemia, and hypertension). However, not all patients with these conditions have NASH, and not all patients with NASH suffer from one of these conditions. Nevertheless, given that NASH is a potentially fatal condition, leading to cirrhosis, liver failure and hepatocellular carcinoma, there exists a clear need for an effective treatment.

In particular embodiments, compounds of the invention (i.e. compounds of formula I, including all embodiments thereof) are for use in the treatment of a non-alcoholic fatty liver disease (or useful in the manufacture of a medicament for such treatment, or useful in a method for such treatment, as described herein).

The process by which the triglyceride fat accumulates in liver cells is called steatosis (i.e. hepatic steatosis). The skilled person will understand that the term "steatosis" encompasses the abnormal retention of fat (i.e. lipids) within a cell. Thus, in particular embodiments of the first aspect of the invention, the treatment or prevention is of a fatty liver disease which is characterized by steatosis.

During steatosis, excess lipids accumulate in vesicles that displace the cytoplasm of the cell. Over time, the vesicles can grow large enough to distort the nucleus, and the condition is known as macrovesicular steatosis. Otherwise, the condition may be referred to as microvesicular steatosis. Steatosis is largely harmless in mild cases; however, large accumulations of fat in the liver can cause significant health issues. Risk factors associated with steatosis include diabetes mellitus, protein malnutrition, hypertension, obesity, anoxia, sleep apnea and the presence of toxins within the cell.

As described herein, fatty liver disease is most commonly associated with alcohol or a metabolic syndrome (for example, diabetes, hypertension, obesity or dyslipidemia). Therefore, depending on the underlying cause, fatty liver disease may be diagnosed as alcohol-related fatty liver disease or non-alcoholic fatty liver disease (NAFLD).

Particular diseases or conditions that are associated with fatty liver disease that are not related to alcohol include metabolic conditions such as diabetes, hypertension, obesity, dyslipidemia, abetalipoproteinemia, glycogen storage diseases, Weber-Christian disease, acute fatty liver of pregnancy, and lipodystrophy. Other non-alcohol related factors related to fatty liver diseases include malnutrition, total parenteral nutrition, severe weight loss, refeeding syndrome, jejunoileal bypass, gastric bypass, polycystic ovary syndrome and diverticulosis.

The compounds of the invention have been found to be particularly useful in the treatment or prevention of NAFLD, which may be referred to as a fatty liver disease which is not alcohol related. A fatty liver disease which is "not alcohol related" may be diagnosed wherein alcohol consumption of the patient is not considered to be a main causative factor. A typical threshold for diagnosing a fatty liver disease as "not alcohol related" is a daily consumption of less than 20 g for female subjects and less than 30 g for male subjects.

If left untreated, subjects suffering from fatty liver disease may begin to experience inflammation of the liver (hepatitis). It has been postulated that one of the possible causes of this inflammation may be lipid peroxidative damage to the membranes of the liver cells. Inflammation of a fatty liver can lead to a number of serious conditions and it is therefore desirable to treat or prevent fatty liver disease before inflammation occurs. Thus, in particular embodiments of the first aspect of the invention, the treatment or prevention is of a NAFLD which is associated with inflammation.

Non-alcoholic steatohepatitis (NASH) is the most aggressive form of NAFLD, and is a condition in which excessive fat accumulation (steatosis) is accompanied by inflammation of the liver. If advanced, NASH can lead to the development of scar tissue in the liver (fibrosis) and, eventually, cirrhosis. As described above, the compounds of the invention have been found to be useful in the treatment or prevention of NAFLD, particularly when accompanied by inflammation of the liver. It follows that the compounds of the invention are also useful in the treatment or prevention of NASH. Therefore, in a further embodiment of the first aspect of the invention, the treatment or prevention is of non-alcoholic steatohepatitis (NASH).

The skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of a fatty liver disease, as described herein, such as treatment with one or more other therapeutic agent that is useful in the treatment of a fatty liver disease as known to those skilled in the art; for example, therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that are capable of reducing the level of fat (e.g. triglycerides) in the liver.

References to treatment of a fatty liver disease may refer to achieving a therapeutically significant reduction of fat (e.g. triglycerides levels) in liver cells (such as a reduction of at least 5% by weight, e.g. a reduction of at least 10%, or at least 20% or even 25%).

Pharmaceutical Compositions

As described herein, compounds of the first aspect of the invention are useful as pharmaceuticals. Such compounds may be administered alone or may be administered by way of known pharmaceutical compositions/formulations.

In a fourth aspect of the invention, there is provided a pharmaceutical composition comprising a compound as defined in the first aspect of the invention (i.e. a compound of the invention), and optionally one or more pharmaceutically acceptable adjuvant, diluent and/or carrier.

The skilled person will understand that references herein to compounds of the first aspect of the invention being for particular uses (and, similarly, to uses and methods of use relating to compounds of the invention) may also apply to pharmaceutical compositions comprising compounds of the invention as described herein.

In a fifth aspect of the invention, there is provided a pharmaceutical composition for use in the treatment of hyperglycaemia or a disorder characterized by hyperglycaemia (as defined herein, such as type 2 diabetes) comprising a compound as defined in the first aspect of the invention, and optionally one or more pharmaceutically acceptable adjuvant, diluent and/or carrier.

In an alternative fifth aspect of the invention, there is provided a pharmaceutical composition for use in the treatment or prevention of a non-alcoholic fatty liver disease, as defined herein.

The skilled person will understand that compounds of the first (and, therefore, second and third) aspect of the invention may act systemically and/or locally (i.e. at a particular site).

The skilled person will understand that compounds and compositions as described in the first to fifth aspects of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form. Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments of the fourth and fifth aspects of the invention, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The skilled person will understand that compounds of the invention, and pharmaceutically-acceptable salts thereof, may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 0.01 µg/kg of body weight per day (µg/kg/day) to about 200 µg/kg/day, preferably about 0.01 to about 10 µg/kg/day, and more preferably about 0.1 to about 5.0 µg/kg/day. For example, when administered orally, treatment with such compounds may comprise administration of a formulations typically containing between about 0.01 µg to about 2000 mg, for example between about 0.1 µg to about 500 mg, or between 1 µg to about 100 mg (e.g. about 20 µg to about 80 mg), of the active ingredient(s). When administered intravenously, the most preferred doses will range from about 0.001 to about 10 µg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 10 mg, 20 mg, 30 mg or 40 mg twice daily, or 10 µg, 20 µg, 30 µg or 40 µg twice daily).

In any event, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

As described herein above, the skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of hyperglycaemia or a disorder characterized by hyperglycaemia (as defined herein, such as type 2 diabetes), such as treatment with one or more other therapeutic agent that is useful in the treatment of hyperglycaemia or a disorder characterized by hyperglycaemia(as defined herein, such as type 2 diabetes).

In particular embodiments of the fourth and fifth aspects of the invention, the pharmaceutical composition may further comprise one or more additional (i.e. other) therapeutic agent.

In more particular embodiments, the one or more additional therapeutic agent is an agent for the treatment of type 2 diabetes as known to those skilled in the art, such as metformin, sulfonylureas (e.g. carbutamide, acetohexamide, chlorpropamide, tolbutamide, glipizide (glucotrol), gliclazide, glibenclamide, glyburide (Micronase), glibornuride, gliquidone, glisoxepide, glyclopyramide, glimepiride (Amaryl), glimiprime, JB253 or JB558), thiazolidinediones (e.g. pioglitazone, rosiglitazone (Avandia), lobeglitazone (Duvie) and troglitazone (Rezulin)), dipeptidyl peptidase-4 inhibitors (e.g. sitagliptin, vildagliptin, saxagliptin, linagliptin, anagliptin, teneligliptin, alogliptin, trelagliptin, gemigliptin, dutogliptin and omarigliptin), SGLT2 inhibitors (e.g. dapagliflozin, empagliflozin, canagliflozin, ipragliflozin, tofogliflozin, sergliflozin etabonate, remogliflozin etabonate, and ertugliflozin), and glucagon-like peptide-1 (GLP-1) analogues (e.g. exenatide, liraglutide, lixisenatide, albiglutide, dulaglutide and semaglutide).

The skilled person will understand that combinations of therapeutic agents may also described as a combination product and/or provided as a kit-of-parts.

In a sixth aspect of the invention, there is provided a combination product comprising:
(A) a compound as defined in the first aspect of the invention; and
(B) one or more additional therapeutic agent,
wherein each of components (A) and (B) is formulated in admixture, optionally with one or more a pharmaceutically-acceptable adjuvant, diluent or carrier.

In a seventh aspect of the invention, there is provided a kit-of-parts comprising:
(a) a compound as defined in the first (or second and/or third) aspect of the invention, (or a pharmaceutical composition comprising the same) or a pharmaceutical composition as defined in the fourth or fifth aspect of the invention; and
(b) one or more other therapeutic agent, optionally in admixture with one or more pharmaceutically-acceptable adjuvant, diluent or carrier,
which components (a) and (b) are each provided in a form that is suitable for administration in conjunction with the other.

In particular embodiments (e.g. of the sixth and seventh aspects of the invention), the additional therapeutic agent is a therapeutic agent that is useful for the treatment of hyperglycaemia or a disorder characterized by hyperglycaemia (e.g. type 2 diabetes), as known to those skilled in the art (such as those described herein).

For example, in particular embodiments of the fourth to fifth aspects of the invention, the additional therapeutic agent is an agent that:
(i) is capable of reducing blood sugar levels; and/or
(ii) is an insulin sensitizer; and/or
(iii) is able to enhance insulin release,
which agents will be readily identified by those skilled in the art and include, in particular, such therapeutic agents that are commercially available (e.g. agents that the subject of a marketing authorization in one or more territory, such as a European or US marketing authorization).

The skilled person will understand that references to therapeutic agents capable of reducing blood glucose levels may refer to compounds capable of reducing levels of blood by at least 10% (such as at least 20%, at least 30% or at least 40%, for example at least 50%, at least 60%, at least 70% or at least 80%, e.g. at least 90%) when compared to the blood glucose levels prior to treatment with the relevant compound.

In alternative embodiments of the sixth and seventh aspects of the invention, the additional therapeutic agent is an agent for the treatment or prevention of a non-alcoholic fatty liver disease (such as NASH), which agents will be readily identified by those skilled in the art and include, in particular, such therapeutic agents that are commercially available (e.g. agents that the subject of a marketing authorization in one or more territory, such as a European or US marketing authorization).

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

In further aspects of the invention, there is provided a process for the preparation of a combination product or kit-of-parts as hereinbefore defined, which process comprises bringing into association a compound of the invention, as hereinbefore defined, or a pharmaceutically acceptable salt thereof with the other therapeutic agent that is useful in the treatment of hyperglycaemia or a disorder characterized by hyperglycaemia (e.g. type 2 diabetes), and at least one pharmaceutically-acceptable adjuvant, diluent or carrier.

As used herein, references to bringing into association will mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds as defined in the first (and, therefore, second and third) aspect of the invention (i.e. compounds of the invention) may be prepared in accordance with techniques that are well known to those skilled in the art, such as those described in the examples provided hereinafter.

For example, there is provided a process for the preparation of a compound of formula I, or a pharmaceutically acceptable salt thereof, as defined in the first aspect of the invention (which may be utilised in the preparation of, for example, a compound as defined in the second aspect of the invention), which process comprises:
(i) reaction of a compound of formula II

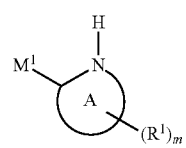

(II)

wherein m, $R^1$ and ring A are as defined herein, and wherein $M^1$ represents a suitable metal or metal halide, with a compound of formula III

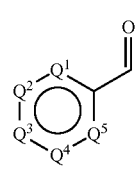

(III)

wherein $Q^1$ to $Q^5$ (and, therefore ring Q) are as defined herein, under conditions known to those skilled in the art;

(ii) reaction of a compound of formula IV

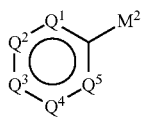
(IV)

wherein $Q^1$ to $Q^5$ are as defined herein, and wherein $M^2$ represents a suitable metal or metal halide, with a compound of formula V

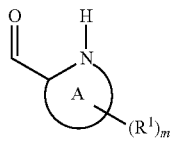
(V)

wherein m, $R^1$ and ring A are as defined herein, under conditions known to those skilled in the art;

(iii) for compounds wherein at least one $X^1$ is present and represents —OH, deprotection of a compound of formula VI

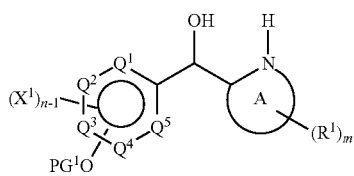
(VI)

wherein $Q^1$ to $Q^5$, ring A, n, m $X^1$ and $R^1$ are as defined hereinabove, $PG^1$ represents a suitable protecting group as known to those skilled in the art (e.g. benzyl) under conditions known to those skilled in the art (for example, in the case of a benzyl protecting group, in the presence of hydrogen and a suitable catalyst or a suitable acid; in the case of alkyl, such as methyl, in the presence of $BBr_3$, HBr or alkyl sulfides);

(iv) for compounds wherein at least one $X^1$ is present and represents —$NH_2$, deprotection of a compound of formula VII

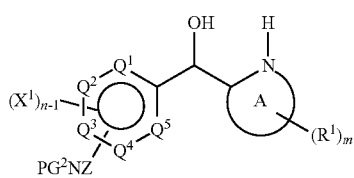
(VII)

wherein $Q^1$ to $Q^5$, ring A, n, m, $X^1$ and $R^1$ are as defined hereinabove, and Z represents H or $PG^3$, wherein $PG^2$ and $PG^3$ each represents a suitable protecting group as known to those skilled in the art (e.g. a carbamate protecting group, such as tert-butyloxycarbonyl (Boc), fluorenylmethyloxycarbonyl (Fmoc) or carboxybenzyl (Cbz), or an amide protecting group, such as acetyl and benzoyl), under conditions known to those skilled in the art (for example in the case of Boc, in the presence of a suitable acid (e.g. trifluoroacetic acid or HCl);

(v) for compounds wherein at least one $X^1$ is present and represents $NH_2$, reduction of a compound of formula VIII

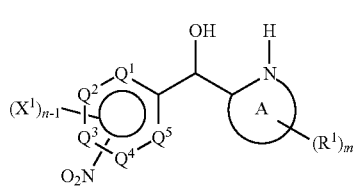
(VIII)

wherein $Q^1$ to $Q^5$, ring A, m, n, $X^1$ and $R^1$ are as defined hereinabove, under conditions known to those skilled in the art (for example, by hydrogenation, such as hydrogenation using hydrogen gas and a suitable catalyst as known to those skilled in the art, (e.g. Pd—C, $PtO_2$, Raney-Nickel), Fe or Zn in acidic media (e.g. AcOH), borohydrides together with a suitable catalyst (e.g. $NaBH_4$ and Raney-Nickel), or agents such as $SnCl_2$, $TiCl_3$, $SmI_2$, and the like). Those skilled in the art will understand that certain functional groups, such as the essential —OH and/or the —$NHR^1$ groups) may need to be protected (and deprotected) one or more times during the reaction, which protections (and deprotections) may be performed using techniques known to those skilled in the art;

(vi) deprotection of a compound of formula IX

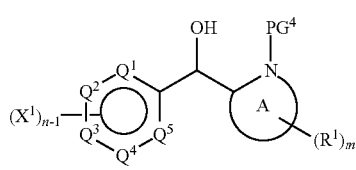
(IX)

wherein ring Q, ring A, n, m, $X^1$ and $R^1$ are as defined hereinabove, and $PG^4$ represents a suitable protecting group as known to those skilled in the art (e.g. a carbamate protecting group, such as tert-butyloxycarbonyl (Boc), fluorenylmethyloxycarbonyl (Fmoc) or carboxybenzyl (Cbz), or an amide protecting group, such as acetyl and benzoyl), under conditions known to those skilled in the art (for example in the case of Boc, in the presence of a suitable acid (e.g. trifluoroacetic acid or HCl); or (vii) reduction of a compound of formula X

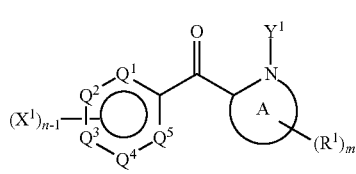
(X)

wherein ring Q, ring A, n, m, $X^1$ and $R^1$ are as defined herein and $Y^1$ represents H or $PG^5$ wherein $PG^5$ is a suitable protecting group as known to those skilled in the art, in the presence of a suitable catalyst (such as for a compounds having a stereocentre at the carbon bearing the essential OH group, e.g. compounds of formulas $IA^{1-4}$, a suitable catalyst may be a complex between (1S,2S)-(+)-N-(4-toluenesulphonyl)-1,2-diphenylethylene diamine and $[Ru(cymene)Cl_2]_2$)) in the presence of hydrogen or a suitable hydrogen donor (such as formic acid) and optionally in the presence of a base (e.g. $Et_3N$) and in the presence of a suitable solvent (such as $CH_2Cl_2$).

Compounds of formulae II, Ill, IV, V, VI, VII, VIII, IX, and X are either commercially available, are known in the literature, or may be obtained either by analogy with the processes described herein, or by conventional synthetic procedures, in accordance with standard techniques, from available starting materials (e.g. appropriately substituted benzaldehydes, styrenes or phenacyl bromides (or phenacylchloride, and the like) using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Science of Synthesis*", Volumes 9-17 (Hetarenes and Related Ring Systems), Georg Thieme Verlag, 2006.

The substituents X and $R^1$, as hereinbefore defined, may be modified one or more times, after or during the processes described above for preparation of compounds of formula I by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Such compounds may be isolated from their reaction mixtures and, if necessary, purified using conventional techniques as known to those skilled in the art. Thus, processes for preparation of compounds of the invention as described herein may include, as a final step, isolation and optionally purification of the compound of the invention (e.g. isolation and optionally purification of the compound of formula I).

The skilled person will understand that compounds of formula I having specific stereochemistry may be provided by reacting suitable starting materials having the required stereochemistry in processes as described herein. Further, the skilled person will understand that suitable starting materials having the required stereochemistry may be prepared by analogy with the processes described herein.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999).

Compounds as described herein (in particular, compounds as defined in the first and, therefore, second and third aspects of the invention) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, such compounds may have the advantage that they are more efficacious and/or exhibit advantageous properties in vivo.

Without wishing to be bound by theory, compounds as described herein are thought to be potent agonists of the $\beta_2$-adrenergic receptor, which allows for increased glucose uptake in skeletal muscle cells.

In addition, compounds as described herein are thought to be agonists of the $\beta_2$-adrenergic receptor without (or with only a minimal effect in) inducing cAMP production. It is thought that this allows for the increased glucose uptake in skeletal muscle cells with lower levels of side effects than would result from other treatments. Further, combining compounds as described herein with therapeutic agents that are able to decrease blood glucose levels is thought to provide an effective combination therapy.

EXAMPLES

The present invention is illustrated by way of the following examples.

Chemicals and reagents were obtained from commercial suppliers and were used as received unless otherwise stated. All reactions involving moisture sensitive reagents were performed in oven or flame dried glassware under a positive pressure of nitrogen or argon.

Abbreviations

Abbreviations as used herein will be known to those skilled in the art. In particular, the following abbreviations may be used herein.

AcOH acetic acid
aq aqueous
atm atmosphere
$Boc_2O$ di-tert-butyldicarbonate
BuLi butyl lithium
DIPEA N,N-diisopropylethylamine
DMAP 4-dimethylaminopyridine
DMF dimethylformamide
DMSO dimethylsulfoxide
eq equivalent
EtOAc ethyl acetate
HMPA hexamethylphosphoramide
MeCN acetonitrile
MeOH methanol
Pd—C palladium on carbon
rt room temperature
sat saturated
TFA trifluoroacetic acid
THF tetrahydrofuran
TMEDA N,N,N',N'-tetramethylethylenediamine Example Compounds In the event that there is a discrepancy between nomenclature and the structure of compounds as depicted graphically, it is the latter that presides (unless contradicted by any experimental details that may be given and/or unless it is clear from the context).

Example 1: (R)-(5-Fluoropyridin-3-yl)((2R,6S)-6-propylpiperidin-2-yl)methanol dihydrochloride (a) tert-Butyl (2R,6S)-2-((R)-(5-fluoropyridin-3-yl)(hydroxy)methyl)-6-propylpiperidine-1-carboxylate and tert-butyl (2R,6S)-2-((S)-(5-fluoropyridin-3-yl)(hydroxy)methyl)-6-propylpiperidine-1-carboxylate

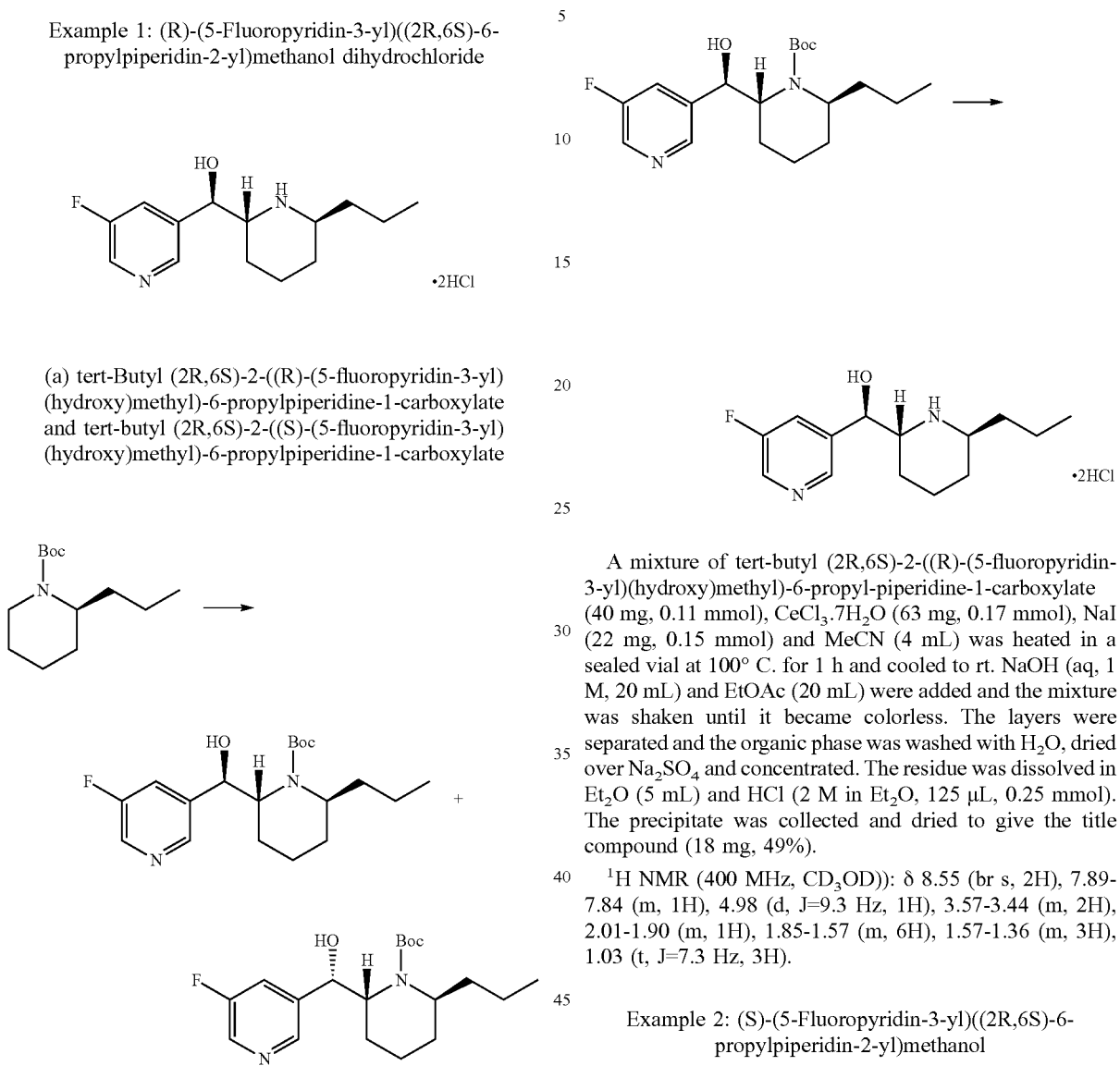

sec-BuLi (1.3 M in cyclohexane, 1.5 mL, 2.0 mmol) was added dropwise to a stirred mixture of tert-butyl (S)-2-propylpiperidine-1-carboxylate (300 mg, 1.32 mmol), TMEDA (0.30 mL, 2.0 mmol) and Et$_2$O (8 mL), keeping the temperature below −70° C. The mixture was allowed to warm to −30° C. over 1 h, kept at that temperature for 1 h and cooled to −78° C. 5-Fluoronicotinaldehyde (0.165 mg, 1.3 mmol) in Et$_2$O (4 mL) was added dropwise and the mixture was stirred at −78° C. for 30 min. H$_2$O (4 mL) was added and the mixture was allowed to warm to rt and extracted with Et$_2$O. The combined extracts were dried over Na$_2$SO$_4$ and concentrated. The residue was purified by chromatography to give tert-butyl (2R,6S)-2-((R)-(5-fluoropyridin-3-yl)(hydroxy)methyl)-6-propylpiperidine-1-carboxylate (50 mg, 11%) and tert-butyl (2R,6S)-2-((S)-(5-fluoropyridin-3-yl)(hydroxy)methyl)-6-propylpiperidine-1-carboxylate (86 mg, 19%).

(b) (R)-(5-fluoropyridin-3-yl)((2R,6S)-6-propylpiperidin-2-yl)methanol dihydrochloride A mixture of tert-butyl (2R,6S)-2-((R)-(5-fluoropyridin-3-yl)(hydroxy)methyl)-6-propyl-piperidine-1-carboxylate (40 mg, 0.11 mmol), CeCl$_3$·7H$_2$O (63 mg, 0.17 mmol), NaI (22 mg, 0.15 mmol) and MeCN (4 mL) was heated in a sealed vial at 100° C. for 1 h and cooled to rt. NaOH (aq, 1 M, 20 mL) and EtOAc (20 mL) were added and the mixture was shaken until it became colorless. The layers were separated and the organic phase was washed with H$_2$O, dried over Na$_2$SO$_4$ and concentrated. The residue was dissolved in Et$_2$O (5 mL) and HCl (2 M in Et$_2$O, 125 µL, 0.25 mmol). The precipitate was collected and dried to give the title compound (18 mg, 49%).

$^1$H NMR (400 MHz, CD$_3$OD)): δ 8.55 (br s, 2H), 7.89-7.84 (m, 1H), 4.98 (d, J=9.3 Hz, 1H), 3.57-3.44 (m, 2H), 2.01-1.90 (m, 1H), 1.85-1.57 (m, 6H), 1.57-1.36 (m, 3H), 1.03 (t, J=7.3 Hz, 3H).

Example 2: (S)-(5-Fluoropyridin-3-yl)((2R,6S)-6-propylpiperidin-2-yl)methanol

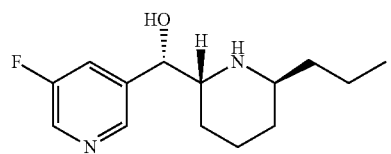 [SMILES: CCC[C@H]1CCC[C@H]([C@@H](O)c2cncc(F)c2)N1]

The title compound was prepared in accordance with the procedure in Example 1, Step (b) from tert-butyl (2R,6S)-2-((S)-(5-fluoropyridin-3-yl)(hydroxy)methyl)-6-propylpiperidine-1-carboxylate.

$^1$H NMR (400 MHz, CD$_3$OD): δ 8.98-8.94 (m, 1H), 8.87-8.85 (m, 1H), 8.57-8.51 (m, 1H), 5.36 (dd, J=3.2, 0.7 Hz, 1H), 3.83-3.71 (m, 1H), 3.57 (dq, J=8.6, 4.0 Hz, 1H), 1.98-1.85 (m, 1H), 1.84-1.74 (m, 3H), 1.72-1.56 (m, 3H), 1.55-1.35 (m, 3H), 1.03 (t, J=7.3 Hz, 3H).

Example 3: (R)-(5-Fluoropyridin-3-yl)((2R,5R)-5-propylpyrrolidin-2-yl)methanol maleate

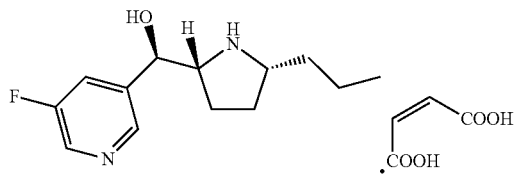

(a) Methyl (R)-2-((tert-butoxycarbonyl)amino)-5-oxooctanoate

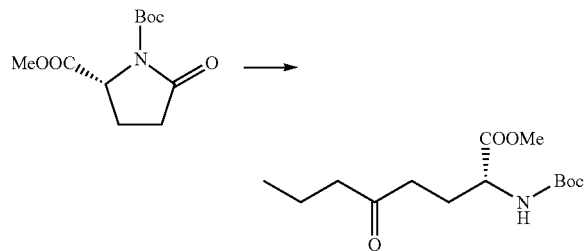

n-Propyl magnesium chloride (1 M in THF, 4.12 mL, 4.12 mmol) and TMEDA (616 µL, 4.12 mmol) was stirred at rt for 1 h and added via a syringe pump (0.1 mL/min) to a solution of 1-(tert-butyl) 2-methyl (R)-5-oxopyrrolidine-1,2-dicarboxylate (500 mg, 2.06 mmol) in THF (5 mL) at −78° C. The mixture was stirred at −78° C. for 2 h, NH$_4$Cl (aq, sat) was added and the mixture was extracted with Et$_2$O. The combined extracts were washed with brine, dried over Na$_2$SO$_4$ and concentrated. The residue was purified by chromatography to give the sub-title compound (535 mg, 91%).

(b) 1-(tert-Butyl) 2-methyl (2R,5R)-5-propylpyrrolidine-1,2-dicarboxylate

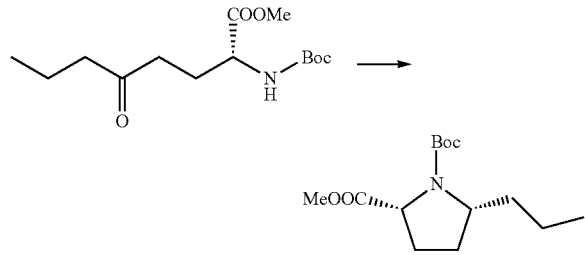

TFA (1.34 mL, 17.4 mmol) was added to a solution of methyl (R)-2-((tert-butoxycarbonyl)-amino)-5-oxooctanoate (500 mg, 1.74 mmol) in CH$_2$Cl$_2$ (1.5 mL) at rt and the mixture was stirred at rt for 3 h and concentrated. The residue was dissolved in iPrOH (97 mL), and Pd—C (10%, 93 mg, 0.087 mmol) was added. The mixture was hydrogenated at 8 atm for 2 h, filtered through Celite and concentrated. The residue was dissolved in CH$_2$Cl$_2$ (10 mL) and triethylamine (485 µL, 3.48 mmol), DMAP (43 mg, 0.35 mmol) and Boc$_2$O (950 mg, 4.35 mmol) were added. The mixture was stirred at rt overnight, washed with HCl (aq, 1 M) and brine, dried (Na$_2$SO$_4$) and concentrated. The residue was purified by chromatography to give the sub-title compound (422 mg, 89%).

(c) tert-Butyl (2R,5R)-2-(hydroxymethyl)-5-propylpyrrolidine-1-carboxylate

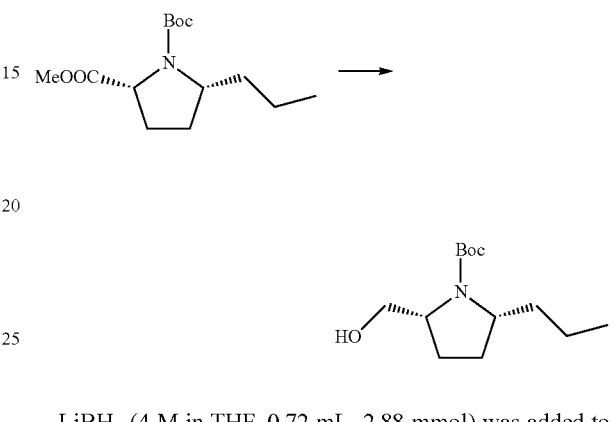

LiBH$_4$ (4 M in THF, 0.72 mL, 2.88 mmol) was added to 1-(tert-butyl) 2-methyl (2R,5R)-5-propylpyrrolidine-1,2-dicarboxylate (390 mg, 1.44 mmol) in THF at 0° C. The mixture was stirred at rt overnight and cooled to 0° C. Water was added and the mixture was extracted with Et$_2$O. The combined extracts were washed with brine, dried over MgSO$_4$, and concentrated to give the sub-title compound (324 mg, 93%).

(d) tert-Butyl (2R,5R)-2-formyl-5-propylpyrrolidine-1-carboxylate

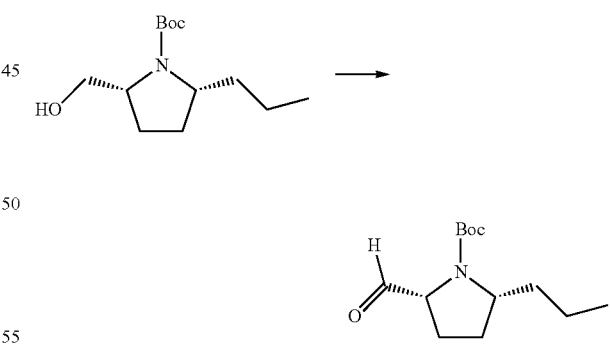

Dess-Martin periodinane (962 mg, 2.27 mmol) was added in portions to a mixture tert-butyl (2R,5R)-2-(hydroxymethyl)-5-propylpyrrolidine-1-carboxylate (368 mg, 1.51 mmol) and NaHCO$_3$ (318 mg, 3.78 mmol) and CH$_2$Cl$_2$ (12 mL) at 0° C. The mixture was vigorously stirred at rt for 90 min. Na$_2$S$_2$O$_3$ (aq, 10%) and NaHCO$_3$ (aq, sat) were added and the mixture was stirred for 30 min and extracted with Et$_2$O. The combined extracts were dried over MgSO$_4$ and concentrated. The residue was purified by chromatography to give the sub-title compound (310 mg, 85%).

(e) tert-Butyl (2R,5R)-2-((R)-(5-fluoropyridin-3-yl)(hydroxy)methyl)-5-propyl-pyrrolidine-1-carboxylate and tert-butyl (2R,5R)-2-((S)-(5-fluoropyridin-3-yl)(hydroxy)-methyl)-5-propylpyrrolidine-1-carboxylate

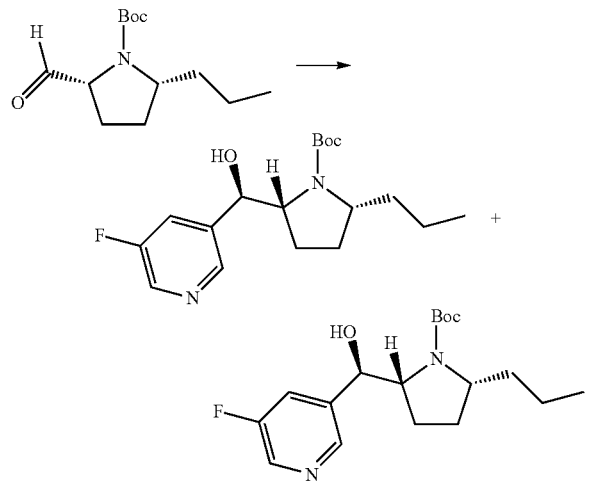

LnCl₃.2LiCl (0.6 M in THF, 1.1 mmol, 1.83 ml) was added to a solution of tert-butyl (2R,5R)-2-formyl-5-propylpyrrolidine-1-carboxylate (175 mg, 0.727 mmol) in THF (1 ml) at rt. The mixture was stirred at rt for 1 h and cooled in an ice-bath. Freshly prepared (5-fluoro-pyridin-3-yl)magnesium chloride (0.41 M in THF, 2.68 ml, 1.1 mmol), see Example 5, step (h), was added dropwise and the mixture was stirred at 0° C. for 1 h. NH₄Cl (aq, sat) was added and the mixture was extracted with CH₂Cl₂. The combined extracts were dried over Na₂SO₄ and concentrated. The residue was purified by chromatography to give tert-butyl (2R,5R)-2-((R)-(5-fluoropyridin-3-yl)(hydroxy)methyl)-5-propylpyrrolidine-1-carboxylate (83 mg, 34%) and tert-butyl (2R,5R)-2-((S)-(5-fluoropyridin-3-yl)(hydroxy)methyl)-5-propylpyrrolidine-1-carboxylate (81 mg, 33%);

(f) (R)-(5-fluoropyridin-3-yl)((2R,5R)-5-propylpyrrolidin-2-yl)methanol maleate

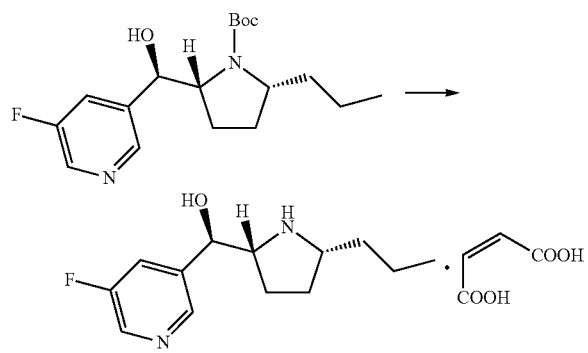

A mixture of tert-butyl (2R,5R)-2-((R)-(5-fluoropyridin-3-yl)(hydroxy)methyl)-5-propyl-pyrrolidine-1-carboxylate (67 mg, 0.20 mmol), CeCl₃.7H₂O (111 mg, 0.30 mmol), NaI (39 mg, 0.26 mmol) and MeCN (3 mL) was stirred at 100° C. for 1 h. EtOAc (10 mL) and NaOH (aq, 1 M, 10 mL) were added and the mixture was shaken until it turned colorless. The layers were separated and the organic phase washed with water, dried over Na₂SO₄ and concentrated. The residue was dissolved in EtOAc (0.2 mL) and maleic acid (23 mg, 0.20 mmol) in EtOAc (0.8 mL) was added. The mixture was concentrated and the residue was purified by reverse phase chromatography to give the title compound (29 mg, 41%).

¹H NMR (400 MHz, CD₃OD) δ 8.54-8.50 (m, 1H), 8.49-8.46 (m, 1H), 7.83-7.76 (m, 1H), 6.26 (s, 2H), 4.92-4.88 (m, 1H), 3.91-3.79 (m, 1H), 3.60-3.49 (m, 1H), 2.32-2.18 (m, 1H), 1.99-1.85 (m, 2H), 1.85-1.64 (m, 3H), 1.53-1.39 (m, 2H) 1.01 (t, J=7.3 Hz, 3H).

Example 4: (S)-(5-Fluoropyridin-3-yl)((2R,5R)-5-propylpyrrolidin-2-yl)methanol maleate

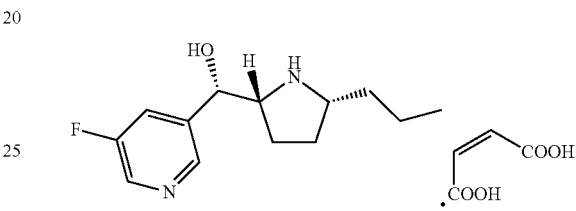

The title compound was prepared from (2R,5R)-2-((S)-(5-fluoropyridin-3-yl)(hydroxy)-methyl)-5-propylpyrrolidine-1-carboxylate (see Example 3, Step (e)) in accordance with the procedure in Example 3, Step (f).

¹H NMR (400 MHz, CD₃OD) δ 8.52-8.34 (m, 2H), 7.76-7.71 (m, 1H), 6.26 (s, 2H), 5.20-5.13 (m, 1H), 4.00-3.88 (m, 1H), 3.65-3.53 (m, 1H), 2.24-2.02 (m, 2H), 1.89-1.65 (m, 4H), 1.46 (h, J=7.5 Hz, 2H), 1.01 (t, J=7.2 Hz, 3H).

Example 5: (R)-((R)-5,5-Dimethylpyrrolidin-2-yl)(5-fluoropyridin-3-yl)methanol

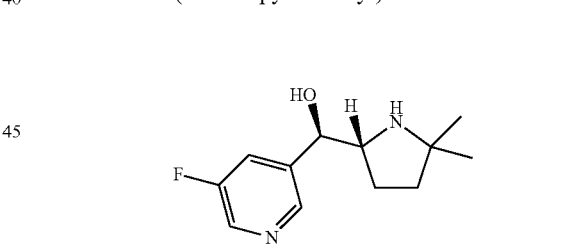

(a) (R)-5-(Hydroxymethyl)pyrrolidin-2-one

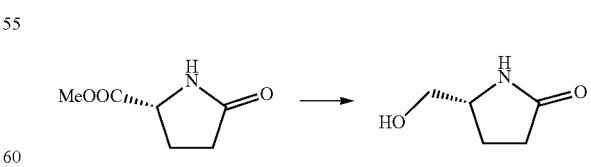

NaBH₄ (132 mg, 3.49 mmol) was added in portions to a mixture of methyl (R)-5-oxopyrrolidine-2-carboxylate (250 mg, 1.75 mmol) and MeOH (2 mL) at 0° C. The mixture was stirred at 0° C. for 90 min and concentrated. The residue was purified by chromatography to give the sub-title compound (190 mg, 95%).

(b) (R)-5-(((tert-Butyldimethylsilyl)oxy)methyl)pyrrolidin-2-one

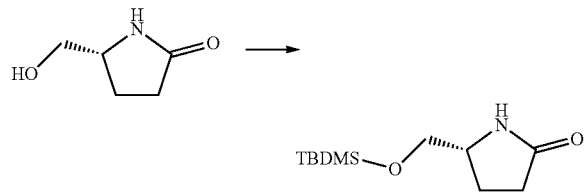

Imidazole (545 mg, 8.01 mmol) and tert-butyldimethylsilyl chloride (966 mg, 6.41 mmol) were added to a solution of (R)-5-(hydroxymethyl)pyrrolidin-2-one (615 mg, 5.34 mmol) in DMF (7 mL) at rt. The mixture was stirred at rt overnight and Et$_2$O and H$_2$O were added. The aq phase was extracted with Et$_2$O and the combined organic phases were washed with brine, dried over MgSO$_4$, filtered and concentrated to give the sub-title compounds (1.25 g, 99%) that was used in the next step without any further purification.

(c) (R)-1-Benzyl-5-(((tert-butyldimethylsilyl)oxy)methyl)pyrrolidin-2-one

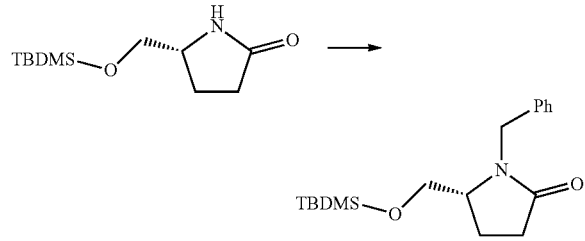

(R)-5-(((tert-Butyldimethylsilyl)oxy)methyl)pyrrolidin-2-one (1.24 g, 5.42 mmol) in THF (18.5 mL) was added dropwise to a mixture of NaH (60% dispersion in mineral oil, 325 mg, 8.13 mmol, washed with pentane) and THF (7 ml) at 0° C. The mixture was stirred at 0° C. for 10 min and benzyl bromide (0.97 mL, 8.13 mmol) was added. The ice-bath was removed and the mixture was stirred at rt for 10 min and at reflux for 90 min. The reaction was carefully quenched with H$_2$O. EtOAc was added and the aq phase was extracted with EtOAc. The combined organic phases were washed with brine, dried (Na$_2$SO$_4$) and concentrated. The residue was purified by chromatography to give the sub-title compound (1.35 g, 78%).

(d) (R)-1-Benzyl-5-(((tert-butyldimethylsilyl)oxy)methyl)-2,2-dimethylpyrrolidine

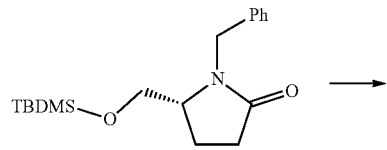

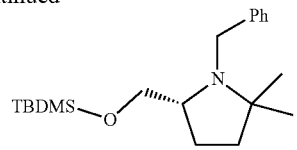

Freshly distilled triflic anhydride (1.66 mL, 10.14 mmol) was added dropwise to a solution of (R)-1-benzyl-5-(((tert-butyldimethylsilyl)oxy)methyl)pyrrolidin-2-one (2.70 g, 8.45 mmol), 2,6-di-tert-butyl-4-methylpyridine (2.08 g, 10.14 mmol) and CH$_2$Cl$_2$ (70 mL) at −78° C. The mixture was stirred at −78° C. for 45 min and methylmagnesium bromide (3 M in Et$_2$O, 8.45 mL, 25.35 mmol) was added dropwise. The stirred mixture was slowly allowed to reach rt over 2 h, quenched with NH$_4$Cl (aq, sat, 10 mL) and extracted with CH$_2$Cl$_2$. The combined organic phases were dried (Na$_2$SO$_4$) and concentrated. The residue was purified by chromatography to give the sub-title product (2.45 g, 87%).

(e) tert-Butyl (R)-5-(((tert-butyldimethylsilyl)oxy)methyl)-2,2-dimethylpyrrolidine-1-carboxylate

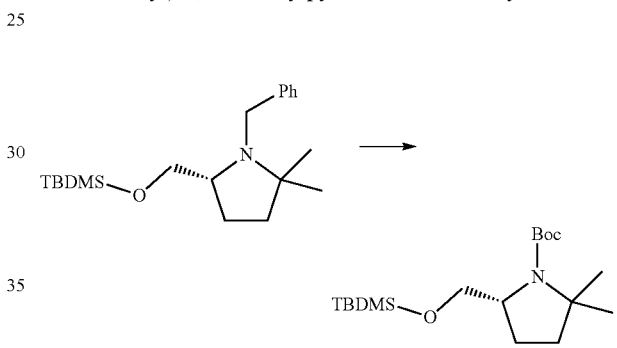

A solution of (R)-1-benzyl-5-(((tert-butyldimethylsilyl)oxy)methyl)-2,2-dimethylpyrrolidine (0.74 g, 2.22 mmol) in EtOAc (24.4 mL) was added to a mixture of Pd(OH)$_2$ on carbon (20%, 1.56 g, 1.11 mmol), Boc$_2$O (0.58 g, 2.66 mmol) and EtOAc (9.6 mL). The mixture was hydrogenated at ambient temperature and pressure for 20 h, filtered through Celite and concentrated. The residue was purified by chromatography to give the sub-title product (0.61 g, 81%).

(f) tert-Butyl (R)-5-(hydroxymethyl)-2,2-dimethylpyrrolidine-1-carboxylate

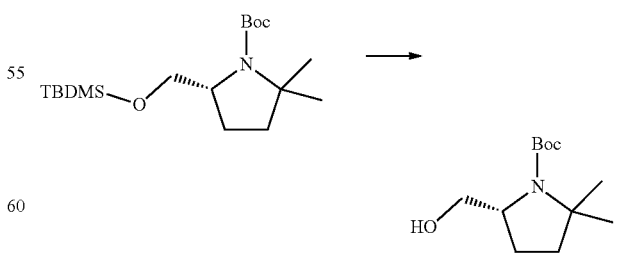

A solution of tetrabutylammonium fluoride in THF (1 M in THF, 3.58 mL, 3.58 mmol) was added to a solution of tert-butyl (R)-5-(((tert-butyldimethylsilyl)oxy)methyl)-2,2-dimethyl-pyrrolidine-1-carboxylate (0.61 g, 1.79 mmol) in THF (4.5 mL) at rt. The mixture was stirred at rt for 16 h, diluted with water and extracted with EtOAc. The combined extracts were washed with water, brine, dried over Na₂SO₄ and concentrated. The residue was purified by chromatography to give the sub-title compound (0.40 g, 99%).

(g) tert-Butyl (R)-5-formyl-2,2-dimethylpyrrolidine-1-carboxylate

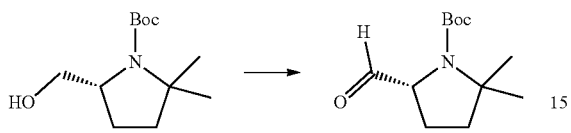

A solution of DMSO (0.31 mL, 4.41 mmol) in CH₂Cl₂ (1.9 mL) was added to a stirred mixture of oxalyl chloride (0.18 mL, 2.12 mmol) and CH₂Cl₂ (1.9 mL) at −78° C. After 30 min −78° C., a solution of tert-butyl (R)-5-(hydroxymethyl)-2,2-dimethylpyrrolidine-1-carboxylate (0.40 g, 1.76 mmol) in CH₂Cl₂ (3.6 mL) was added dropwise at −78° C. After 30 minutes at −78° C., triethylamine (1.23 mL, 8.83 mmol) was added and the mixture was allowed to warm to 0° C., stirred at 0° C. for 1 h, allowed to warm to rt and stirred at rt for 30 min. Water was added and the organic phase collected. The aq phase was extracted with CH₂Cl₂ and the combined organic phases were dried over MgSO₄ and concentrated. The residue was purified by chromatography to give the sub-title product (0.35 g, 87%).

(h) tert-Butyl (R)-5-((R)-(5-fluoropyridin-3-yl)(hydroxy)methyl)-2,2-dimethylpyrrolidine-1-carboxylate and tert-butyl (R)-5-((S)-(5-fluoropyridin-3-yl)(hydroxy)methyl)-2,2-dimethyl-pyrrolidine-1-carboxylate

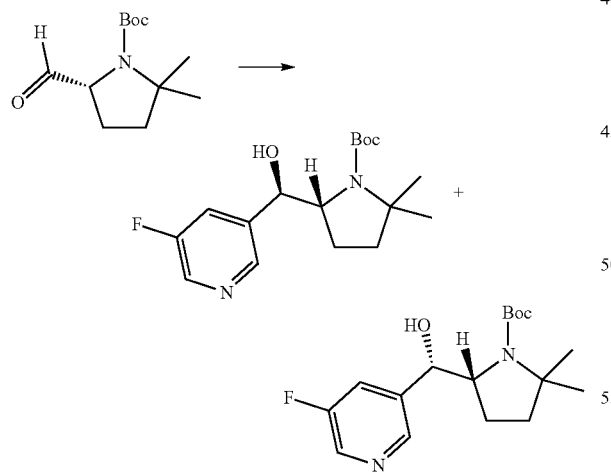

3-Bromo-5-fluoropyridine (139 mg g, 0.79 mmol) in THF (0.5 mL) was added dropwise to i-PrMgCl·LiCl complex (1.3 M in THF, 0.58 mL, 0.75 mmol) at 0° C. The mixture was allowed to ome to rt and stirred at rt for 30 min and added to CeCl₃ (0.56 g, 2.29 mmol) in THF (0.5 mL) at −78° C. The mixture was stirred at −78° C. for 1 h and tert-butyl (R)-5-formyl-2,2-dimethylpyrrol (0.33 g, 1.45 mmol) in THF (5 mL) was added dropwise. The mixture was stirred at −78° C. for 1 h and NH₄Cl (aq, sat) was added. The layers were separated and the aq phase was extracted with EtOAc. The combined organic phases were dried over Na₂SO₄ and concentrated. The residue was purified by chromatography to give tert-butyl (R)-5-((R)-(5-fluoropyridin-3-yl)(hydroxy)methyl)-2,2-dimethylpyrrolidine-1-carboxylate (0.050 g, 11%) and tert-butyl (R)-5-((S)-(5-fluoropyridin-3-yl)(hydroxy)-methyl)-2,2-dimethylpyrrolidine-1-carboxylate (0.19 g, 40%).

(i) (R)-((R)-5,5-dimethylpyrrolidin-2-yl)(5-fluoropyridin-3-yl)methanol

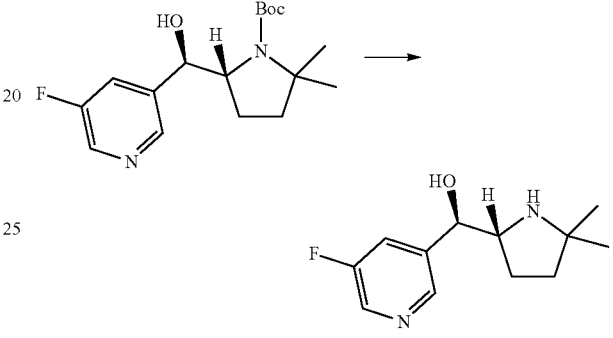

tert-Butyl (R)-5-((R)-(5-fluoropyridin-3-yl)(hydroxy)methyl)-2,2-dimethylpyrrolidine-1-carboxylate (50 mg, 0.15 mmol), CeCl₃.7H₂O (86 mg, 0.23 mmol), NaI (30 mg, 0.20 mmol) and MeCN (2 mL) were stirred at 100° C. for 1 h. The mixture was allowed to cool and EtOAc and NaOH (aq, 1 M) were added and mixtured shaken until the it turned colorless. The layers were separated and organic phase was washed with water, brine, dried over Na₂SO₄ and concentrated to give the title compound (25 mg, 72%).

¹H NMR (300 MHz, Chloroform-d) δ 8.44-8.28 (m, 2H), 7.48-7.38 (m, 1H), 4.39 (d, J=4.8 Hz, 1H), 3.42 (ddd, J=8.0, 5.9, 4.8 Hz, 1H), 2.07-1.91 (m, 1H), 1.90-1.52 (m, 3H), 1.22 (s, 3H), 1.18 (s, 3H).

Example 6: (S)-((R)-5,5-Dimethylpyrrolidin-2-yl)(5-fluoropyridin-3-yl)methanol

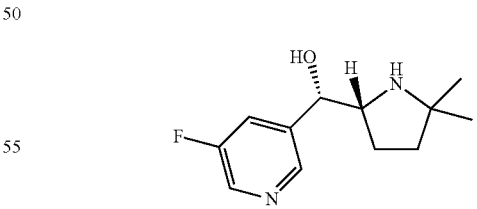

The title compound was prepared from tert-butyl (R)-5-((S)-(5-fluoropyridin-3-yl)-(hydroxy)methyl)-2,2-dimethylpyrrolidine-1-carboxylate (see Example 5, Step (h)) in accordance with the procedure in Example 5, Step (i).

¹H NMR (300 MHz, CDCl₃) δ 8.43-8.28 (m, 2H), 7.56-7.45 (m, 1H), 4.74 (d, J=3.6 Hz, 1H), 3.68 (td, J=7.6, 3.7 Hz, 1H), 3.40-2.84 (br s, 2H), 1.74-1.45 (m, 3H), 1.45-1.30 (m, 1H), 1.23 (s, 3H), 1.21 (s, 3H).

Example 7: (5-((R)-((R)-5,5-dimethylpyrrolidin-2-yl)(hydroxy)methyl)pyridin-3-ol

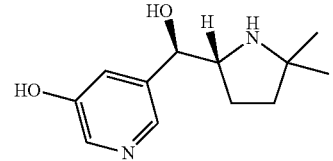 [SMILES: CC1(C)CC[C@H]([C@H](O)c2cncc(O)c2)N1]

(a) (R)-(1-Benzyl-5,5-dimethylpyrrolidin-2-yl)methanol

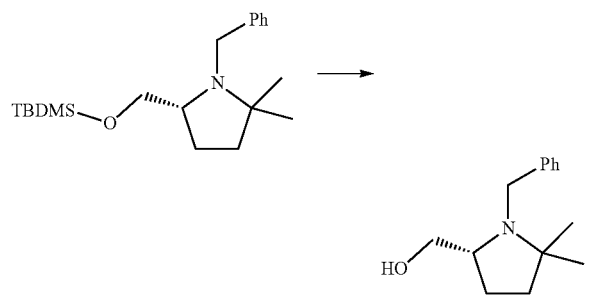

Tetrabutylammonium fluoride (1 M in THF, 14.7 mL, 14.7 mmol) was added to a solution of R)-1-benzyl-5-(((tert-butyldimethylsilyl)oxy)methyl)-2,2-dimethylpyrrolidine (2.45 g, 7.34 mmol), see Example 5, Step (d), in THF (18 mL) at rt. The mixture was stirred at rt overnight, diluted with $H_2O$ and extracted with EtOAc. The combined extracts were washed with $H_2O$, brine, dried ($Na_2SO_4$) and concentrated. The residue was purified by chromatography to give the sub-title product (1.31 g, 81%).

(b) ((R)-1-Benzyl-5,5-dimethylpyrrolidine-2-carbaldehyde

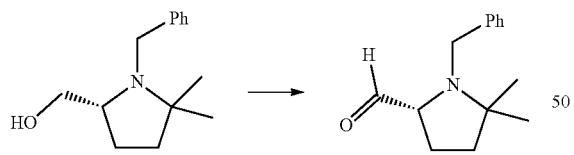

DMSO (1.05 mL, 14.82 mmol) in $CH_2Cl_2$ (6.5 mL) was added dropwise to oxalyl chloride (0.62 mL, 7.11 mmol) in $CH_2Cl_2$ (1 mL) at −78° C. After 30 min at −78° C. a solution of (R)-(1-benzyl-5,5-dimethylpyrrolidin-2-yl)methanol (1.30 g, 5.93 mmol) in $CH_2Cl_2$ (11.5 mL) was added. After 30 min at −78° C., triethylamine (4.1 mL, 29.6 mmol) was added dropwise. After 10 min at −78° C., the mixture was cooled in an ice-water bath and stirred for 30 min. $H_2O$ was added and the phases separated. The aq phase was washed with $CH_2Cl_2$ and the combined extracts were dried ($MgSO_4$) and concentrated. The residue was treated with $Et_2O$ and filtered through a cotton pad and concentrated to give the sub-title product (1.25 g, 97%), which was used in the next step without purification.

(c) (R)-((R)-1-Benzyl-5,5-dimethylpyrrolidin-2-yl)(5-(benzyloxy)pyridin-3-yl)methanol and (S)-((R)-1-benzyl-5,5-dimethylpyrrolidin-2-yl)(5-(benzyloxy)pyridin-3-yl)methanol

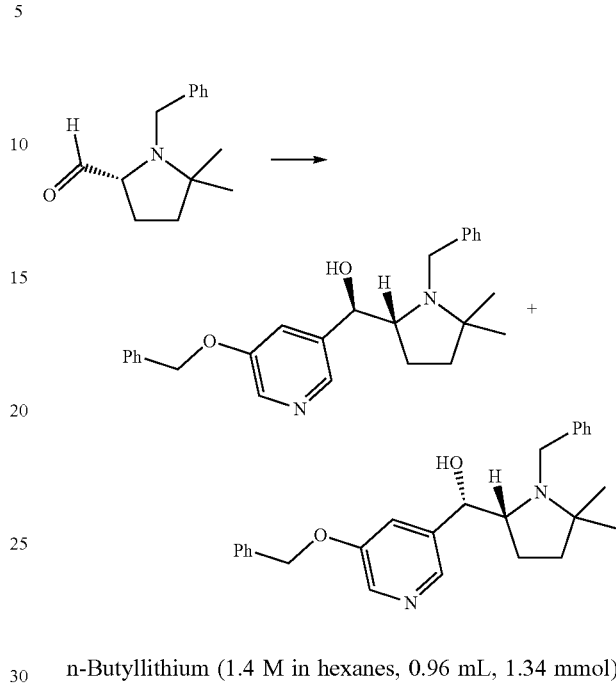

n-Butyllithium (1.4 M in hexanes, 0.96 mL, 1.34 mmol) was added dropwise over 10 min to 3-(benzyloxy)-5-bromopyridine (394 mg, 1.49 mmol) in THF (25 mL) at −100° C. After 1 h at −100° C. (R)-1-benzyl-5,5-dimethylpyrrolidine-2-carbaldehyde (270 mg, 1.24 mmol) in THF (15 mL) was added dropwise and the mixture was stirred at −100° C. for 1 hour and s allowed to warm to −60° C. and stirred for 30 minutes. $NH_4Cl$ (aq, sat) was added and the mixture was extracted with EtOAc). The combined extracts were washed with brine, dried over $Na_2SO_4$ and concentrated. The residue was purified by chromatography to give (R)-((R)-1-benzyl-5,5-dimethylpyrrolidin-2-yl)(5-(benzyloxy)pyridin-3-yl)methanol (73 mg, 15%) and (S)-((R)-1-benzyl-5,5-dimethylpyrrolidin-2-yl)(5-(benzyloxy)pyridin-3-yl)-methanol (160 mg, 32%).

(d) 5-((R)-((R)-5,5-Dimethylpyrrolidin-2-yl)(hydroxy)methyl)pyridin-3-ol

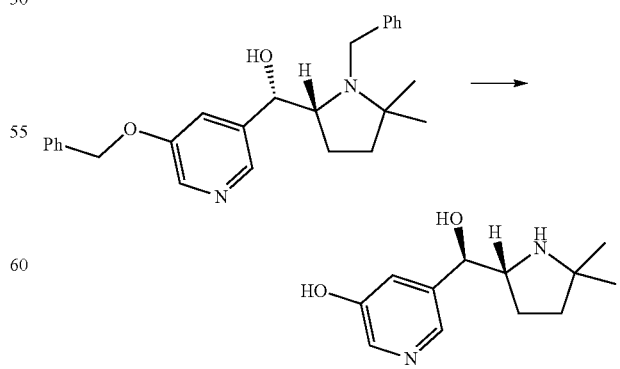

A mixture of (5-((R)-((R)-5,5-dimethylpyrrolidin-2-yl)(hydroxy)methyl)pyridin-3-ol (110 mg, 0.27 mmol), Pd—C (10%, 116 mg, 0.11 mmol) and iPrOH (7 ml) was hydrogenated at 6 bar at rt for 16 h. The mixture was filtered through Celite, concentrated and purified by reverse phase chromatography to give the title compound (21 mg, 35%).

$^1$H NMR (400 MHz, CD$_3$OD) δ 7.85 (d, J=2.6 Hz, 1H), 7.83-7.80 (m, 1H), 7.09 (t, J=2.3 Hz, 1H), 4.46 (d, J=7.3 Hz, 1H), 3.53 (q, J=7.1 Hz, 1H), 1.87-1.52 (m, 4H), 1.26 (s, 3H), 1.17 (s, 3H).

Example 8: 5-((S)-((R)-5,5-dimethylpyrrolidin-2-yl)(hydroxy)methyl)pyridin-3-ol

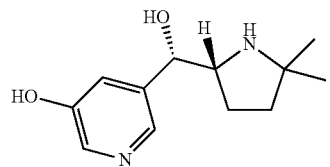 [SMILES: CC1(C)CC[C@H]([C@@H](O)c2cncc(O)c2)N1]

The title compound was prepared from (S)-((R)-1-benzyl-5,5-dimethylpyrrolidin-2-yl)(5-(benzyloxy)pyridin-3-yl)methanol, see Example 7, Step (g) in accordance with the procedures in Example 7, Step (h).

$^1$H NMR (400 MHz, CDCl$_3$): δ 7.32-7.22 (m, 1H), 7.16-7.06 (m, 2H), 6.97-6.86 (m, 1H), 4.72 (d, J=3.5 Hz, 1H), 3.39-2.79 (br s, 2H), 1.80-1.65 (m, 1H), 1.65-1.45 (m, 2H), 1.45-1.30 (m, 2H), 1.26 (s, 3H), 1.23 (s, 3H).

Example 9: (R)-((R)-4,4-Dimethylazetidin-2-yl)(5-fluoropyridine-3-yl)methanol dihydrochloride

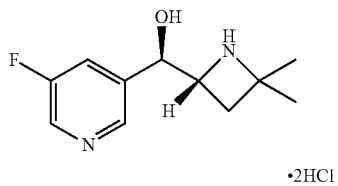

(a) 2-(Benzylamino)-2-methylpropan-1-ol

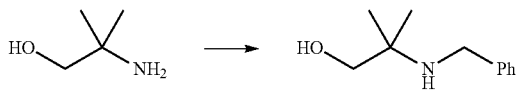

Benzaldehyde (3.4 mL, 33.7 mmol) was added dropwise to a stirred mixture of 2-amino-2-methylpropan-1-ol (3.0 g, 33.7 mmol), 5 Å molecular sieves (5 g) and CH$_2$Cl$_2$ (30 mL) at rt. The mixture was stirred at rt for 3 h, filtered through a pad of cotton and concentrated. MeOH (20 mL) followed by NaBH$_4$ (1.5 g, 40.4 mmol) was added and the mixture was stirred at rt for 1 h. NH$_4$Cl (aq, sat, 10 mL) was added and the mixture was concentrated, treated with NaOH (1 M, 20 mL) and extracted with EtOAc. The combined extracts were dried (Na$_2$SO$_4$) and concentrated to give the sub-title compound (5.8 g, 33.3 mmol, 96%), which was used in the next step without further purification.

(b) (2-(Benzyl(1-hydroxy-2-methylpropan-2-yl)amino)acetonitrile

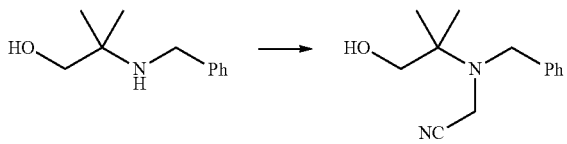 [SMILES: CC(C)(CO)NCc1ccccc1 ; CC(C)(CO)N(CC#N)Cc1ccccc1]

Bromoacetonitrile (5.3 mL, 78.1 mmol) and K$_2$CO$_3$ (5.8 g, 41.8 mmol) were added to a solution of 2-(benzylamino)-2-methylpropan-1-ol (5.0 g, 27.9 mmol) in MeCN (40 mL) at rt. The mixture was heated in a sealed vial for 16 h at 100° C. and concentrated. The residue was treated with H$_2$O and extracted with Et$_2$O. The combined extracts were dried (Na$_2$SO$_4$), concentrated and the residue purified by chromatography to give the sub-title compound (5.0 g, 22.8 mmol, 82%).

(c) 1-Benzyl-4,4-dimethylazetidine-2-carbonitrile

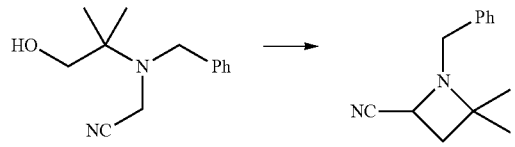

Diethyl chlorophosphate (2.1 mL, 14.4 mmol) was added drop-wise to a solution of 2-(benzyl(1-hydroxy-2-methylpropan-2-yl)amino)acetonitrile (3.0 g, 13.7 mmol) in THF (30 mL) at −20° C. Potassium bis(trimethylsilyl)amide (1 M in THF, 28.9 mL, 28.9 mmol) was added dropwise keeping the temperature below −15° C. and the mixture was stirred at −20° C. for 1 h. H$_2$O was added and the mixture was extracted with EtOAc. The combined extracts were dried (Na$_2$SO$_4$), concentrated and the residue purified by chromatography to give the sub-title compound (2.1 g, 10.5 mmol, 76%).

(d) 1-Benzyl-4,4-dimethylazetidine-2-carboxylic acid

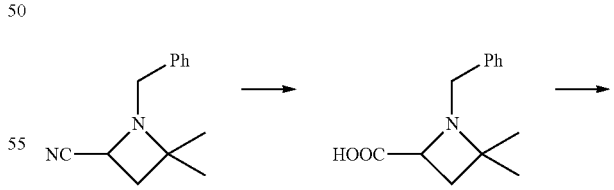

H$_2$O (5 mL) followed by NaOH (0.8 g, 20 mmol) were added to a solution of 1-benzyl-4,4-dimethylazetidine-2-carbonitrile (2.0 g, 9.1 mmol) in EtOH (10 mL) at rt. The mixture was heated in a sealed vial at 80° C. for 24 h and allowed to cool. The pH was adjusted to 7 with HCl (aq, 1 M) and the mixture was concentrated. The residue was extracted with CH$_2$Cl$_2$. Filtration and concentrated gave the sub-title compound (2.1 g, 9.6 mmol, 96%), which was used in the next step without any further purification.

(e) (1-Benzyl-4,4-dimethylazetidin-2-yl)methanol

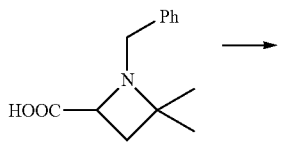

LiAlH₄ (2.4 M in THF, 7.6 mL, 18.2 mmol) was added dropwise to a mixture of 1-benzyl-4,4-dimethylazetidine-2-carboxylic acid (2.1 g, 9.6 mmol) and THF (40 mL) at 0° C. The mixture was stirred at 0° C. for 10 min, the cooling bath was removed and the stirring continued for 15 min. The mixture was carefully quenched by addition of NH₄Cl (aq, sat, 10 mL) and extracted with CH₂Cl₂. The combined extracts were dried (Na₂SO₄) and concentrated to give the sub-title compound (1.4 g, 6.8 mmol, 75%), which was used in the next step without further purification.

(f) tert-Butyl 4-(hydroxymethyl)-2,2-dimethylazetidine-1-carboxylate

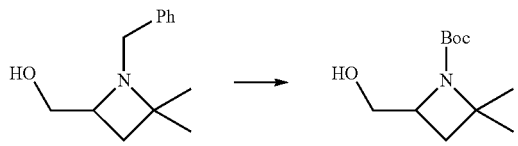

A mixture of (1-benzyl-4,4-dimethylazetidin-2-yl)methanol (1.4 g, 6.8 mmol), Boc₂O (2.4 mL, 10.2 mmol), Pd—C (10%, 0.72 g, 0.7 mmol) and EtOH (15 mL) was hydrogenated at normal pressure and temperature for 16 h and filtered through Celite. The solids were washed with EtOH and the combined liquids concentrated and purified by chromatography to give the sub-title compound (1.1 g, 5.1 mmol, 75%).

(g) tert-Butyl 4-formyl-2,2-dimethylazetidine-1-carboxylate

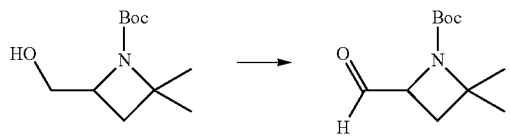

A suspension of Dess-Martin periodinane (1.30 g, 3.1 mmol) in CH₂Cl₂ (10 mL) was slowly added via a syringe to a solution of tert-butyl 4-(hydroxymethyl)-2,2-dimethylazetidine-1-carboxylate 550 mg, 2.6 mmol) in CH₂Cl₂ (20 mL) at rt. The mixture was stirred at rt for 1 h and quenched with Na₂S₂O₃ (aq, 10%) and NaHCO₃ (aq, sat), stirred for 10 min and extracted with CH₂Cl₂. The combined extracts were washed with NaHCO₃ (aq, sat), dried (Na₂SO₄) and concentrated to give the sub-title compound (495 mg, 2.32 mmol, 99%), which was used in the next step without further purification.

(h) tert-Butyl (R)-4-((R)-(5-fluoropyridin-3-yl)(hydroxy)methyl)-2,2-dimethylazetidine-1-carboxylate

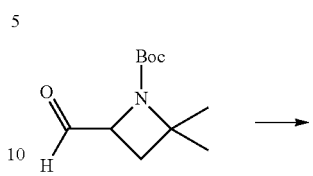

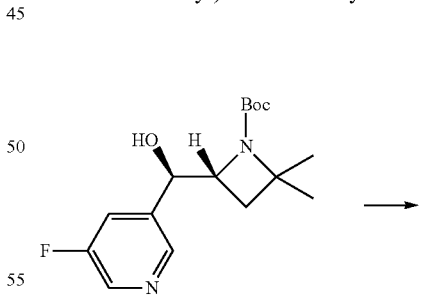

(5-Fluoropyridin-3-yl)magnesium bromide, freshly prepared from 3-bromo-5-fluoropyridine and iPrMgCl·LiCl, (1 M in THF, 3.52 mL, 3.52 mmol), see Example 5, step (h), was added dropwise to a solution of tert-butyl 4-formyl-2,2-dimethylazetidine-1-carboxylate (495 mg, 2.34 mmol) in THF (10 mL) at −20° C. The mixture was stirred at −20° C. for 30 min and then at rt for 1 h. NH₄Cl (aq, sat, 20 mL) was added and the mixture was extracted with Et₂O. The combined extracts were dried (Na₂SO₄) and concentrated and the residue purified chromatography to give a mixture of stereoisomers that were separated by preparative chiral chromatography to give the sub-title compound (85 mg, 0.27 mmol, 12%) along with the (R,S)-isomer (53 mg, 0.17 mmol, 7%), the (S,R)-isomer (50 mg, 0.16 mmol, 7%) and the (S,S)-isomer (73 mg, 0.23 mmol, 10%). The ee's of the different stereoisomers were 99%.

(i) (R)-((R)-4,4-Dimethylazetidin-2-yl)(2-fluorophenyl)methanol dihydrochloride

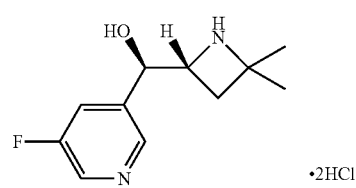

Example 10: (R)-((S)-4,4-Dimethylazetidin-2-yl)(5-fluoropyridine-3-yl)methanol dihydrochloride

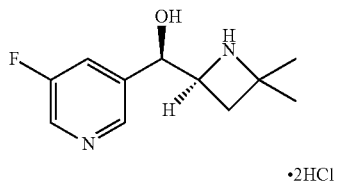

•2HCl

The title compound was prepared from tert-butyl (R)-4-((S)-(5-fluoropyridin-3-yl)(hydroxy)-methyl)-2,2-dimethyl-azetidine-1-carboxylate, see Example 9, Step (h) in accordance with the procedure in Example 9, Step (i).

$^1$H NMR (300 MHz, CD$_3$OD) δ 8.38 (t, J=1.7 Hz, 1H), 8.21 (d, J=2.8 Hz, 1H), 7.62-7.55 (m, 1H), 4.19 (d, J=6.9 Hz, 1H), 4.08 (q, J=7.2 Hz, 1H), 2.30 (br s, 2H), 2.12 (dd, J=12.8, 7.6 Hz, 1H), 1.77 (dd, J=12.8, 7.2 Hz, 1H), 1.36 (s, 3H), 1.25 (s, 3H).

Example 11: (S)-((S)-4,4-Dimethylazetidin-2-yl)(5-fluoropyridine-3-yl) methanol dihydrochloride

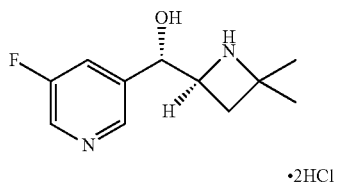

•2HCl

The title compound was prepared from tert-butyl (S)-4-((S)-(5-fluoropyridin-3-yl)(hydroxy)-methyl)-2,2-dimethyl-azetidine-1-carboxylate, see Example 9, Step (h) in accordance with the procedure in Example 9, Step (i).

$^1$H NMR (300 MHz, CD$_3$OD) δ 8.92 (t, J=2.2 Hz, 1H), 8.86 (br s, 1H), 8.51-8.45 (m, 1H), 5.22 (d, J=3.8 Hz, 1H), 4.71 (td, J=9.0, 3.8 Hz, 1H), 2.66 (dd, J=11.9, 9.0 Hz, 1H), 2.35 (dd, J=11.9, 8.9 Hz, 1H), 1.66 (s, 3H), 1.62 (s, 3H).

Example 12: (S)-((R)-4,4-Dimethylazetidin-2-yl)(5-fluoropyridin-3-yl)methanol dihydrochloride

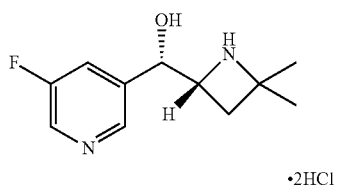

•2HCl

The title compound was prepared from tert-butyl (S)-4-((R)-(5-fluoropyridin-3-yl)(hydroxy)-methyl)-2,2-dimethylazetidine-1-carboxylate, see Example 9, Step (h) in accordance with the procedure in Example 9, Step (i).

$^1$H NMR (300 MHz, CD$_3$OD) δ 8.39 (t, J=1.7 Hz, 1H), 8.22 (d, J=2.8 Hz, 1H), 7.62-7.55 (m, 1H), 4.19 (d, J=6.8 Hz, 1H), 4.08 (q, J=7.2 Hz, 1H), 2.34 (br s, 2H), 2.13 (dd, J=12.8, 7.6 Hz, 1H), 1.77 (dd, J=12.8, 7.2 Hz, 1H), 1.37 (s, 3H), 1.25 (s, 3H).

Example 13: (R)-(5-Fluoropyridin-3-yl)((2R,7R)-7-propylazepan-2-yl)methanol

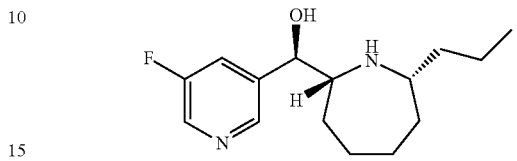

(a) Dibenzyl N,N-dibenzyl-D-glutamate

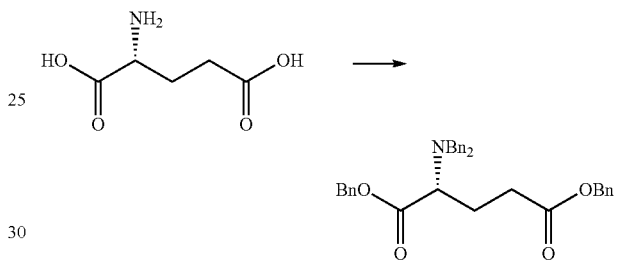

K$_2$CO$_3$ (3.76 g, 27.2 mmol) followed by NaOH (0.54 g (13.6 mmol) in portions were added to a solution of D-glutamic acid (1.0 g, 6.8 mmol) in H$_2$O (12 mL). The mixture was heated to reflux and benzyl bromide (3.3 mL, 27.8 mmol) was added dropwise over 15 min. The mixture was heated at reflux for 45 min, allowed to cool and diluted with Et$_2$O. The layers were separated and the aq phase was extracted with Et$_2$O. The combined organic phases were dried (Na$_2$SO$_4$), concentrated and the residue was purified by chromatography to give the sub-title compound (1.31 g, 2.59 mmol, 38%).

(b) Benzyl (R)-2-(dibenzylamino)-5-hydroxypentanoate

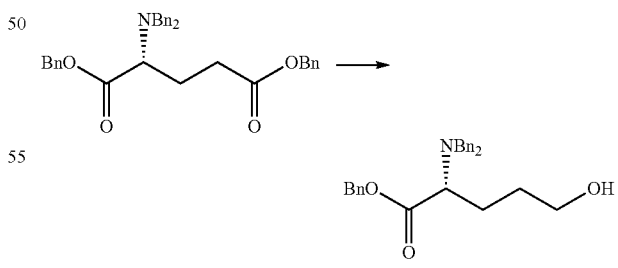

Diisobutylaluminium hydride (1 M in CH$_2$Cl$_2$, 3.8 mL, 3.82 mmol) was added dropwise to a mixture of dibenzyl N,N-dibenzyl-D-glutamate (970 mg, 1.91 mmol) and THF (10 mL) at −10° C. The mixture was stirred at 0° C. for 30 min, H$_2$O (1 mL) was added and the mixture was stirred at 0° C. for 25 min. The mixture was diluted with THF (5 mL), Na$_2$SO$_4$ was added and the mixture was stirred at rt for 15 min and filtered through Celite. The filter cake was washed with EtOAc and the combined filtrates were concentrated. The residue was purified by chromatography to give the sub-title compound (626 mg, 1.55 mmol, 81%).

(c) Benzyl (R)-2-(dibenzylamino)-5-oxopentanoate

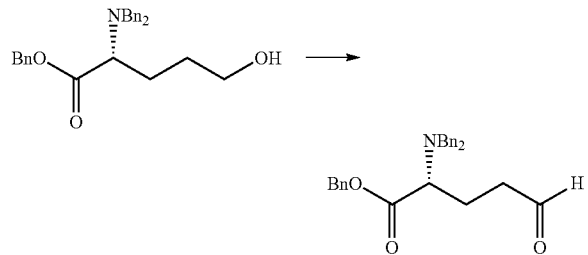

A solution of DMSO (0.28 mL, 3.88 mmol) in CH$_2$Cl$_2$ (1.6 mL) was added dropwise to a solution of oxalyl chloride (0.17 mL, 1.94 mmol) in CH$_2$Cl$_2$ (3.2 mL) at −78° C. After 30 min at −78° C. a solution of benzyl (R)-2-(dibenzylamino)-5-hydroxypentanoate (626 mg, 1.55 mmol) in CH$_2$Cl$_2$ (1.0 mL) was added dropwise and the mixture was stirred at −78° C. for 1 h before Et$_3$N (1.2 mL, 8.53 mmol) was added dropwise and the stirring was continued at −78° C. for 1 h and at 0° C. for 30 min. H$_2$O was added and the mixture was extracted with CH$_2$Cl$_2$. The combined organic phases were washed with HCl (aq, 1 M), NaHCO$_3$ (aq, sat) and brine, dried (Na$_2$SO$_4$) and concentrated to give the sub-title compound (0.606 mg, 1.51 mmol, 97%), which was used without further purification.

(d) Dimethyl (2-oxopentyl)phosphonate

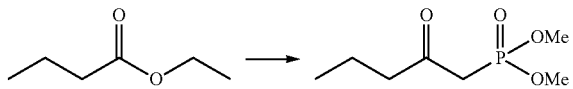

Dimethyl methylphosphonate (0.67 mL, 6.29 mmol) was added to a mixture of BuLi (2.5 M in hexane, 2.51 mL, 6.29 mmol) and THF (7 mL) at −78° C. and the mixture was stirred at −78° C. for 45 min. Ethyl butyrate (1.00 mL, 7.54 mmol) was added dropwise and the mixture was stirred for 30 min at −78° C. and was allowed to come to rt over 2 h. EtOAc was added and the mixture was washed with H$_2$O and brine. The combined washings were extracted with EtOAc and the combined organic phases were dried (Na$_2$SO$_4$) and concentrated. The residue was purified by chromatography to give the sub-title compound (531 mg, 2.73 mmol, 44%).

(e) Benzyl (R,E)-2-(dibenzylamino)-7-oxonon-5-enoate

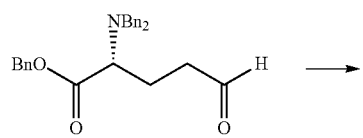

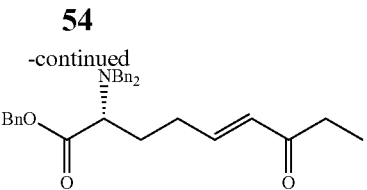

Dimethyl (2-oxopentyl)phosphonate (351 mg, 1.81 mmol) in MeCN (10 mL) followed by DIPEA (1.2 mL, 6.8 mmol) was added to a stirred mixture of LiCl (352 mg, 8.30 mmol) and MeCN (10 mL) at rt. After 2 h at rt, a solution of benzyl (R)-2-(dibenzylamino)-5-oxopentanoate (606 mg, 1.51 mmol) in MeCN (12 mL) was added and the mixture was stirred at rt for 18 h. Brine (30 mL) was added and the mixture was extracted with EtOAc. The combined extracts were dried (Na$_2$SO$_4$) and concentrated. The residue was purified by chromatography to give the sub-title compound (557 mg, 1.19 mmol, 79%).

(f) Methyl (2R,7R)-7-propylazepane-2-carboxylate

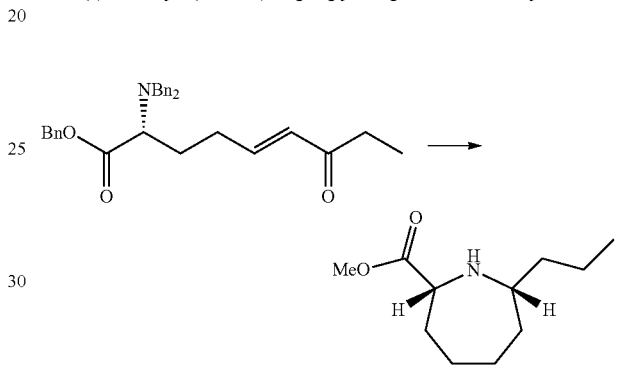

A mixture of benzyl (R,E)-2-(dibenzylamino)-7-oxonon-5-enoate (2.00 g, 4.26 mmol), Pd(OH)$_2$ on carbon (wet, 10%, 448 mg, 0.32 mmol), AcOH (2.8 mL) and MeOH (28 mL) was hydrogenated at 100° C. and 10 atm and pressure for 4 h, filtered through Celite and concentrated. The residue was dissolved in MeOH (23 mL) and cooled in an ice-bath. SOCl$_2$ (0.89 mL, 12.3 mmol) was added dropwise, the ice-bath was removed and the mixture stirred at rt for 18 h and concentrated. The residue was treated with CH$_2$Cl$_2$, washed with NaHCO$_3$ (aq, sat), dried (Na$_2$SO$_4$) and concentrated. The residue was purified by chromatography to give the sub-title compound (460 mg, 2.31 mmol, 66%) together with the corresponding (2R,7S) diastereomer (67 mg, 0.34 mmol, 10%).

(g) 1-(tert-Butyl) 2-methyl (2R,7R)-7-propylazepane-1,2-dicarboxylate

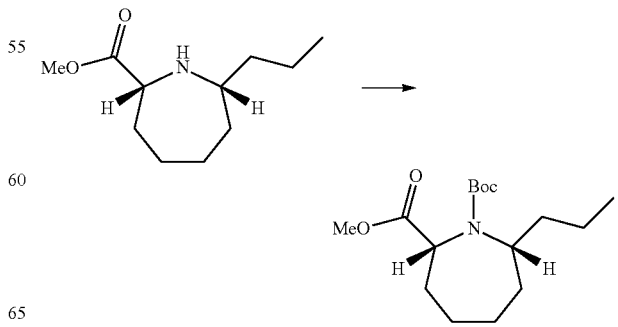

A mixture of methyl (2R,7R)-7-propylazepane-2-carboxylate (460 mg, 2.31 mmol) and Boc$_2$O (1.01 g, 4.62 mmol) was heated at 60° C. for 18 h. The mixture was dissolved in EtOH (20 mL) and imidazole (471 mg, 6.92 mmol) was added. The mixture was stirred at rt for 15 min, concentrated and the residue dissolved in CHCl$_3$. The mixture was washed with ice-cold HCl (aq., 1 M), brine and dried (Na$_2$SO$_4$), and concentrated. The residue was purified by chromatography to give the sub-title compound (530 mg, 1.77 mmol, 77%).

(h) tert-Butyl (2R,7R)-2-(hydroxymethyl)-7-propylazepane-1-carboxylate

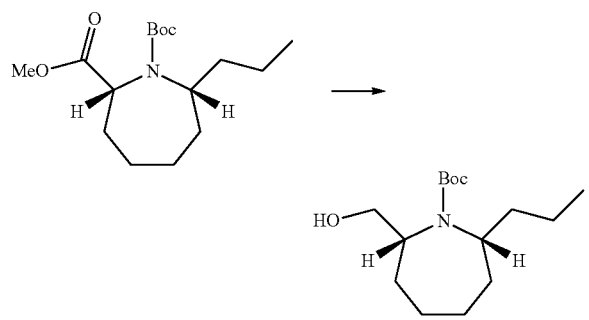

A solution of 1-(tert-butyl) 2-methyl (2R,7R)-7-propylazepane-1,2-dicarboxylate (330 mg, 1.10 mmol) in THF (1.7 mL) was added to an ice-cooled stirred mixture of LiAlH$_4$ (2.4 M in THF, 0.92 mL, 2.20 mmol) in THF (1.7 mL) at 0° C. The mixture was stirred at 0° C. for 1 h, carefully quenched by addition of NaOH (aq, 1 M) and extracted with EtOAc. The combined extracts were washed with brine, dried (Na$_2$SO$_4$) and concentrated. The residue was purified by chromatography to give the sub-title compound (250 mg, 0.92 mmol, 84%).

(i) tert-Butyl (2R,7R)-2-formyl-7-propylazepane-1-carboxylate

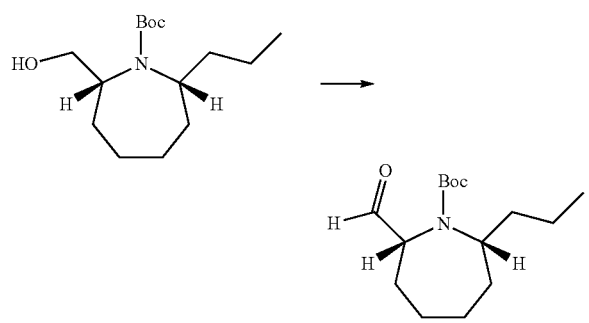

A solution of DMSO (163 μL, 2.30 mmol) in CH$_2$Cl$_2$ (1 mL) was slowly added to a solution of oxalyl chloride (96 μL, 1.10 mmol) in CH$_2$Cl$_2$ (1 mL) at −78° C. After 30 min at −78° C. a solution of tert-butyl (2R,7R)-2-(hydroxymethyl)-7-propylazepane-1-carboxylate (250 mg, 0.92 mmol) in CH$_2$Cl$_2$ (1.9 mL) was added dropwise and the mixture was stirred at −78° C. for 30 min before Et$_3$N (0.64 mL, 4.60 mmol) was added. The temperature was allowed to come to 0° C. and the stirring was continued at 0° C. for 1 h and at rt for 30 min. H$_2$O was added and the layers separated. The aq layer was extracted with CH$_2$Cl$_2$ and the combined organic phases were dried (MgSO$_4$) and concentrated. The residue was purified by chromatography to give the sub-title compound (230 mg, 0.85 mmol, 93%).

(j) tert-Butyl (2R,7R)-2-((R)-(5-fluoropyridin-3-yl)(hydroxy)methyl)-7-propylazepane-1-carboxylate

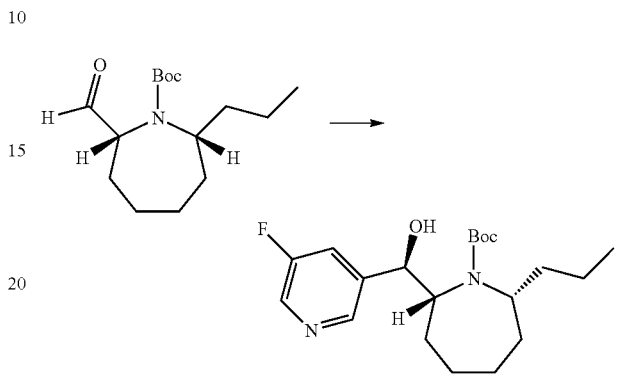

(5-Fluoropyridin-3-yl)magnesium bromide, freshly prepared from 3-bromo-5-fluoropyridine and iPrMgCl·LiCl, (0.5 M in THF, 1.11 mL, 0.56 mmol), see Example 5, step (h), was added dropwise to a solution of tert-butyl (2R,7R)-2-formyl-7-propylazepane-1-carboxylate (100 mg, 0.37 mmol) in THF (1 mL) at −78° C. The mixture was stirred at −78° C. for 30 min and then at rt for 18 h. NH$_4$Cl (aq, sat, 3 mL) was added and the mixture was extracted with CH$_2$Cl$_2$. The combined extracts were washed with brine, dried (MgSO$_4$) and concentrated and the residue was purified by preparative chiral chromatography to give the sub-title compound (22 mg, 60 pmol, 16%) along with the (R,R,S)-isomer (36 mg, 98 μmol, 26%).

(k) (R)-(5-fluoropyridin-3-yl)((2R,7R)-7-propylazepan-2-yl)methanol

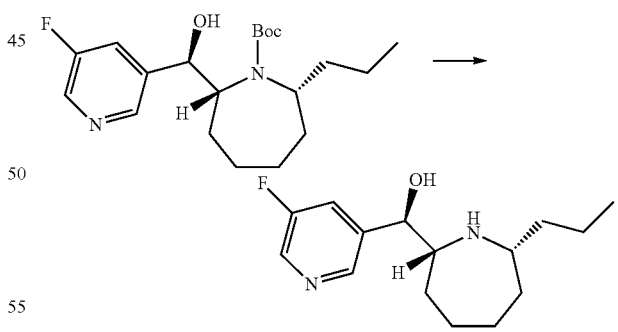

A mixture of tert-butyl (2R,7R)-2-((R)-(5-fluoropyridin-3-yl)(hydroxy)methyl)-7-propyl-azepane-1-carboxylate (16 mg, 44 μmol), CeCl$_3$.7H$_2$O (24.4 mg, 66 μmol), NaI (8.5 mg, 57 μmol) and MeCN (0.5 mL) was heated in a sealed vial at 100° C. for 1 h and cooled to rt. NaOH (aq, 1 M, 5 mL) and EtOAc (2 mL) were added and the mixture was shaken until it became colorless. The layers were separated and the organic phase was washed with H$_2$O, brine, dried over Na$_2$SO$_4$ and concentrated. The residue was dissolved in petroleum ether/Et$_2$O (20:1) and the solution filtered through amino-functionalized silica gel. Concentration of the filtrate gave the title compound (8 mg, 30 μmol, 69%).

$^1$H NMR (400 MHz, CDCl$_3$) δ 8.38 (m, 2H), 7.48 (dt, J=9.2, 2.3 Hz, 1H), 4.11 (d, J=9.0 Hz, 1H), 2.86-2.66 (m, 1H), 2.66-2.42 (m, 1H), 1.94-1.74 (m, 1H), 1.70-1.17 (m, 11H), 0.94 (t, J=6.8 Hz, 3H).

Example 14: (S)-(5-Fluoropyridin-3-yl)((2R,7R)-7-propylazepan-2-yl)methanol

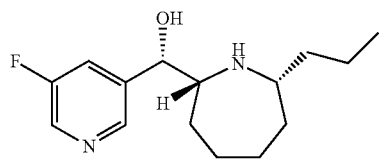 [SMILES: CCC[C@@H]1CCCC[C@H]([C@@H](O)c2cncc(F)c2)N1]

The title compound was prepared from tert-butyl (2R, 7R)-2-((S)-(5-fluoropyridin-3-yl)-(hydroxy)methyl)-7-propylazepane-1-carboxylate, see Example 13, Step (j), in accordance with the procedure described in Example 13, Step (k).

$^1$H NMR (400 MHz, CDCl$_3$) δ 8.43-8.25 (m, 2H), 7.37 (dt, J=9.4, 2.2 Hz, 1H), 4.66 (d, J=4.8 Hz, 1H), 3.11-2.90 (m, 1H), 2.84-2.62 (m, 1H), 1.91-1.15 (m, 12H), 0.92 (t, J=6.8 Hz, 3H)

Example 15: (R)-(5-Fluoropyridin-3-yl)(S,7S)-7-propylazepan-2-yl)methanol dihydrochloride

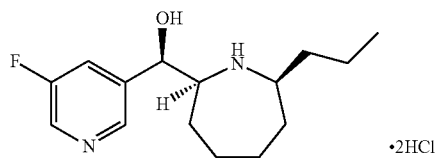 [SMILES: CCC[C@H]1CCCC[C@@H]([C@H](O)c2cncc(F)c2)N1 ; "·2HCl"]

The title compound was obtained from L-glutamic acid in accordance with the procedure in Example 13, Steps (a) to (k) followed by formation of the dihydrochloride salt in accordance with the procedure in Example 9, Step (i) and recrystallization from MeCN.

$^1$H NMR (400 MHz, CD$_3$OD) δ 8.52-8.50 (m, 1H), 8.43 (d, J=2.4 Hz, 1H), 7.85-7.67 (m, 1H), 5.37 (d, J=2.8 Hz, 1H), 3.74-3.59 (m, 1H), 3.47-3.35 (m, 1H), 2.09-1.95 (m, 1H), 1.92-1.35 (m, 11H), 1.02 (t, J=7.4 Hz, 3H).

Example 16: (S)-(5-Fluoropyridin-3-yl)(S,7S)-7-propylazepan-2-yl)methanol

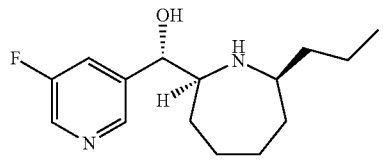 [SMILES: CCC[C@H]1CCCC[C@@H]([C@@H](O)c2cncc(F)c2)N1]

The title compound was obtained from L-glutamic acid in accordance with the procedure in Example 13, Steps (a) to (k).

$^1$H NMR (400 MHz, CDCl$_3$) δ 8.40-8.33 (m, 2H), 7.53-7.39 (m, 1H), 4.09 (d, J=9.1 Hz, 1H), 2.80-2.64 (m, 1H), 2.64-2.43 (m, 1H), 1.92-1.70 (m, 1H), 1.67-1.03 (m, 11H), 0.93 (t, J=6.9 Hz, 3H).

BIOLOGICAL EXAMPLES

L6-myoblasts were grown in Dulbecco's Modified Eagle's Medium (DMEM) containing 4.5 g/l glucose supplemented with 10% fetal bovine serum, 2 mM L-Glutamine, 50 U/ml penicillin, 50 μg/ml streptomycin and 10 mM HEPES. Cells were plated at 1×10$^5$ cells per ml in 24-well plates. After reaching 90% confluence the cells were grown in medium containing 2% FBS for 7 days where upon cells differentiated into myotubes.

Biological Example 1: Glucose Uptake

Differentiated L6-myotubes were serum-starved overnight in medium containing 0.5% fatty-acid free BSA and stimulated with agonist, final concentration 1×10$^{-5}$. After 1 h 40 min cells were washed with warm, glucose free medium or PBS and another portion of agonist was added to glucose free medium. After 20 min the cells were exposed to 50 nM $^3$H-2-deoxy-glucose for another 10 min before washed in ice cold glucose free medium or PBS and lysed in 0.2 M NaOH for 1 h in 60° C. Cell lysate was mixed with scintillation buffer (Emulsifier Safe, Perkin Elmer and radioactivity detected in a β-counter (Tri-Carb 2800TR, Perkin Elmer). The activity for each compound is compared to that of isoproterenol. If a compound shows activity of more than 75% of that of isoproterenol, the activity is denoted with +++, if it is between 75 and 50% it is denoted with ++; if it is between 50 and 25% it is denoted with +; if it less than 25% it is denoted with –.

Biological Example 2: Measurement of Intracellular cAMP Levels

Differentiated cells were serum-starved overnight and stimulated with agonist, final concentration 1×10$^{-5}$, for 15 min in stimulation buffer (HBSS supplemented with 1% BSA, 5 mM HEPES and 1 mM IBMX, pH 7.4) The medium was then aspirated and to end the reaction 100 μL of 95% EtOH was added to each well of a 24-well plate and cells were kept in –20° C. over night. The EtOH was let to evaporate and 500 μL of lysis buffer (1% BSA, 5 mM HEPES and 0.3% Tween-20, pH 7.4) was added to each well before put in –80° C. for 30 min and then kept in –20° C. Intracellular cAMP levels were detected using an alpha screen cAMP kit (6760635D from Perkin Elmer). The activity for each compound is compared to that of isoproterenol. If a compound shows activity of more than 75% of that of isoproterenol, the activity is denoted with +++, if it is between 75 and 50% it is denoted with ++; if it is between 50 and 25% it is denoted with +; if it less than 25% it is denoted with –.

Using the assays described in Biological Examples 1 and 2 the results shown in Tables 1 and 2 were obtained (na=not available).

TABLE 1

| Compound example no. | Biological example 1 | Biological example 2 |
|---|---|---|
| 1 | − | − |
| 2 | − | − |
| 3 | +++ | − |
| 4 | ++ | − |
| 5 | +++ | − |
| 6 | − | − |
| 7 | ++ | − |
| 8 | + | − |

TABLE 2

| Compound example no. | Biological example 3 | Biological example 4 |
|---|---|---|
| 9 | +++ | − |
| 10 | + | − |
| 11 | + | − |
| 12 | + | − |
| 13 | − | − |
| 14 | − | − |
| 15 | ++ | na |
| 16 | + | na |

The invention claimed is:

1. A compound of formula IC'

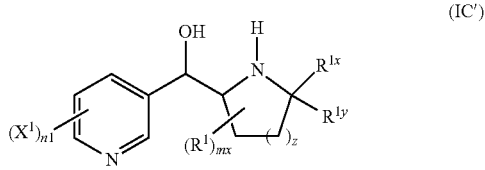

or a pharmaceutically acceptable salt thereof, wherein:
z represents 1 to 3;
n1 represents 1 to 4
each $R^1$ independently represents $C_{1-6}$ alkyl, $C_{2-6}$ alkenyl, or $C_{2-6}$ alkynyl each optionally substituted by one or more halo;
any two $R^1$ groups when attached to the same carbon may form together a 3- to 6-membered ring, which optionally is substituted by one or more groups independently selected from halo, $C_{1-6}$ alkyl, $C_{2-6}$ alkenyl, and $C_{2-6}$ alkynyl each optionally substituted by one more halo;
either
one of $R^{1x}$ and $R^{1y}$ represents an $R^1$ group and the other represents H, or
both of $R^{1x}$ and $R^{1y}$ represent an $R^1$ group;
wherein where one of $R^{1x}$ and $R^{1y}$ represents an $R^1$ group and the other represents H, then
when z represents 1 then mx represents 0 to 6, when z represents 2 then mx represents 0 to 8, and
when z represents 3 then mx represents 0 to 10;
wherein where both of $R^{1x}$ and $R^{1y}$ represent an $R^1$ group, then
when z represents 1 then mx represents 0 to 5, when z represents 2 then mx represents 0 to 7, and
when z represents 3 then mx represents 0 to 9;
each $X^1$ independently represents, as appropriate, halo, $R^a$, —CN, —N($R^b$)$R^c$, or —OR$^d$;
$R^a$ represents $C_{1-6}$ alkyl, $C_{2-6}$ alkenyl, or $C_{2-6}$ alkynyl each optionally substituted by one or more groups independently selected from $G^1$;
each $R^b$, $R^c$, and $R^d$ independently represents H, $C_{1-6}$ alkyl, $C_{2-6}$ alkenyl, or $C_{2-6}$ alkynyl each optionally substituted by one or more groups independently selected from $G^2$;
or alternatively any of $R^b$ and $R^c$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, and $C_{2-3}$ alkynyl each optionally substituted by one or more halo and =O;
$G^1$ and $G^2$ represents halo, —CN, —N($R^{a1}$)$R^{b1}$, —OR$^{c1}$, —S(O)$_p$R$^{d1}$, —S(O)$_q$N($R^{e1}$)$R^{f1}$ or =O;
each $R^{a1}$, $R^{b1}$, $R^{c1}$, $R^{d1}$, $R^{e1}$ and $R^{f1}$ independently represents H, or $C_{1-6}$ alkyl, $C_{2-6}$ alkenyl, or $C_{2-6}$ alkynyl each optionally substituted by one or more halo;
or alternatively any of $R^{a1}$ and $R^{b1}$ and/or $R^{e1}$ and $R^{f1}$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, and $C_{2-3}$ alkynyl each optionally substituted by one or more halo and =O;
each p independently represents 0, 1 or 2; and
each q independently represents 1 or 2,
wherein alkyl, alkenyl and alkynyl groups may be straight-chain or, when there is a sufficient number of carbon atoms, be branched-chain and/or cyclic or part cyclic.

2. The compound of claim 1, or a pharmaceutically acceptable salt thereof, each $X^1$ independently represents, as appropriate, halo, $R^a$, —CN, or —OR$^d$.

3. The compound of claim 1, or a pharmaceutically acceptable salt thereof, wherein each $R^1$ group independently represents $C_{1-3}$ alkyl optionally substituted by one or more halo.

4. The compound of claim 1, or a pharmaceutically acceptable salt thereof, wherein mx represents 1 to 2.

5. The compound of claim 1, or a pharmaceutically acceptable salt thereof, wherein n1 represents 1.

6. A pharmaceutical composition comprising a compound of claim 1, or a pharmaceutically acceptable salt thereof, and optionally one or more pharmaceutically acceptable adjuvants, diluents, and/or carriers.

7. The compound of claim 1, wherein z represents 1 or 2.

* * * * *